US012622584B2

(12) United States Patent
Shimizu et al.

(10) Patent No.: US 12,622,584 B2
(45) Date of Patent: May 12, 2026

---

(54) SLIT LAMP MICROSCOPE

(71) Applicant: Topcon Corporation, Tokyo (JP)

(72) Inventors: Hitoshi Shimizu, Tokyo (JP); Kazuhiro Omori, Tokyo (JP); Hisashi Tsukada, Hachioji (JP)

(73) Assignee: TOPCON CORPORATION, Tokyo (JP)

( * ) Notice: Subject to any disclaimer, the term of this patent is extended or adjusted under 35 U.S.C. 154(b) by 702 days.

(21) Appl. No.: 18/010,469

(22) PCT Filed: May 13, 2021

(86) PCT No.: PCT/JP2021/018134
§ 371 (c)(1),
(2) Date: Dec. 15, 2022

(87) PCT Pub. No.: WO2021/256130
PCT Pub. Date: Dec. 23, 2021

(65) Prior Publication Data
US 2023/0157542 A1 May 25, 2023

(30) Foreign Application Priority Data
Jun. 17, 2020 (JP) ................................ 2020-104223

(51) Int. Cl.
*A61B 3/135* (2006.01)
*A61B 3/117* (2006.01)

(52) U.S. Cl.
CPC .............. *A61B 3/135* (2013.01); *A61B 3/117* (2013.01)

(58) Field of Classification Search
CPC ......... A61B 3/135; A61B 3/0025; A61B 3/10; A61B 3/14; A61B 3/117; G02B 21/0012; G02B 21/0032
See application file for complete search history.

(56) References Cited

U.S. PATENT DOCUMENTS 4,877,321 A * 10/1989 Ichihashi ............... A61B 3/135
351/221
6,155,683 A 12/2000 Hanaki et al.
(Continued)

FOREIGN PATENT DOCUMENTS

CN 110335254 * 10/2019 .............. G06T 7/00
EP 4 023 142 A1 7/2022
(Continued)

OTHER PUBLICATIONS

International Search Report and Written Opinion mailed on Jun. 22, 2021, received for PCT Application PCT/ JP2021/018134, filed on May 13, 2021, 8 pages including English Translation.
(Continued)

*Primary Examiner* — Brandi N Thomas
(74) *Attorney, Agent, or Firm* — XSENSUS LLP

(57) ABSTRACT
A slit lamp microscope according to an embodiment example includes a scanner, a first assessing processor, and a controller. The scanner is configured to perform application of a scan to an anterior segment of a subject's eye with slit light to collect an image group. The first assessing processor is configured to execute an assessment of a quality of the image group collected by the scanner. The controller is configured to selectively execute at least two control modes according to a result of the assessment of the quality obtained by the first assessing processor.

18 Claims, 25 Drawing Sheets

(56)                    References Cited

U.S. PATENT DOCUMENTS

| | | | |
|---|---|---|---|
| 6,692,126 | B1 | 2/2004 | Xie et al. |
| 2003/0071968 | A1 | 4/2003 | Lai et al. |
| 2004/0207811 | A1 | 10/2004 | Elsner |
| 2015/0085252 | A1 | 3/2015 | Fujimura et al. |
| 2016/0345822 | A1 | 12/2016 | Fujimura et al. |
| 2019/0053703 | A1 | 2/2019 | Berestka et al. |
| 2021/0015363 | A1 | 1/2021 | Ohmori et al. |
| 2021/0153740 | A1 | 5/2021 | Oomori et al. |
| 2022/0248953 | A1 | 8/2022 | Shimizu et al. |

FOREIGN PATENT DOCUMENTS

| | | | | |
|---|---|---|---|---|
| EP | 4023142 | * | 7/2022 | ........... A61B 31/135 |
| JP | 11-276439 | A | 10/1999 | |
| JP | 2000-116732 | A | 4/2000 | |
| JP | 2008-284273 | A | 11/2008 | |
| JP | 2010-29721 | A | 2/2010 | |
| JP | 2013-248376 | A | 12/2013 | |
| JP | 2016-159073 | A | 9/2016 | |
| JP | 2016-179004 | A | 10/2016 | |
| JP | 2019-154829 | A | 9/2019 | |
| JP | 2019-213729 | A | 12/2019 | |
| JP | 2019-213734 | A | 12/2019 | |
| WO | 03/03283 | A2 | 4/2003 | |

OTHER PUBLICATIONS

Japanese Office Action issued Feb. 4, 2025, in corresponding Japanese Patent Application No. 2024-138437, 4pp.
Extended European Search Report issued Jun. 4, 2024, in corresponding European Patent Application No. 21826892.8, 10pp.

* cited by examiner

SLIT LAMP MICROSCOPE

CROSS-REFERENCE TO RELATED APPLICATIONS

This application is a national stage (under 35 U.S.C. 371) of International Patent Application No. PCT/JP2021/018134, filed May 13, 2021, claiming priority to Japanese Patent Application No. 2020-104223, filed Jun. 17, 2020, both of which are herein incorporated by reference in their entirety.

FIELD

The present disclosure relates to a slit lamp microscope.

BACKGROUND

Diagnostic imaging serves an important role in the field of ophthalmology. Diagnostic imaging uses various kinds of ophthalmic imaging apparatuses. Types of examples of ophthalmic imaging apparatuses include a slit lamp microscope, a fundus camera, a scanning laser ophthalmoscope (SLO), an optical coherence tomography (OCT) apparatus, and so forth.

A slit lamp microscope is the most widely and frequently utilized apparatuses among such various kinds of ophthalmic apparatuses. A slit lamp microscope is used for illuminating a subject's eye with slit light and observing and/or photographing the illuminated cross section from an oblique or side position with a microscope (see, for example, following Patent Documents 1 and 2).

One of the main uses of a slit lamp microscope is observation of anterior eye segments. When observing an anterior eye segment, a doctor observes an entire anterior eye segment while moving the focal position and the area illuminated by slit light, thereby determining the presence or absence of abnormality. Further, a slit lamp microscope may also be used for prescription of vision correction devices such as for checking of a fitting state of a contact lens. In addition, a slit lamp microscope may also be used by a person, such as an optometrist, allied health professional, or a clerk in an optician's store, who is not a medical doctor in order to conduct screening for eye diseases or the like.

Recent advances in information and communication technology have been enhancing the progress of research and development related to telemedicine. Telemedicine is the act of using communication networks such as the Internet to provide medical care (diagnosis, treatment) to patients in remote places. Techniques for operating a slit lamp microscope from a remote location are disclosed in the following Patent Documents 3 and 4.

[PATENT DOCUMENT 1] Japanese Unexamined Patent Application Publication No. 2016-159073

[PATENT DOCUMENT 2] Japanese Unexamined Patent Application Publication No. 2016-179004

[PATENT DOCUMENT 3] Japanese Unexamined Patent Application Publication No. 2000-116732

[PATENT DOCUMENT 4] Japanese Unexamined Patent Application Publication No. 2008-284273

BRIEF SUMMARY

In general, acquisition of an appropriate image using a slit lamp microscope requires fine and complicated operations such as illumination angle adjustment and photographing angle adjustment. The techniques disclosed in Patent Documents 3 and 4 require an examiner, who is at a remote place, to conduct operations that are difficult even in the case where the examiner is observing the eyes of a subject face to face. This causes problems such as prolongation of examination time length and impossibility of acquisition of good images.

While slit lamp microscopes are useful and effective for screening and other examinations as described above, a current problem is that shortage of persons who are skilled in operating slit lamp microscopes makes it impossible for high quality slit lamp microscope examinations to be provided to many people.

Furthermore, in telemedicine and screening, it is often the case that the doctor who conducts image interpretation (image diagnosis) is not present at the location where photography is performed. If this is the case, there is a possibility (risk) that the doctor may be provided with an image that is not suitable for image interpretation. Considering the difficulty of operation and the long length of time required for photographing, it is supposed that this problem is more likely to occur with slit lamp microscopes.

An object of the present disclosure is to make it possible to widely provide high quality slit lamp microscope examinations.

A slit lamp microscope according to some aspect examples of the present disclosure includes: a scanner configured to perform application of a scan to an anterior segment of a subject's eye with slit light to collect an image group; a first assessing processor configured to execute an assessment of a quality of the image group collected by the scanner; and a controller configured to selectively execute at least two control modes according to a result of the assessment of the quality obtained by the first assessing processor.

The aspect examples according to the present disclosure is capable of widely providing high quality slit lamp microscope examinations.

DETAILED DESCRIPTION

Figure 1:
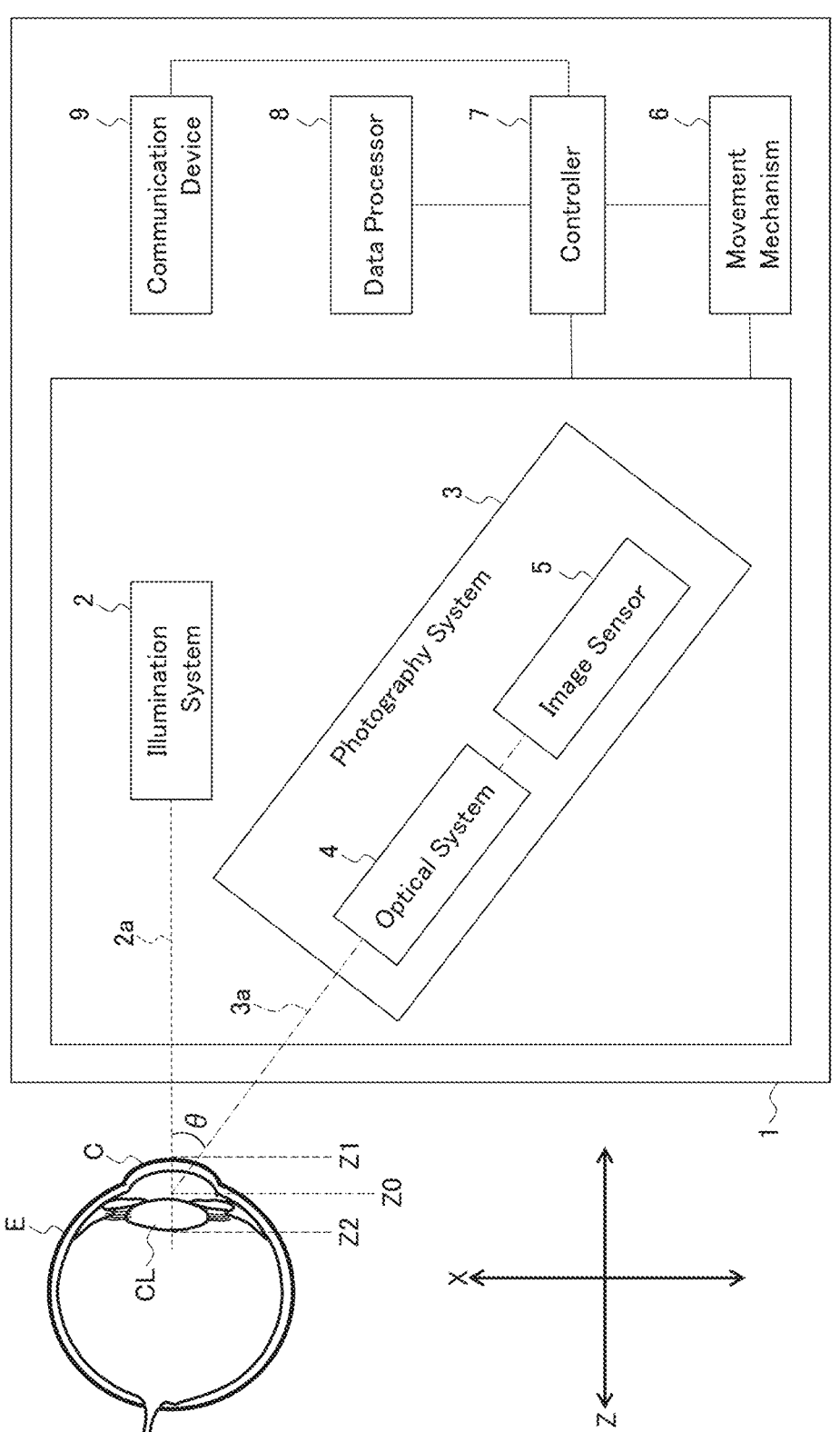
FIG. 1 is a schematic diagram illustrating a configuration of a slit lamp microscope according to an aspect example.

Some aspect examples will be described in detail with referring to the drawings. It should be noted that any known techniques or technologies such as any of the matters or items disclosed in the documents cited herein may be combined with the aspect examples. In addition, the entire disclosures of any of other patent applications filed by the present applicant may be incorporated into the present disclosure. For example, the entire disclosure of any of other patent applications relating to a slit lamp microscope (or relating to a system that includes a slit lamp microscope, or relating to a system connectable to a slit lamp microscope) filed by the present applicant may be incorporated into the present disclosure.

The slit lamp microscope according to some aspect examples may be a stationary type or a portable type. The slit lamp microscope according to some aspect examples is typically used in situations and/or environments where no technical experts (skilled persons) relating to the apparatus is present nearby. Note that the slit lamp microscope according to some aspect examples may be used in situations and/or environments where a skilled person is present, or in situations and/or environments where a skilled person can provide monitoring, give instructions, and/or conduct an apparatus operation, from a remote place.

Examples of the facility in which the slit lamp microscope is installed include an optician's store, an optometrist's office, a health facility, a medical institution, a health check and screening venue, a patient's home, a welfare facility, a public facility, a medical examination vehicle, and so forth.

The slit lamp microscope according to some aspect examples is an ophthalmic imaging apparatus having at least the function of a slit lamp microscope, and may be further provided with any other photographing or imaging functions performed by other modality apparatuses. Examples of such other modality apparatuses include an anterior segment camera, a fundus camera (retinal camera), an SLO, an OCT apparatus, and so forth. The slit lamp microscope according to some aspect examples may further have any of the functions of measuring characteristics of eyes. Examples of such measurement functions include visual acuity measurement, refraction measurement, intraocular pressure measurement, corneal endothelial cell measurement, aberration measurement, visual field measurement, and so forth. The slit lamp microscope according to some aspect examples may further include application software for analyzing photographed images, measurement data, or the like. The slit lamp microscope according to some aspect examples may further include any of the functions for treatment or surgery. Examples of such treatment or surgery includes photocoagulation treatment and photodynamic therapy.

The ophthalmic system according to some aspect examples (first ophthalmic system) may include one or more slit lamp microscopes, one or more information processing apparatuses, and one or more image interpretation computer terminals, and may be used for telemedicine, for example. The slit lamp microscope may be a slit lamp microscope according to any aspect example, or may be a slit lamp microscope including at least part of a slit lamp microscope according to any aspect example.

The information processing apparatus is configured to receive an image acquired by the slit lamp microscope and transmit the image to the image interpretation computer terminal. In addition, the information processing apparatus may have a function of managing images acquired by the slit lamp microscope(s).

The image interpretation computer terminal is a computer used by a doctor (typically, a specialist such as an ophthalmologist or a medical image interpreter) to conduct interpretation of an image acquired by the slit lamp microscope. Here, the interpretation is an act of observing an image to obtain medical findings. Information entered into the image interpretation computer terminal by the person who has conducted the image interpretation may, for example, be converted by the image interpretation computer terminal or another computer into an image interpretation report or electronic medical record information and then transmitted to the information processing apparatus. In another example, information entered into the image interpretation computer terminal by a person who conducts image interpretation may be transmitted to the information processing apparatus. In this case, the information processing apparatus or another computer may perform conversion of the information entered by the person who conducts the image interpretation into an image interpretation report or electronic medical record information. The information processing apparatus may be configured to perform management of image interpretation reports or electronic medical record information by itself, or to transfer image interpretation reports or electronic medical record information to another medical system (e.g., an electronic medical record system).

An ophthalmic system according to another aspect example (second ophthalmic system) may include one or more slit lamp microscopes, one or more information processing apparatuses, and one or more image interpretation apparatuses. At least one of the slit lamp microscope and the information processing apparatus may be the same as or similar to that (those) of the first ophthalmic system.

The image interpretation apparatus is a computer configured to perform interpretation of an image acquired by the slit lamp microscope, using an artificial intelligence engine (inference engine, inference model, etc.) and/or an image processing processor configured to operate according to a predetermined program. Information derived from the image by the image interpretation apparatus may be converted by the image interpretation apparatus or another computer into an image interpretation report or electronic medical record information and then transmitted to the information processing apparatus, for example. In another example, information derived from the image by the image interpretation apparatus may be transmitted to the information processing apparatus. In this case, the information processing apparatus or another computer may convert the information derived from the image by the image interpretation apparatus into an image interpretation report or electronic medical record information. The information processing apparatus may be configured to perform management of image interpretation reports or electronic medical record information by itself, or to transfer image interpretation reports or electronic medical record information to another medical system.

An ophthalmic system according to yet another aspect example (third ophthalmic system) may include one or more slit lamp microscopes and one or more information processing apparatuses. The slit lamp microscope may be the same as or similar to that of the first ophthalmic system. The information processing apparatus may be the same as or similar to that of the first ophthalmic system and/or that of the second ophthalmic system. In other words, the information processing apparatus may be capable of performing data communication with the image interpretation computer terminal of the first ophthalmic system, and/or, may be capable of performing data communication with the image interpretation apparatus of the second ophthalmic system.

The slit lamp microscopes and the ophthalmic systems according to some aspect examples can be used in telemedicine. As mentioned above, acquisition of an eligible image (good image, satisfactory image) using a slit lamp microscope is not an easy task. In addition, effective image interpretation and diagnosis require acquisition of an image of a wide area of an anterior eye segment "in advance". For these reasons, it can be said that effective telemedicine using slit lamp microscopes has not been achieved. Some aspect examples can provide technologies and techniques that contribute to the achievement (realization, implementation) of effective telemedicine with slit lamp microscopes. However, the use of some aspect examples is not limited to this, and some aspect examples may also be applied to other uses.

Some aspect examples are especially focused on the following problems. Some application modes or implementation modes (e.g., telemedicine) of some aspect examples are operated to provide a series of images (image group, image set) that represents a sufficiently wide area of an anterior eye segment with a slit lamp microscope directly or indirectly to a person who conducts image interpretation. Therefore, performing re-photographing is difficult even when the quality of a series of images provided is low, thus yielding, as a result, problematic cases such as the following events: image interpretation cannot be conducted at all; or only inadequate image interpretation can be conducted. Accordingly, acquisition of images with "satisfactory" quality "in advance" is required. More specifically, it is desired to collectively acquire a series of images having a quality that enables effective diagnosis (e.g., effective image interpretation) before providing the series of images to a person who conducts image interpretation. However, considering the occurrence of blinking and eye movements during photographing in addition to difficulty of operating slit lamp microscopes, it is extremely difficult to obtain a series of images that represents an entire target area for observation and image interpretation with satisfactory image quality.

The slit lamp microscope according to some aspect examples can be used to acquire a series of images (image group, image set) that represents a wide area of an anterior eye segment with satisfactory image quality. Further, the ophthalmic system according to some aspect examples can be used for telemedicine using such a slit lamp microscope.

Hereinafter, some aspect examples will be described. Any two or more of these aspect examples may be combined at least in part. Further, any modifications, such as additions, replacements, and/or omissions, on the basis of any known technique or technology, may be applied to such a combination.

At least one or more of the functions of the elements described in the present disclosure are implemented by using a circuit configuration (circuitry) or a processing circuit configuration (processing circuitry). The circuitry or the processing circuitry includes any of the following options, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), an existing or conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case in which the hardware is a processor, which may be considered as a certain type of circuitry, then circuitry, a unit, a means, or a term similar to these is a combination of hardware and software. In this case, the software is used to configure the hardware and/or the processor.

First Aspect Example

FIG. 1 shows an example of the slit lamp microscope according to the first aspect example.

The slit lamp microscope 1 may be used for photographing the anterior segment of the subject's eye E, and includes the illumination system 2, the photography system 3, the movement mechanism 6, the controller 7, the data processor 8, and the communication device 9. The cornea of the subject's eye E is denoted by the reference character C, and the crystalline lens is denoted by the reference character CL.

The slit lamp microscope 1 may be a single apparatus, or may also be a system that includes two or more apparatuses. In the case where the slit lamp microscope 1 is configured as a system, the slit lamp microscope 1 may include a main apparatus, a computer, and a communication device. Here, the main apparatus may include the illumination system 2, the photography system 3, and the movement mechanism 6, the computer may include the controller 7, the data processor 8, and the communication device 9, and the communication device may perform communication between the main apparatus and the computer. The computer may be installed together with the main apparatus, for example, or may also be installed on a network.

<Illumination System 2>

The illumination system 2 projects slit light onto the anterior segment of the subject's eye E. The reference character 2a denotes the optical axis of the illumination system 2 that is referred to as the illumination optical axis. The illumination system 2 may have the same or similar configuration as or to the illumination system of a conventional slit lamp microscope. For example, the illumination system 2 includes an illumination light source, a positive lens, a slit forming member, and an objective lens in the order from the side far from the subject's eye E (not shown in the drawings).

The illumination light source outputs (emits) illumination light. The illumination system 2 may include a plurality of illumination light sources. For example, the illumination system 2 may include both an illumination light source that outputs continuous light or steady light, and an illumination light source that outputs flash light. Further, the illumination system 2 may include both an illumination light source for anterior segment illumination and an illumination light source for posterior segment illumination. Furthermore, the illumination system 2 may include two or more illumination light sources with mutually different output wavelengths. A typical example of the illumination system 2 includes a visible light source as an illumination light source. The illumination system 2 may also include an infrared light source. The illumination light output from the illumination light source passes through the positive lens and is projected onto the slit forming member.

The slit forming member passes a part of the illumination light to generate slit light. A typical example of the slit forming member has a pair of slit blades. The width of the region through which the illumination light passes is changed by changing the interval between the slit blades, and the width of the slit light is changed accordingly. The region through which the illumination light passes is referred to as a slit, and the interval between the slit blades is referred to as a slit width. Further, the slit forming member may be configured to be capable of changing the length of the slit light. The length of the slit light is a size of a cross section of the slit light along the direction orthogonal to the cross sectional width direction of the slit light. Here, the cross sectional width direction corresponds to the slit width. The width of the slit light and the length of the slit light of some typical examples are represented as the size (dimensions) of a projected image on the anterior segment formed by the slit light; however, possible representations of the width and length of the slit light are not limited to these examples. For example, the width of the slit light and the length of the slit light may be represented as the size of the cross section of the slit light at a freely selected or determined position, or as the size of the slit formed by the slit forming member.

The slit light generated by the slit forming member is refracted by the objective lens and is projected onto the anterior segment of the subject's eye E.

The illumination system 2 may further include a focus mechanism configured for changing the focal position of the slit light. The focus mechanism may be configured to move the objective lens along the illumination optical axis 2a, for example. The movement of the objective lens may be carried out automatically and/or manually. Another focus mechanism may be configured to change the focal position of the slit light by: preparing and disposing a focusing lens at a position in the illumination optical axis 2a between the objective lens and the slit forming member; and moving the focusing lens along the illumination optical axis 2a.

Note that FIG. 1 is a top view. As shown in FIG. 1, the direction along the axis of the subject's eye E is defined as the Z direction in the present aspect example. Of the directions orthogonal to the Z direction, the left-right direction (or, the lateral direction) for the subject is defined as the X direction. The direction orthogonal to both the X direction and the Z direction is defined as the Y direction. In some typical examples, the X direction is the direction from one of the left eye and the right eye toward the other, and the Y direction is the direction parallel to the body axis of the subject (body axis direction).

<Photography System 3>

The photography system 3 is configured to perform photography of the anterior segment while the slit light from the illumination system 2 is being projected onto the anterior segment. The reference character 3a denotes the optical axis of the photography system 3 that is referred to as the photography optical axis. The photography system 3 of the present aspect example includes the optical system 4 and the image sensor 5.

The optical system 4 is configured to direct light coming from the anterior segment of the subject's eye E onto which the slit light is being projected, to the image sensor 5. The image sensor 5 includes a light detecting plane that receives the light directed by the optical system 4.

The light directed by the optical system 4, that is, the light coming from the anterior segment of the subject's eye E, contains return light of the slit light being projected onto the anterior segment, and may further contain other kinds of light. Examples of the return light include reflected light of the slit light, scattered light of the slit light, and fluorescence induced by the slit light. Examples of the other kinds of light include light from the environment in which the slit lamp microscope 1 is installed, such as indoor light (room light) and sunlight. In the case where another illumination system different from the illumination system 2 is provided as an anterior segment illumination system for illuminating the entire anterior segment, return light of the anterior segment illumination light emitted by the anterior segment illumination system may be contained in the light directed by the optical system 4.

The image sensor 5 may be an area sensor that has a two dimensional image detecting area. The image sensor 5 may be, for example, a charge-coupled device (CCD) image sensor, a complementary metal oxide semiconductor (CMOS) image sensor, or another type of image sensor.

The optical system 4 may have, for example, the same or similar configuration as or to the photography system of a conventional slit lamp microscope. For example, the optical system 4 includes an objective lens, a variable magnification optical system, and an imaging lens in the order from the side closer to the subject's eye E. The light coming from the anterior segment of the subject's eye E onto which the slit light is being projected, passes through the objective lens and the variable magnification optical system, and then forms an image on the light detecting plane of the image sensor 5 by the imaging lens.

The photography system 3 may include the first photography system and the second photography system, for example. In a typical example, the first photography system and the second photography system have the same configuration. The case in which the photography system 3 includes the first photography system and the second photography system will be described later as another aspect example.

The photography system 3 may further include a focus mechanism configured for changing the focal position of the photography system 3. The focus mechanism may be configured to move the objective lens along the photography optical axis 3a, for example. The movement of the objective lens may be carried out automatically and/or manually. Note that a focusing lens may be prepared and disposed at a position in the photography optical axis 3a between the objective lens and the imaging lens, and also the focus mechanism may be capable of moving the focusing lens along the photography optical axis 3a, thereby changing the focal position of the photography system 3.

The illumination system 2 and the photography system 3 function as a Scheimpflug camera. More specifically, the illumination system 2 and the photography system 3 are configured in such a manner that the subject plane along the illumination optical axis 2a, the optical system 4, and the light detecting plane of the image sensor 5 satisfy what is commonly referred to as the Scheimpflug condition. More specifically, the YZ plane passing through the illumination optical axis 2a (the YZ plane contains the subject plane), the principal plane of the optical system 4, and the light detecting plane of the image sensor 5 intersect on the same straight line. As a result of this, photographing can be performed with all positions in the subject plane in focus. In other words, photographing can be performed with all positions in the direction along the illumination optical axis 2a in focus.

The illumination system 2 and the photography system 3 of the present aspect example are configured in such a manner that at least an area defined by the anterior surface of the cornea C and the posterior surface of the crystalline lens CL is in focus of the photography system 3, for example. In other words, photography may be performed in a state in which the focus of the photography system 3 is on the entire area from the apex of the anterior surface of the cornea C (Z=Z1) to the apex of the posterior surface of the crystalline lens CL (Z=Z2) shown in FIG. 1. Note that the location Z=Z0 corresponds to the Z coordinate of the intersection of the illumination optical axis 2a and the photography optical axis 3a.

The condition described above is typically implemented by the configuration and arrangement of the elements included in the illumination system 2, the configuration and arrangement of the elements included in the photography system 3, and the relative positions between the illumination system 2 and the photography system 3. A parameter indicating the relative positions of the illumination system 2 and the photography system 3 may include the angle θ formed by the illumination optical axis 2a and the photography optical axis 3a, for example. The value of the angle θ may be set to 17.5 degrees, 30 degrees, or 45 degrees, for example. The angle θ may be variable.

<Movement Mechanism 6>

The movement mechanism 6 is configured to move the illumination system 2 and the photography system 3. The movement mechanism 6 includes, for example, a movable stage, an actuator, and a mechanism. The illumination system 2 and the photography system 3 are placed on the movable stage. The actuator is configured to operate in accordance with a control signal input from the controller 7. The mechanism is configured to receive driving force generated by the actuator and move the movable stage. In another example, the movement mechanism 6 may include a movable stage on which the illumination system 2 and the photography system 3 are placed, and a mechanism configured to receive force applied to an operation device (not shown in the drawings) and move the movable stage. The operation device is a lever, for example. The movable stage may be movable at least in the X direction and may be further movable in at least one of the Y direction and the Z direction.

The movement mechanism 6 of the present aspect example is configured to move the illumination system 2 and the photography system 3 together with each other in the X direction, for example. In other words, the movement mechanism 6 moves the illumination system 2 and the photography system 3 in the X direction while maintaining the state in which the above-mentioned Scheimpflug condition is satisfied. In parallel with this movement, the photography system 3 performs moving image photography at a predetermined time interval (photographing rate, acquisition rate), for example. As a result of this, a three dimensional area of the anterior segment of the subject's eye E is scanned with the slit light, and a plurality of images (an image group) corresponding to the plurality of cross sections in the three dimensional area are collected.

<Controller 7>

The controller 7 is configured to control each part of the slit lamp microscope 1. For example, the controller 7 controls elements of the illumination system 2 (e.g., illumination light source, slit forming member, focus mechanism, etc.), elements of the photography system 3 (e.g., focus mechanism, image sensor, etc.), the movement mechanism 6, the data processor 8, and the communication device 9, and so forth. Further, the controller 7 may be capable of executing a control for changing the relative positions of the illumination system 2 and the photography system 3.

The controller 7 includes a processor, a primary storage, a secondary storage, and so forth. The secondary storage retains a control program and so forth. The control program and so forth may be stored in a computer or a storage accessible by the slit lamp microscope 1. The function of the controller 7 is implemented by cooperation of software such as the control program and hardware such as the processor.

The controller 7 may be capable of applying the following controls to the illumination system 2, the photography system 3 and the movement mechanism 6 in order to scan a three dimensional area of the anterior segment of the subject's eye E with the slit light.

Figure 2A:
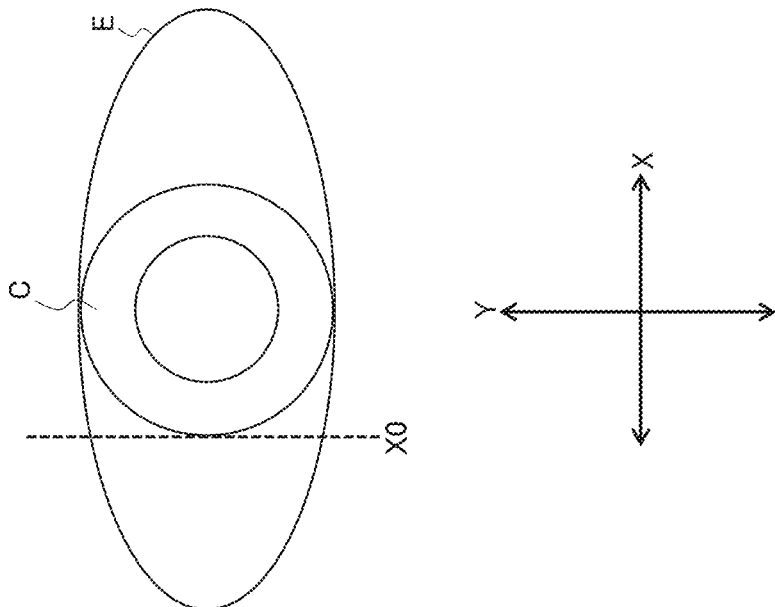
FIG. 2A is a schematic diagram for describing an operation of a slit lamp microscope according to an aspect example.
Figure 2B:
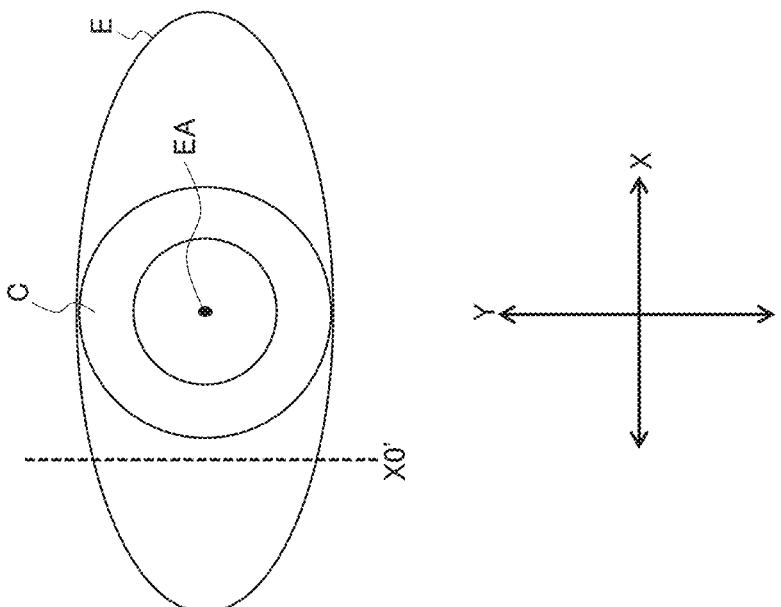
FIG. 2B is a schematic diagram for describing an operation of a slit lamp microscope according to an aspect example.

First, the controller 7 controls the movement mechanism 6 to place the illumination system 2 and the photography system 3 at a predetermined scan start position. This control is referred to as alignment control. The scan start position is, for example, a position corresponding to the edge position (first edge position) of the cornea C in the X direction, or a position further away from the axis of the subject's eye E than the first edge position. The reference character X0 shown in FIG. 2A denotes an example of a scan start position corresponding to the first edge position of the cornea C in the X direction. Further, the reference character X0' shown in FIG. 2B denotes an example of a scan start position further away from the axis EA of the subject's eye E than the position corresponding to the first edge position of the cornea C in the X direction.

The controller 7 controls the illumination system 2 to start the projection of the slit light onto the anterior segment of subject's eye E. This control is referred to as slit light projection control. The slit light projection control may be performed before the execution of the alignment control or during the execution of the alignment control. The slit light is typically continuous light, but the slit light may be intermittent light (pulse light). The turning on/off control of the pulse light is synchronized with the photographing rate of the photography system 3. The slit light is typically visible light, but the slit light may be infrared light or a mixture of visible light and infrared light.

The controller 7 controls the photography system 3 to start moving image photography (moving image acquisition) of the anterior segment of the subject's eye E. This control is referred to as photography control. The photography control may be performed before the execution of the alignment control or during the execution of the alignment control. In some typical examples, the photography control is executed simultaneously with the slit light projection control or after the slit light projection control.

After having executed the alignment control, the slit light projection control, and the photography control, the controller 7 performs a control of the movement mechanism 6 to start the movement of the illumination system 2 and the photography system 3. This control is referred to as movement control. The illumination system 2 and the photography system 3 are moved together by the movement control. In other words, the movement mechanism 6 moves the illumination system 2 and the photography system 3 while maintaining the relative positions (e.g., the angle θ) between the illumination system 2 and the photography system 3. In some typical examples, the movement mechanism 6 moves the illumination system 2 and the photography system 3 while maintaining the state in which the aforementioned Scheimpflug condition is satisfied. The movement of the illumination system 2 and the photography system 3 is performed from the aforementioned scan start position to a predetermined scan end position. The scan end position is, for example, a position corresponding to the edge position (second edge position) of the cornea C on the opposite side of the first edge position in the X direction, or a position further away from the axis of the subject's eye E than the second edge position, as in the scan start position. In such a case, the area from the scan start position to the scan end position becomes a scan area.

In some typical examples, the photography system 3 carries out the moving image photography in parallel with the projection of the slit light onto the anterior segment and the movement of the illumination system 2 and the photography system 3 in the X direction. Here, the width direction of the slit light corresponds to the X direction and the longitudinal direction of the slit light corresponds to the Y direction.

Here, the length of the slit light (that is, the size of the slit light in the Y direction) is set to be, for example, equal to or greater than the diameter of the cornea C on the surface of the subject's eye E. In other words, the length of the slit light is set to be equal to or greater than the corneal diameter in the Y direction. Further, the distance of the movement of the illumination system 2 and the photography system 3 carried out by the movement mechanism 6 (that is, scan area) is set to be equal to or greater than the corneal diameter in the X direction, as described above. As a result of setting the slit light length and the movement distance in these manners, an area including the entire cornea C can be scanned with the slit light.

Figure 3:
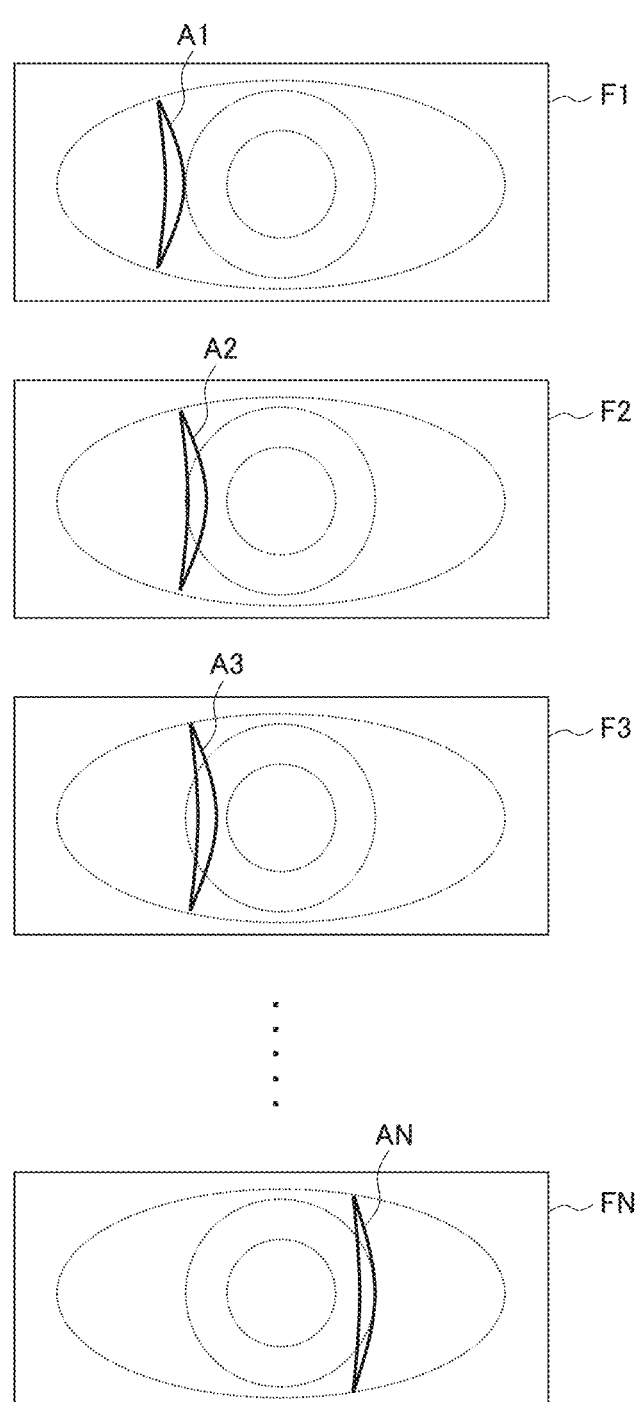
FIG. 3 is a schematic diagram for describing an operation of a slit lamp microscope according to an aspect example.

With such a scan, a plurality of anterior segment images corresponding to mutually different slit light projection positions is acquired. In other words, a moving image is obtained in which the state (aspect) of the movement of the slit light projection position in the X direction is depicted. FIG. 3 shows an example of such a plurality of anterior segment images, that is, an example of such a group of frames (a frame group) composing a moving image.

FIG. 3 shows the plurality of anterior segment images (the frame group, the image group) F1, F2, F3, . . . , and FN. The subscripts "n" of the anterior segment images Fn (n=1, 2, . . . , N) represent a time series order. In other words, the n-th anterior segment image acquired is represented by the reference character "Fn". The anterior segment image Fn includes the region onto which the slit light is being projected (slit light projected region) An. As shown in FIG. 3, the positions of the slit light projected regions A1, A2, A3, . . . , and AN shift to the right in time series order. The scan start position and the scan end position in the example shown in FIG. 3 correspond to both edge positions of the cornea C in the X direction. Possible scan start positions and/or possible scan end positions are not limited to the present example. The scan start position and/or the scan end position may be a position(s) further away from the axis of the subject's eye E than the edge position(s) of the cornea, for example. In addition, the direction of scans and the number of (times of) scans may be set accordingly.

<Data Processor 8>

The data processor 8 executes various kinds of data processing. Data to be processed may be either any data acquired by the slit lamp microscope 1 or any data input from the outside. For example, the data processor 8 can process images acquired by using the photography system 3. Note that the configuration examples and the function examples of the data processor 8 will also be described in other aspect examples in addition to the description of the present aspect example.

The data processor 8 includes a processor, a primary storage, a secondary storage, and so forth. The secondary storage retains a data processing program and so forth. The data processing program and so forth may include a model constructed by machine learning (learned model, inference model, etc.). The data processing program and so forth may be stored in a computer or a storage accessible by the slit lamp microscope 1. The function of the data processor 8 is implemented by cooperation of software such as the data processing program and hardware such as the processor.

Figure 4A:
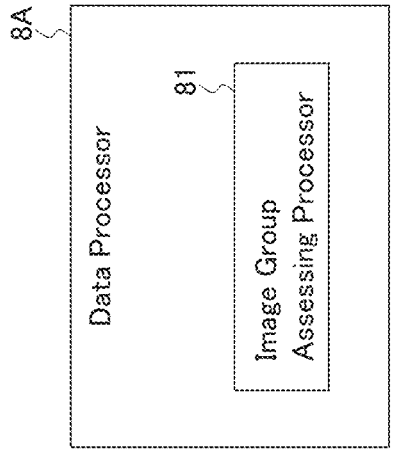
FIG. 4A is a schematic diagram illustrating a configuration of a slit lamp microscope according to an aspect example.
Figure 4B:
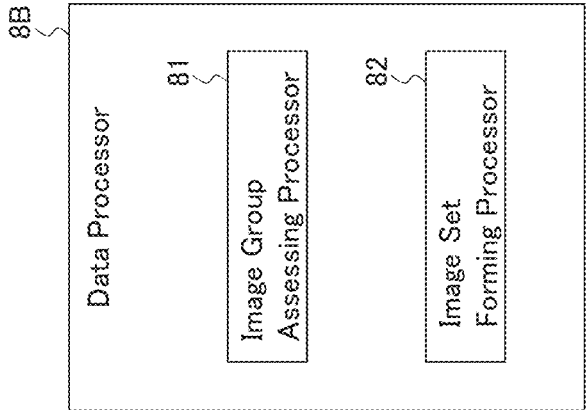
FIG. 4B is a schematic diagram illustrating a configuration of a slit lamp microscope according to an aspect example.
Figure 4C:
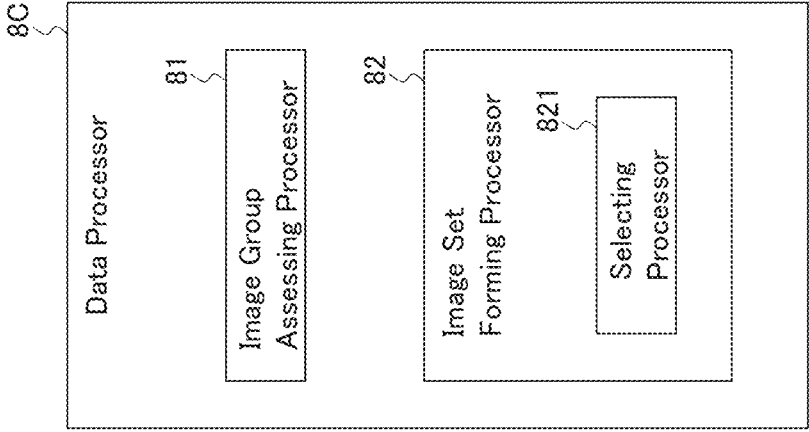
FIG. 4C is a schematic diagram illustrating a configuration of a slit lamp microscope according to an aspect example.
Figure 4D:
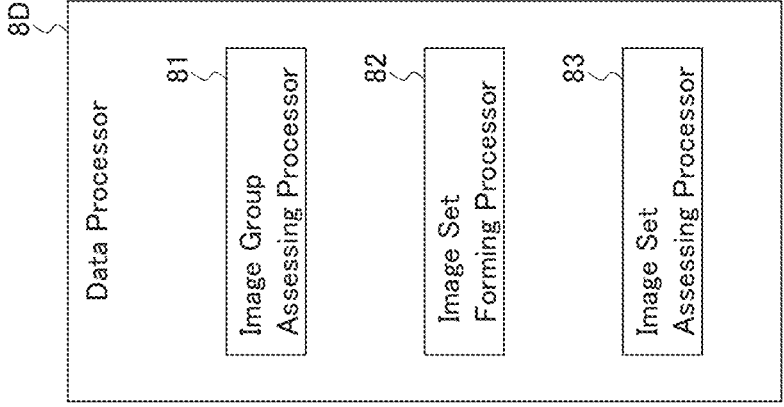
FIG. 4D is a schematic diagram illustrating a configuration of a slit lamp microscope according to an aspect example.

Some examples of the data processor 8 will be described. The data processor 8A shown in FIG. 4A, the data processor 8B shown in FIG. 4B, the data processor 8C shown in FIG. 4C, and the data processor 8D shown in FIG. 4D are the first, second, third, and forth examples of the data processor 8, respectively. Possible configurations of the data processor 8 are not limited to these examples. For example, the data processor 8 may include a combination of any two or more of the four data processors 8A, 8B, 8C, and 8D. The data processor 8 may also be provided with any element configured for obtaining the same or similar types of results.

The slit lamp microscope 1 of the present aspect example applies one or more times of scans to the anterior segment of the subject's eye E. Each scan generates an image group like the plurality of anterior segment images F1 to FN shown in FIG. 3. The data processor 8 may apply processing to one or more image groups acquired in this way.

The slit lamp microscope 1 may be capable of applying two or more times of scans to the anterior segment. For example, in the case where the first scan (the scan of the first time) does not yield a satisfactory image group, the second scan (the scan of the second time) is performed. More generally, in the case where all the first to the v-th scans (the scan of the v-th time) do not yield a satisfactory series of images, the (v+1)-th scan (the scan of the (v+1)-th time) is then performed (where v is an integer equal to or greater than 1). In some aspect examples, in the case where no satisfactory series of images (image set) is obtained from the v number of (pieces of) image groups acquired from the v number of (times of) scans of the first to the v-th scans, the (v+1)-th scan is then performed. In some other aspect examples, in the case where none of the v number of image groups acquired from the v number of scans of the first to the v-th scans is a satisfactory image set, the (v+1)-th scan is then performed. Note that the manner of conducting two or more times of scans is not limited to these example cases.

In the case where the slit lamp microscope 1 performs two or more times of scans, the start positions and the end positions (that is, scan areas) of the two or more times of scans may be the same, or one of or both the start positions and the end positions may be different. The two or more times of scans of some typical examples are aimed at the same scan area. Such scans acquire image groups, each of which is like the plurality of anterior segment images F1 to FN shown in FIG. 3. The number of the acquired image groups is equal to the number of scans.

Considering the eye movements of the subject's eye E and so forth, the scan area of some typical examples is defined by the operation of the slit lamp microscope 1 rather than positions or area in an anterior eye segment. For example, the start point of the movement of the illumination system 2 and the photography system 3 for a scan is determined to be a scan start position, and the end point of the movement of the illumination system 2 and the photography system 3 for a scan is determined to be a scan end position.

On the other hand, a scan area may be defined by positions or area in the anterior segment. In this case, the illumination system 2 and the photography system 3 are moved to follow the movement of the subject's eye E. This operation is referred to as tracking. The slit lamp microscope 1 of the present example has, for example, the same or similar tracking function as or to that of a conventional slit lamp microscope. The tracking function includes, for example, the following processes: a process of performing moving image photography of an anterior eye segment; a process of extracting a landmark from each frame; a process of calculating displacements (position shifts, positional differences, positional deviations) between frames using the landmarks; and a process of performing a movement control of the illumination system 2 and the photography system 3 to compensate for (to cancel, to eliminate) the displacements.

As another example of the definition (setting) of a scan area, a scan area may be set for images that have already been collected. In other words, setting of a scan area may be performed after scanning. A scan area in the present example is an area corresponding to images to be provided for subsequent processing.

A description will be given of the first example of such scan area determination after scanning. The slit lamp microscope of the present example is capable of performing anterior eye segment photography and recognizing the positional relationship between the optical system for anterior eye segment photography and the optical system for scanning (the illumination system 2 and the photography system 3). The present example begins with anterior eye segment photography, in parallel with acquisition of an image group (wide area image group) by scanning a sufficiently wide area of the anterior eye segment (particularly, sufficiently wide ranges in the X direction and the Y direction). Next, a scan area is determined for anterior segment images obtained by this anterior eye segment photography. This determination may be made manually or automatically. Automatic determination may include, for example, a process of analyzing an anterior segment image to detect a landmark (e.g., a pupil edge) and a process of determining a scan area with reference to the landmark. After the scan area determination, a partial area of each wide area image corresponding to the determined scan area is identified based on the positional relationship between the optical systems described above. Finally, by cropping the identified partial area from the wide area image, an image corresponding to the scan area is formed. With such processes, an image group corresponding to the determined scan area is obtained. When the fixation of the subject's eye is stable (or, when it is or can be assumed as such), anterior eye segment photography of the present example may be still image photography. When anterior eye segment photography of the present example is moving image photography, for example, association (correspondence, relationship) between a wide area image group and a frame group in the moving image is made based on control executed for scanning and moving image photography, such as based on synchronization information between scanning and moving image photography, and the same or similar processing as or to the above is executed for each pair of a wide area image and a frame associated with one another by the association.

The second example of scan area determination after scanning will be described. The present example does not require parallel anterior eye segment photography, and scans a sufficiently wide area of the anterior eye segment (particularly, sufficiently wide ranges in the X direction and the Y direction) to collect a wide area image group. Then, a partial area corresponding to a desired scan area is designated for each wide area image. This designation may be made manually or automatically. Automatic designation may include, for example, a process of analyzing a wide area image to detect a landmark (e.g., a corneal edge or a corner angle) and a process of determining a scan area with reference to the landmark. A landmark may be manually designated for one of the wide area images. This wide area image for which a landmark is designated is referred to as a reference wide area image. Then, the reference wide area image and a wide area image adjacent to the reference wide area image (adjacent wide area image) may be analyzed to designate a landmark for this adjacent wide area image. Sequential application of such processes gives landmarks for all the wide area images. Furthermore, partial areas of the wide area images corresponding to the scan area may be identified based on the landmarks, and images corresponding to the scan area may be obtained by cropping the identified partial areas from the respective wide area images. As a result of this, an image group corresponding to the determined scan area is obtained.

A description will be given of the first example of the data processor 8. The data processor 8A shown in FIG. 4A includes the image group assessing processor 81. The image group assessing processor 81 is configured to execute an assessment of a quality of an image group collected by a single scan of the anterior segment of the subject's eye E. In some aspect examples, the image group assessing processor 81 is configured to determine whether or not the image group satisfies a predetermined condition. In typical examples, the image group assessing processor 81 is configured to determine whether or not each image included in the image group satisfies a predetermined condition.

This predetermined condition (referred to as an image group assessment condition) is, for example, a condition relating to image quality required for effective performance of image interpretation and diagnosis. Examples of the image group assessment condition include a condition relating to the subject's eye E, a condition relating to the slit lamp microscope 1, a condition relating to the environment, and so forth. The image group assessment condition may include, for example, either one of or both the following condition items: a condition that an image to be assessed has not been affected by blinking (referred to as a blinking condition); and a condition that an image to be assessed has not been affected by eye movement (referred to as an eye movement condition). Further, the image group assessment condition may include any indicator relating to any image quality assessment and may include any of the following indicators: brightness; contrast; noise; signal-to-noise ratio (SNR); tone reproduction; dynamic range; sharpness; vignetting; aberrations (spherical aberration, astigmatism, comatic aberration, field curvature, distortion, chromatic aberration, etc.); color accuracy; exposure accuracy; lens flare; moire patterns; and artifacts. Possible image group assessment conditions are not limited to these examples, and may be determined and prepared optionally.

A description will be given of the blinking condition. For an image included in the image group, the image group assessing processor 81 performs determination whether or not a reflected image of the slit light projected onto the anterior segment of the subject's eye E is included in this image, for example. This determination is data processing carried out on the basis of a fact that a reflected image of the slit light is not depicted in an image taken during blinking and a fact that a reflected image of the slit light is represented significantly brighter than other areas. The determination is carried out, for example, based on the brightness distribution in an image being processed.

In some aspect examples, the image group assessing processor 81 generates a brightness histogram based on an image and then determines whether or not there is a pixel having brightness equal to or greater than a predetermined threshold value. When the image group assessing processor 81 determines that there is a pixel having brightness equal to or greater than the predetermined threshold value, it is determined that a reflected image of the slit light is included in this image. The present example has an advantage of being extremely simple to process, but it may falsely detect a high-brightness noise or a reflection of environment light (ambient light).

In some other aspect examples, the image group assessing processor 81 generates a brightness histogram based on an image and then determines whether or not there are a predetermined number or more of pixels having brightness equal to or greater than a predetermined threshold value. When the image group assessing processor 81 determines that the number of pixels having brightness equal to or greater than the predetermined threshold value is equal to or greater than the predetermined number, it is determined that a reflected image of the slit light is included in this image. The present example has an advantage that the above false detection can be prevented by simple processes as described above.

A description will be given of the eye movement condition. For an image included in the image group, the image group assessing processor 81 performs determination whether or not eye movement has affected this image by comparing this image with an image adjacent thereto, for example. This determination is data processing carried out on the basis of a fact that eye movement during moving image photography causes "skipping (lack, omission) of an image".

In some aspect examples, the image group assessing processor 81 detects a landmark from each of this image and the adjacent image, calculates the amounts of displacements (position shifts, positional differences, positional deviations) of the detected landmarks, and determines whether or not each of the displacement amounts calculated is equal to or greater than a predetermined threshold value. When the image group assessing processor 81 determines that the displacement amount(s) is equal to or greater than the predetermined threshold value, it is determined that eye movement has occurred. Here, the landmark may be, for example, a cornea, an iris, a pupil, a corner angle, or the like. The threshold value may be calculated based on a predetermined scanning condition such as the photographing rate of the photography system 3, the movement speed of the photography system 3 carried out by the movement mechanism 6, or the like.

In some other aspect examples, the image group assessing processor 81 may be configured to determine the presence or absence of eye movement from a single image. For example, when the photographing rate of the photography system 3 is low and high-speed eye movement occurs, "blurring" may occur in an image obtained. The image group assessing processor 81 may be configured to determine the presence or absence of eye movement by using a blur detection technique. Blur detection of some typical examples is performed using any known techniques such as edge detection.

The image group assessing processor 81 may include an artificial intelligence engine configured to determine whether or not an input image satisfies the image group assessment condition described above. In some typical examples, this artificial intelligence engine includes a convolutional neural network (CNN). This convolutional neural network has been trained in advance using training data. This training data may include a large number of images acquired with slit lamp microscopes and corresponding determination results of whether or not each of these images satisfies the image group assessment condition. Note that images included in the training data are not limited to images acquired with slit lamp microscopes. In some examples, any of the following images may be included in training data: an image acquired using other kinds of ophthalmic modalities (e.g., fundus camera, OCT apparatus, SLO, surgical microscope); an image acquired using any kinds of diagnostic imaging modalities of any clinical departments other than ophthalmology (e.g., ultrasonic diagnostic apparatus, X-ray diagnostic apparatus, X-ray computed tomography (CT) apparatus, magnetic resonance imaging (MRI) apparatus); an image generated by processing an actual image (image acquired from a living body); and a pseudo image. Further, the method and technique used in the artificial intelligence engine may be freely selected from among any known method and technique. For example, the type of hardware, the type of software, the type of machine learning method, and the type of neural network may be freely designed based on any known method and technique.

A series of images composing an image group collected by a single scan may be associated with a plurality of positions (a plurality of locations) in the scan area. This association is performed by the data processor 8, for example. A specific example will be explained. The scan area along the X direction is divided into the N−1 number of sections (intervals), the scan start position is determined at the first position, and the scan end position is determined at the N-th position. Here, N is an integer equal to or greater than 2. As a result, the N number of positions are determined in the scan area. The N number of positions are represented by B1, B2, B3, . . . , BN. It is now considered a case in which application of a single scan to the anterior segment of the subject's eye E has generated the image groups F1, F2, F3, . . . , FN shown in FIG. 3. The data processor 8 may assign the image Fn to the position Bn. As a result of this, the N number of images Fn (n=1, 2, . . . , N) respectively corresponding to the N number of positions Bn (n=1, 2, . . . , N) can be obtained.

An image group of some examples may include only such a series of images, or may include other information in addition to the series of images. Examples of information that may be included in an image group together with a series of images include various kinds of supplementary information (incidental information, ancillary information) such as subject information, subject's eye information, date and time of acquisition (photography), and acquisition conditions (photography conditions). An image group of some examples may include an image obtained by using another modality, examination data acquired by using an examination apparatus, or the like. Some examples of the configuration and the operation of the image group assessing processor 81 are described below with reference to FIG. 5A to FIG. 5D.

A description will be given of the second example of the data processor 8. The effectiveness of the present example is particularly demonstrated in the case where two or more times of scans are applied to the anterior segment of the subject's eye E. The data processor 8B shown in FIG. 4B includes the image set forming processor 82 in addition to the image group assessing processor 81 that is the same as or similar to that of FIG. 4A. The data processor 8B is provided with two or more image groups collected by two or more times of scans applied to the anterior segment of subject's eye E. The image group assessing processor 81 of the present example may execute a quality assessment of each of these image groups, or alternatively may execute a quality assessment of only an image group acquired by the first scan out of the two or more times of scans. The image set forming processor 82 is configured to execute a formation of an image set by selecting a series of images corresponding to a scan area from the two or more image groups input into the data processor 8B.

The series of images composing the image set may correspond to, for example, an area (of the anterior segment) to which any one of the two or more scans has been applied, or an area (of the anterior segment) determined based on scan areas of at least two of the two or more scans. As an example of the former, the maximum (largest) scan area or the minimum (smallest) scan area among the two or more scan areas to which the two or more scans have been respectively applied may be employed. As an example of the latter, the union set or the intersection set of the at least two scan areas may be employed.

The formed image set may include only the above-mentioned series of images corresponding to the scan area, or may include other information in addition to the series of images. Examples of information that may be included in the image set together with the series of images include various kinds of supplementary information (incidental information, ancillary information) such as subject information, subject's eye information, date and time of acquisition (photography), and acquisition conditions (photography conditions). The image set may also include an image obtained by using another modality, examination data acquired by using an examination apparatus, or the like.

A description will be given of the third example of the data processor 8. As in the second example, the effectiveness of the present example is particularly demonstrated when two or more times of scans are applied to the anterior segment of the subject's eye E. The data processor 8C shown in FIG. 4C includes both the image group assessing processor 81 configured in the same or similar manner to or as that of FIG. 4A and the image set forming processor 82 configured in the same or similar manner to or as that of FIG. 4B. However, the image set forming processor 82 of the present example includes the selecting processor 821.

The data processor 8C is provided with two or more image groups collected by two or more times of scans applied to the anterior segment of subject's eye E. The image group assessing processor 81 of the present example may execute a quality assessment of each of these image groups, or may execute a quality assessment of only the image groups acquired by the first scan. The image set forming processor 82 is configured to execute a formation of an image set by selecting a series of images corresponding to a scan area from the two or more image groups input into the data processor 8C. In this process of image set formation, the selecting processor 821 executes selection of images each of which satisfies a predetermined condition from the two or more image groups.

The predetermined condition (image selection condition) may be the same as or different from the image group assessment condition described above. In some examples in which the data processor 8C is configured in such a manner that the selecting processor 821 is provided with two or more image groups after the image group assessing processor 81 executes a quality assessment of each of the images, the selecting processor 821 may be configured to execute image selection in consideration of a condition relating to an image arrangement (image order, image sequence, etc.). Here, examples of such a condition include the blinking condition and the eye movement condition described above. Note that the image selection condition is not limited to these examples, and the relationship between the image group assessment condition and the image selection condition is also not limited to these examples.

Below, descriptions will be given of a case in which the selecting processor 821 takes the blinking condition into consideration and a case in which the selecting processor 821 takes the eye movement condition into consideration. In addition, for cases in which the selecting processor 821 takes into consideration a condition other than these two conditions, the selecting processor 821 may be configured to be capable of executing the same or similar processing as or to some specific examples regarding the image group assessing processor 81. These specific examples will be described later with reference to FIG. 5A to FIG. 5D.

A description will be given of image selection with the blinking condition taken into account. Note that the blinking condition is a condition for checking whether or not an image to be assessed has been affected by blinking. For an image included in the two or more image groups, the selecting processor 821 performs determination whether or not a reflected image of the slit light projected onto the anterior segment of the subject's eye E is included in this image, for example. This determination is data processing carried out on the basis of a fact that a reflected image of the slit light is not depicted in an image taken during blinking and a fact that a reflected image of the slit light is represented significantly brighter than other areas. The determination is carried out, for example, based on the brightness distribution in an image being processed.

In some aspect examples, the selecting processor 821 generates a brightness histogram based on an image and then determines whether or not there is a pixel having brightness equal to or greater than a predetermined threshold value. If the selecting processor 821 determines that there is a pixel having brightness equal to or greater than the predetermined threshold value, it is determined that a reflected image of the slit light is included in this image. The present example has an advantage of being extremely simple to process, but it may falsely detect a high-brightness noise or a reflection of environment light (ambient light).

In some other aspect examples, the selecting processor 821 generates a brightness histogram based on an image and then determines whether or not there are a predetermined number or more of pixels having brightness equal to or greater than a predetermined threshold value. If the selecting processor 821 determines that the number of pixels having brightness equal to or greater than the predetermined threshold value is equal to or greater than the predetermined number, it is determined that a reflected image of the slit light is included in this image. The present example has an advantage that the above false detection can be prevented by simple processes as described above.

A description will be given of image selection with the eye movement condition taken into account. Note that the eye movement condition is a condition for checking whether or not an image is to be assessed has been affected by eye movement. For an image included in the two or more image groups, the selecting processor 821 performs determination whether or not eye movement has affected this image by comparing this image with an image adjacent thereto, for example. This determination is data processing carried out on the basis of a fact that eye movement during moving image photography causes "skipping (lack, omission) of an image".

In some aspect examples, the selecting processor 821 detects a landmark from each of this image and the adjacent image, calculates the amounts of displacements (position shifts, positional differences, positional deviations) of the detected landmarks, and determines whether or not each of the displacement amounts calculated is equal to or greater than a predetermined threshold value. If the selecting processor 821 determines that the displacement amount(s) is equal to or greater than the predetermined threshold value, it is determined that eye movement has occurred. Here, the landmark may be, for example, a cornea, an iris, a pupil, a corner angle, or the like. The threshold value may be calculated based on a predetermined scanning condition such as the photographing rate of the photography system 3, the movement speed of the photography system 3 carried out by the movement mechanism 6, or the like.

In some other aspect examples, the selecting processor 821 may be configured to determine the presence or absence of eye movement from a single image. For example, when the photographing rate of the photography system 3 is low and high-speed eye movement occurs, "blurring" may occur in an image obtained. The selecting processor 821 may be configured to determine the presence or absence of eye movement by using a blur detection technique. The blur detection of some typical examples is performed by using any known techniques such as edge detection.

As in the case of the image group assessing processor 81, the selecting processor 821 may include an artificial intelligence engine configured to determine whether or not an input image satisfies the image selection condition described above.

The series of images included in the image set formed by the image set forming processor 82 may be associated with a plurality of positions (a plurality of locations) in the scan area. For example, the selecting processor 821 may be configured to perform selection of images in such a manner as to assign one or more images to each of the plurality of positions in the scan area.

A specific example will be explained. The scan area along the X direction is divided into N−1 number of sections (intervals), the scan start position is determined at the first position, and the scan end position is determined at the N-th position. Here, N is an integer equal to or greater than 2. As a result, N number of positions are determined in the scan area. The N number of positions are represented by B1, B2, B3, . . . , BN.

It is now considered a case in which a result of application of two or more times of scans to the anterior segment of the subject's eye E has generated the image groups F1, F2, F3, . . . , FN shown in FIG. 3. Note that in the description given above, the N number of images F1 to FN shown in FIG. 3 forms an image group obtained by a single scan. However, in the present document for the sake of simplicity of description, the N number of images F1 to FN shown in FIG. 3 may sometimes be treated as (used as) any image group (any plurality of images) to be considered. The same applies hereinafter. For example, in the description of the present example, the N number of images F1 to FN are treated as a series of images included in an image set.

For the N number of positions B1 to BN and the N number of images F1 to FN, the selecting processor 821 may assign the image Fn to the position Bn. As a result of this, the N number of images Fn (n=1, 2, . . . , N) respectively corresponding to the N number of positions Bn (n=1, 2, . . . , N) can be obtained, and then an image set can be formed with the image group Fn as "a series of images", for example.

In some aspect examples, if the image group assessing processor 81 has determined that the quality of an image group obtained by the first scan is not satisfactory, the second scan is then performed automatically or upon an instruction given by the user. If the number of scans applied to the anterior segment is two or more, the slit lamp microscope 1 performs an operation of applying the two or more times of scans to the anterior segment and an operation of selecting a series of images from two or more image groups collected by the two or more times of scans. Here, a way how to perform these operations (execution modes of these operations) may be freely selected or determined. In the first example thereof, the slit lamp microscope 1 may be configured to alternately execute (to execute by turns) application of a scan to the anterior eye segment and selection of an image from an image group acquired by this scan, in response to acquisition of an assessment result showing the quality of an image group obtained by the first scan is not satisfactory. In the second example, the slit lamp microscope 1 may be configured to perform two or more times of scans in a row and then select a series of images from two or more image groups collected by the two or more times of scans, in response to acquisition of an assessment result showing the quality of an image group obtained by the first scan is not satisfactory. These two examples will be described below. It should be noted that instead of or in addition to selection of an image from an image group(s), the image group assessing processor 81 may execute an assessment of an image group. As mentioned above, an image group assessment and image selection may be the same, similar, or interchangeable processes. In some aspect examples, any matters and items in a description of an image group assessment may be applied to image selection, and conversely, any matters and items in a description of image selection may be applied to an image group assessment.

The first example of the aspect (mode) of the scan application and the image selection performed after the image group assessing processor 81 has assessed that the quality of an image group obtained by the first scan is not satisfactory, is the alternate execution of the scan application and the image selection. More specifically, the first example is operated to repeat, a predetermined number of times, the pair of the application of a scan to the anterior eye segment and the selection of an image from an image group acquired by this scan, for example. In other words, the first example is operated to execute the U number of pairs of operations (here, U is an integer equal to or greater than 1) in the order of the first pair of operations (the scan application and the image selection), the second pair of operations (the scan application and the image selection), . . . , and the U-th pair of operations (the scan application and the image selection). Further, the pair of the first scan performed before this alternate execution and the quality assessment of the image group obtained by the first scan (by the image group assessing processor 81) will be referred to as the 0-th pair of operation.

Here, the number of scans in the u-th pair may be any number of times equal to or greater than 1 (u=0, 1, . . . , U). Further, the number of scans in the $u_1$-th pair and the number of scans in the $u_2$-th pair may be equal to or different from each other (here, $u_1$=0, 1, . . . , U; $u_2$=0, 1, . . . , U; $u_1 \neq u_2$).

In the first example, the selecting processor 821 may be configured to form a tentative image set (provisional image set, temporary image set, interim image set) by selecting two or more images from two or more image groups collected by two or more times of scans already performed. In other words, the slit lamp microscope 1 may be configured to form, at any point of time during the alternate execution of the scan application and the image selection, a tentative image set from two or more image groups obtained by two or more times of scans that have been performed up to this point of time. For example, the selecting processor 821 may be configured to form a tentative image set from all images obtained by the 0-th to the u-th pairs after the scan in the u-th pair has been performed. With such a configuration, the slit lamp microscope 1 is capable of forming a tentative image set from two or more image groups obtained up to the present point of time for the purpose of constructing a final image set.

In the case where the configuration described above is employed for forming a tentative image set, the following configuration may be combined with the configuration described above. Immediately after another scan is applied to the anterior segment of the subject's eye E, the selecting processor 821 first selects one or more images from another image group collected by this another scan. Subsequently, the selecting processor 821 forms another tentative image set (new tentative image set) by adding the one or more images selected from this another image group to a tentative image set that has been formed based on one or more scans performed prior to this another scan. For example, after the scan in the (u+1)-th pair have been performed, the selecting processor 821 may first select one or more images from an image group obtained by the (u+1)-th pair. Further, the selecting processor 821 may form another tentative image set by adding the one or more image selected from the image group obtained in the (u+1)-th pair to a tentative image set formed based on the image group(s) obtained by the 0-th to the u-th pairs. With such a configuration, each time a scan is applied to the anterior segment, the selecting processor 821 can sequentially update a tentative image set based on an image group obtained by this scan. This makes it possible to construct a final image set reliably and efficiently.

In the case where the configuration described above is employed for forming (and updating) a tentative image set, the following configuration may be combined with the configuration described above. The controller 7 (or the image set forming processor 82 (the selecting processor 821)) includes an image number counter configured to count the number of images included in a tentative image set. The controller 7 controls the scanner (the illumination system 2, the photography system 3, the movement mechanism 6) and the selecting processor 821 to terminate the alternate execution of the scan application and the image selection when the number of images included in the tentative image set reaches a predetermined number. Here, the predetermined number is the number of a series of images included in a final image set, and may be determined in advance or from a status of processing. Further, the controller 7 makes determination as to whether or not the number of images included in the tentative image set has reached the predetermined number. This determination may include only a process of comparing the number of images. Alternatively, in the case where a plurality of positions in the scan area and a series of images are associated with each other (described above), the controller 7 may determine whether or not a corresponding image has been assigned to every one of the plurality of positions. With such a configuration, the alternate execution of the scan application and the image selection can be automatically terminated upon obtaining the required number of images for a final image set.

In the case where the configuration described above is employed for forming (and updating) a tentative image set, the following configuration can be further combined with the configuration described above. The controller 7 includes a repetition counter configured to count the number of (times of) repetitions of the alternate execution of the scan application and the image selection. The repetition counter may be configured to count the number of the repetitions of the alternate execution by counting the number of repetition of the pair of the scan application and the image selection (the first pair to the U-th pair), or by counting the number of repetition of the scan application. The controller 7 controls the scanner (the illumination system 2, the photography system 3, the movement mechanism 6) and the selecting processor 821 to terminate the alternate execution of the scan application and the image selection when the number of the repetitions in the alternate execution reaches a predetermined number. In the case where the number of the repetitions is defined in units of the pair of the scan application and the image selection, the predetermined number is equal to the total number (U+1) of the pairs determined in advance. In the case where the number of the repetitions is defined in units of the number of the scan application, the predetermined number is equal to the total number of the scan application determined in advance. Further, the controller 7 makes determination as to whether or not the number of the repetitions has reached the predetermined number. With such a configuration, the scan application and the image selection can be automatically terminated at the stage where the scan application and the image selection have been repeated the number of times determined in advance. In the case where such a configuration is not employed, the scan application and the image selection are repeated until the number of images required to construct a final image set are selected, which causes fatigue to the subject and reduces photographing efficiency. In particular, when photographing a plurality of subjects in sequence, the throughput of the photographing is greatly impaired.

As described above, the present aspect example may be configured to automatically terminate the alternate execution of the scan application and the image selection. Possible conditions for such automatic termination are not limited to the two examples described above. For example, a condition for automatic termination may be an instruction input from a user. An alternative example may be configured to measure the elapsed time from the start of the alternate execution of the scan application and the image selection and terminate the alternate execution when the measured elapsed time reaches a predetermined time. Note that in the case where the repetition rate of the scan application and the image selection is constant, the automatic termination control based on the elapsed time is equivalent to the automatic termination control based on the number of the repetitions described above. The image set forming processor 82 may form an image set based on a tentative image set that has been saved at the point of time of termination of the alternate execution of the scan application and the image selection. The tentative image set is included in the image set, for example, as a series of images corresponding to the scan area. Predetermined subject information such as subject ID, official ID, name, age, gender, etc. is separately input into the slit lamp microscope 1. The image set forming processor 82 may be configured to form an image set by generating a supplementary information of a series of images including such subject information, subject's eye information (e.g., information indicating left eye/right eye), date and time of acquisition, acquisition conditions, etc. Further, the image set may also include other images obtained with the slit lamp microscope 1, images obtained with other modalities, examination data acquired with examination apparatuses, or the like. This concludes the description of the first example of the execution mode of the scan application and the image selection. A specific example of processing according to the present example will be described later.

Next, the second example of the aspect (mode) of the scan application and the image selection performed after the image group assessing processor 81 has assessed that the quality of an image group obtained by the first scan is not satisfactory will be described. In the present example, the slit lamp microscope 1 is configured to perform two or more times of scans in a row and then select a series of images from two or more image groups collected by the two or more times of scans. Then, an image is selected from the two or more image groups collected by the two or more times of scans and the image group obtained by the first scan performed prior to the two or more times of scans, and an image set that includes a series of images selected in this way is formed.

A specific example of such an operation will be described. To begin with, the selecting processor 821 generates an association (correspondence, relationship) between an image group corresponding to each scan and a plurality of positions in the scan area (described above). With this association, two or more images corresponding to different scans are assigned to each of the plurality of positions in the scan area.

Subsequently, for each position of the plurality of positions in the scan area, the selecting processor 821 selects one image from the two or more images that have been assigned to this position. The image selection condition employed in the present example may be, for example, the blinking condition and the eye movement condition described above. With this, one image is assigned to each of the plurality of positions in the scan area. A plurality of images respectively associated with the plurality of positions in this way is used as a series of images included in an image set. This concludes the description of the second example of the execution mode of the scan application and the image selection.

The fourth example of the data processor 8 will be described. As in the second and third examples, the effectiveness of the present example is particularly demonstrated in the case where two or more times of scans are applied to the anterior segment of the subject's eye E. The data processor 8D shown in FIG. 4D includes the image set assessing processor 83 in addition to the image group assessing processor 81, which is the same as or similar to that of FIG. 4A, and the image set forming processor 82, which is the same as or similar to that of FIG. 4B or 4C.

The image set assessing processor 83 is configured to execute an assessment of a quality of an image set formed by the image set forming processor 82. This quality assessment is a process of determining whether or not an image set has sufficient quality to effectively conduct diagnosis (image interpretation), and an assessment item and an assessment criterion are determined from this viewpoint. The assessment item and the assessment criterion may be common to one or more of the above-described image group assessment conditions and/or one or more of the above-described image selection conditions; however, the assessment item and the assessment criterion are not limited thereto.

The image set assessing processor 83 may be configured to execute different assessment processes depending on the types (aspects, modes) of image sets. For example, an assessment process applied to an image set formed in the case where the number of images included in a tentative image set has reached a predetermined number and an assessment process applied to an image set formed in the case where the number of the repetitions in the alternate execution of the scan application and the image selection has reached a predetermined number, may be different from each other. Note that the same assessment process may be applied regardless of the types of image sets.

Examples of an image set quality assessment include, in addition to an assessment of the quality of each image (which may be the same as or similar to an assessment of an image group), an assessment of an "arrangement order" of a series of images, an assessment of "skipping (lack, omission) of an image", and an assessment of "misalignment". Defects in an image set, such as disorder in the arrangement order, skipping (lack, omission) of an image, misalignment, etc., are caused by eye movement, fixation shift (fixation deviation), or the like.

The assessment of the arrangement order of a series of images will be described. In some aspect examples, the above-mentioned correspondence (one-to-one correspondence) between a series of images and a plurality of positions in a scan area is determined and prepared in advance. The image set assessing processor 83 may execute an arrangement order assessment using this correspondence.

Here, the plurality of positions in the scan area is ordered in accordance with their positional relationships in the real space. An example will be described now. As described above, the scan area along the X direction is divided into the N−1 number of sections, and the N number of positions B1, B2, B3, . . . , BN are set in order from the scan start position to the scan end position. In other words, the N number of positions B1 to BN are ordered in accordance with their positional relationships in the real space. In addition, a one-to-one correspondence is given between the N number of images F1 to FN (a series of images) and the N number of positions B1 to BN.

Under such conditions, the image set assessing processor 83 arranges the N number of images F1 to FN in accordance with the arrangement order (relative positional relationships) of the N number of positions B1 to BN, for example. This arrangement processing may be implemented by, for example, determining the coordinates of the N number of positions B1 to BN in a given three dimensional coordinate system, and arranging (embedding) the N number of images F1 to FN in the three dimensional coordinate system in accordance with the N number of coordinates determined. More specifically, the image set assessing processor 83 of some aspect examples may be configured to extract the slit light projected regions A1 to AN from the N number of images F1 to FN, respectively. Here, the slit light projected regions A1 to AN are two dimensional cross sectional images. The image set assessing processor 83 of the aspect examples further determines the coordinates of the N number of positions B1 to BN in the three dimensional coordinate system, and then executes a process of embedding the N number of two dimensional cross sectional images A1 to AN into the three dimensional coordinate system in accordance with the N number of coordinates determined.

The image set assessing processor 83 may be configured to analyze the images F1 to FN (the two dimensional cross sectional images A1 to AN) embedded in the three dimensional coordinate system to execute an assessment of whether or not their arrangement order is appropriate. In some aspect examples, the image set assessing processor 83 may be configured to detect a region of interest from the images F1 to FN (the two dimensional cross sectional images A1 to AN) and execute an assessment based on the morphology (e.g., connectivity (connectedness), continuity, etc.) of the region of interest in the arrangement direction of the images F1 to FN (the two dimensional cross sectional images A1 to AN). Here, the arrangement direction of the images F1 to FN is the X direction in the present example, and the region of interest is an image region corresponding to a site of interest such as the anterior surface of the cornea, the posterior surface of the cornea, the iris, the pupil, the anterior surface of the crystalline lens, the posterior surface of the crystalline lens, or the like. For example, if there exists a gap of the size equal to or larger than a predetermined size in the region of interest, the arrangement order is determined to be inappropriate, or it is determined that there is a change (replacement, swapping) in the arrangement order.

In some other aspect examples, the image set assessing processor 83 may be configured to construct a cross sectional image along the X direction, from the images F1 to FN (the two dimensional cross sectional images A1 to AN) embedded in the three dimensional coordinate system. In addition, the image set assessing processor 83 may be configured to execute an assessment based on the morphology (e.g., connectivity, continuity, etc.) of this cross sectional image constructed.

The assessment of skipping (lack, omission) of an image and the assessment of misalignment may be executed in the same manner as the arrangement order assessment described above.

As with the image group assessing processor 81 and the selecting processor 821, the image set assessing processor 83 may include an artificial intelligence engine configured to execute an assessment whether or not an input image set has sufficient quality for effective diagnosis.

A further specific example of image set assessment will be described in the second aspect example.

The controller 7 may be configured to execute a control of the communication device 9 to transmit an image set when the image set assessing processor 83 assesses that the quality of this image set is satisfactory. For example, the controller 7 prepares transmission information including such an image set, and then controls the communication device 9 to transmit this transmission information to a predesignated external device.

Possible modes or aspects of outputting an image set (and other information) from the slit lamp microscope 1 are not limited to transmission. Examples of output modes other than transmitting include storing in a storage (e.g., database), recording on a recording medium, printing on a printing medium, and so forth.

The controller 7 may be configured to perform a control to acquire another image set when the image set assessing processor 83 assesses that the quality of the image set is not satisfactory. For example, the controller 7 may be configured to display predetermined output information and/or perform audio (voice) output of predetermined output information. The predetermined output information may include contents for prompting the user to re-perform photography, for example, contents indicating that the performed photography (acquisition, image acquisition) was unsuccessful, or that re-photographing is necessary.

In some other aspect examples, the controller 7 may be configured to send a command to at least the scanner (the illumination system 2, the photography system 3, the movement mechanism 6) and the image set forming processor 82 in order to automatically start re-photographing (re-execution of scan application and image set formation).

<Communication Device 9>

The communication device 9 performs data communication between the slit lamp microscope 1 and another apparatus. In other words, the communication device 9 performs transmission of data to another apparatus and reception of data transmitted from another apparatus.

The system or method of the data communication executed by the communication device 9 may be selected accordingly. For example, the communication device 9 may include any one or more of various kinds of communication interfaces such as a communication interface conforming to the Internet, a communication interface conforming to a dedicated line, a communication interface conforming to a local area network (LAN), and a communication interface conforming to near field communication. The data communication may include any one of or both wireless communication and wired communication.

Data sent and received by the communication device 9 may be encrypted. If this is the case, for example, any one of or both the controller 7 and the data processor 8 include(s) at least one of an encryptor and a decryptor. The encryptor is configured to encrypt data to be sent by the communication device 9. The decryptor is configured to decrypt data having been received by the communication device 9.

<Image Group Assessing Processor 81>

Several examples of the image group assessing processor 81 are described with reference to FIG. 5A to FIG. 5D. Note that the image group assessing processor 81 is not limited to these examples, and any modifications, such as additions, replacements, and/or omissions, are possible. In addition, any two or more of these examples and modifications may be combined at least in part.

Figure 5A:
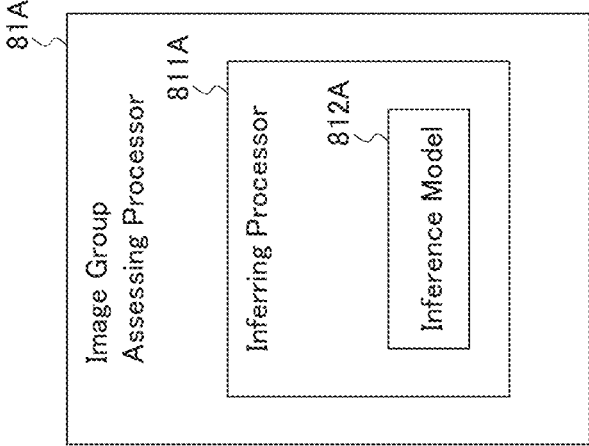
FIG. 5A is a schematic diagram illustrating a configuration of a slit lamp microscope according to an aspect example.

The first example of the image group assessing processor 81 will be described with reference to FIG. 5A and FIG. 5B.

The present example utilizes artificial intelligence technology to execute a quality assessment of an image group. The image group assessing processor 81A shown in FIG. 5A includes the inferring processor 811A configured to execute a quality assessment of an image group using the inference model 812A.

The inference model 812A is constructed in advance by using machine learning with training data including a plurality of anterior segment images. The device for constructing the inference model 812A (inference model construction device) may be disposed in the slit lamp microscope 1 (the data processor 8, etc.), or in a peripheral device (a peripheral computer or the like) of the slit lamp microscope 1. Alternatively, the inference model construction device may be a computer other than the peripheral computer.

Figure 5B:
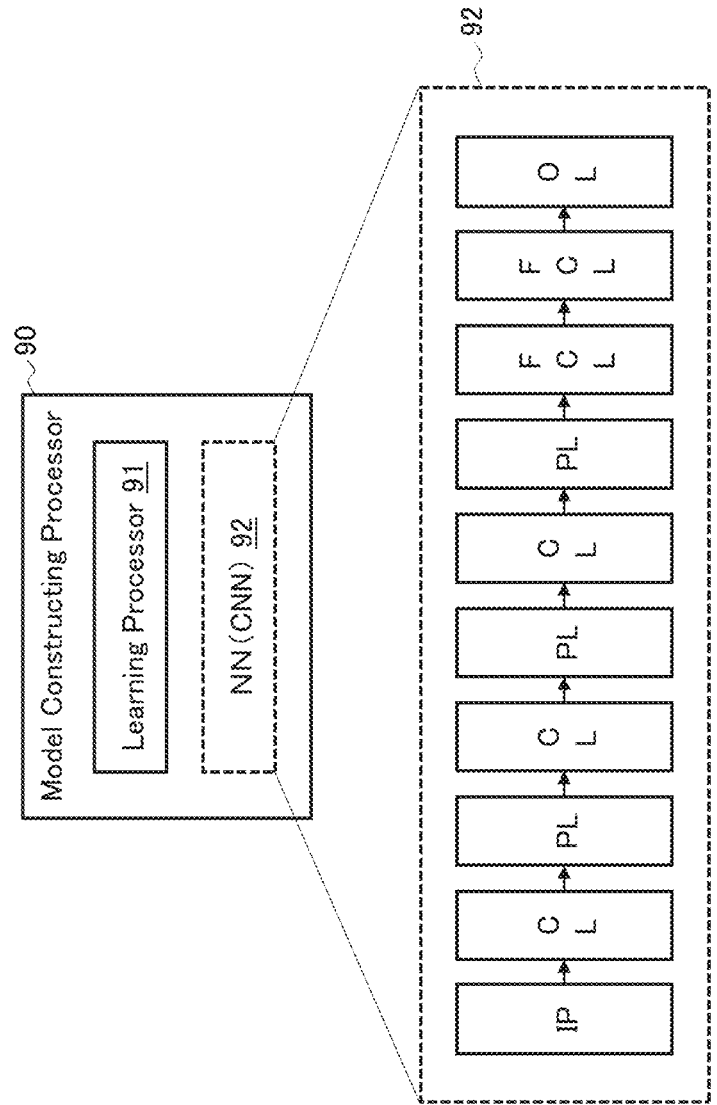
FIG. 5B is a schematic diagram for describing construction of an inference model for a slit lamp microscope according to an aspect example.

The model constructing processor 90 shown in FIG. 5B is an example of the inference model construction device, and is provided in the slit lamp microscope 1 or in its peripheral device. The model constructing processor 90 includes the learning processor 91 and the neural network 92.

In some typical examples, the neural network 92 includes a convolutional neural network (CNN). FIG. 5B shows an example of the structure of this convolutional neural network.

An image is input into the input layer of the neural network 92. Behind the input layer, a plurality of pairs of a convolutional layer and a pooling layer is disposed. While three pieces of pairs of a convolution layer and a pooling layer are provided in the neural network 92 shown in FIG. 5B, the number of the pairs may be freely selected or determined.

In the convolutional layer, a convolution operation is performed to detect or extract a feature (e.g., contour) from the input image. This convolution operation is a multiply-accumulate operation (a multiply-add operation, a product-sum operation) on the input image. This multiply-accumulate operation is performed with a filter function (a weight coefficient, a filter kernel) having the same dimension as the input image. In the convolutional layer, the convolution operation is applied to individual parts (individual sections, individual portions) of the input image. More specifically, the convolutional layer is configured to calculate a product by multiplying the value of each pixel in a partial image, to which the filter function has been applied, by the value (weight) of the filter function corresponding to this pixel, and then calculate the sum of the products over a plurality of pixels in this partial image. The sum of products obtained in this way is substituted for the corresponding pixel in an image to be output from the convolutional layer. By repetitively performing such multiply-accumulate operation in parallel with moving sites (parts) to which the filter function is applied (that is, in parallel with changing or switching partial images of the input image), a result of the convolution operation for the entire input image is obtained. The convolution operation performed in this way gives a large number of images in which various features have been extracted using a large number of weight coefficients. This means that a large number of filtered images, such as smoothed images and edge images, are obtained. The large number of images generated by the convolutional layer are referred to as feature maps (or activation maps).

The pooling layer executes data compression (e.g., data thinning) of the feature maps generated by the convolutional layer disposed at the immediately preceding position. More specifically, the pooling layer calculates statistical values in predetermined neighboring pixels of a predetermined pixel of interest in an input feature map at each predetermined pixel intervals, and outputs an image having a size smaller than the input feature map. The statistical values applied to the pooling operation may be maximum values (max pooling) or average values (average pooling), for example. The value of the pixel intervals applied to the pooling operation is referred to as a stride.

In general, a convolutional neural network extracts many features from an input image by executing processing using a plurality of pairs of a convolutional layer and a pooling layer.

A fully connected layer is disposed behind the most downstream pair of a convolutional layer and a pooling layer. While two pieces of fully connected layers are provided in the example shown in FIG. 5B, the number of fully connected layers may be freely selected or determined. The fully connected layer executes processing such as image classification, image segmentation, or regression using the features compressed by the combination of convolution and pooling. An output layer is disposed behind the most downstream fully connected layer. The output layer gives an output result.

Some aspect examples may employ a convolutional neural network including no fully connected layer. For example, some aspect examples may employ a fully convolutional network (FCN). Some aspect examples may include a support vector machine, a recurrent neural network (RNN), or any other models. Further, machine learning applied to the neural network 92 may be transfer learning. In other words, the neural network 92 may include a neural network that has already been trained using other training data (training images) and whose parameters have been adjusted (tuned). Further, the model constructing processor 90 (the learning processor 91) may be configured in such a manner that fine tuning can be applied to a trained neural network (at least part of the neural network 92). The neural network 92 may be constructed, for example, using a known open source neural network architecture.

The learning processor 91 applies machine learning with training data to the neural network 92. In the case in which the neural network 92 includes a convolutional neural network, parameters tuned by the learning processor 91 include, for example, filter coefficients of one or more convolutional layers therein and connection weights and offsets of one or more fully connected layers therein.

The training data of the present example at least includes a plurality of anterior segment images, as described above. The plurality of anterior segment images in some typical examples is images acquired by a slit lamp microscope but is not limited thereto. In some examples, the plurality of anterior segment images may include any of the following images: an image acquired using other kinds of ophthalmic modalities (e.g., fundus camera, OCT apparatus, SLO, surgical microscope); an image acquired using any kinds of diagnostic imaging modalities of any clinical departments other than ophthalmology (e.g., ultrasonic diagnostic apparatus, X-ray diagnostic apparatus, X-ray computed tomography (CT) apparatus, magnetic resonance imaging (MRI) apparatus); an image generated by processing an actual image (image acquired from a living body); and a pseudo image. Further, the number of pieces of training data may be increased by using any technique such as data augmentation.

The method and technique of training employed for constructing the inference model may be freely selected from among any known method and technique, or may be freely designed based on any known method and technique. In some examples, the method and technique of the training may be any of supervised learning, unsupervised learning, and reinforcement learning. In some alternative examples, the method and technique of the training may be any combination of any two or more of supervised learning, unsupervised learning, and reinforcement learning.

In some aspect examples, supervised learning is conducted on the basis of training data in which a label as a final output is assigned to each input image. For example, to each of a plurality of anterior segment images included in the training data, a label is attached in advance, representing whether or not image interpretation of the corresponding image is possible. Labels may be generated by, for example, a doctor or other inference models. The learning processor 91 of the present example may be configured to construct the inference model 812A by applying supervised learning using such training data to the neural network 92.

The inference model 812A of the present example constructed in this way is a trained model (learned model) configured to receive an input of an image obtained by scanning the anterior segment with slit light, and to generate an output of a possibility of image interpretation. Note that a possibility of image interpretation, which is an output of the inference model 812A, may be a freely selected or determined type of parameter that shows whether or not an image group to be assessed is suitable for image interpretation. In some examples, a possibility of image interpretation may include any of the following options: a result of a determination (judgement) of whether image interpretation is possible or impossible; a probability of image interpretation being able to be conducted; a validity (e.g., accuracy, precision) of a result obtained by conducting image interpretation, and so forth.

In order to prevent the overconcentration of processes in a specific unit of the neural network 92, the learning processor 91 may randomly select and invalidate one or more units and execute learning using the remaining units. Such a function is referred to as dropout.

The methods and techniques used for inference model creation are not limited to the examples shown above. In some examples, any methods and techniques such as the following options may be employed for creating an inference model: support vector machine, Bayes classifier, boosting, k-means clustering, kernel density estimation, principal component analysis, independent component analysis, self-organizing map (or self-organizing feature map), random forest (or randomized trees, random decision forests), and generative adversarial network (GAN).

Using the inference model 812A as described above, the inferring processor 811A shown in FIG. 5A executes an assessment of a quality of an image group collected by a single scan of the anterior segment of the subject's eye E. More specifically, first, the inferring processor 811A inputs an image group or each image included in the image group into the inference model 812A. In response to this input, the inference model 812A derives information representing image interpretation possibility from the image group or the corresponding image included in the image group.

The inferring processor 811A may use the interpretation possibility information output from the inference model 812A as it is as an inference result, or may generate an inference result on the basis of the interpretation possibility information. As an example of the latter, the inferring processor 811A may generate information for display from the interpretation possibility information, or may execute predetermined statistical processing.

Figure 5C:
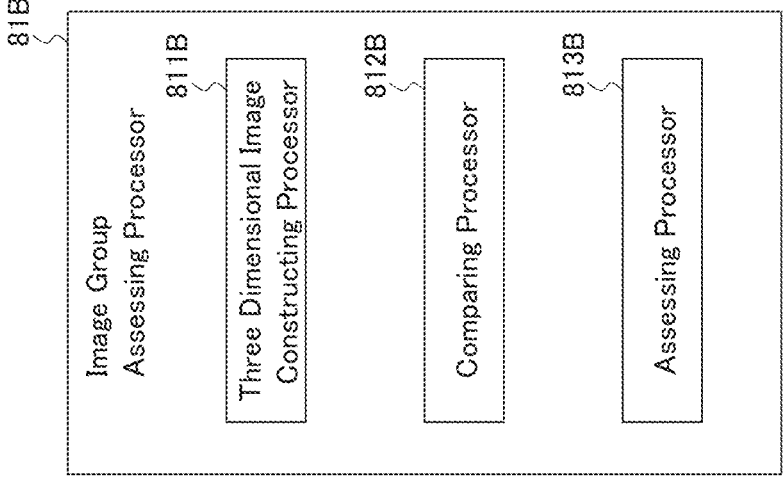
FIG. 5C is a schematic diagram illustrating a configuration of a slit lamp microscope according to an aspect example.

The second example of the image group assessing processor 81 will be described with reference to FIG. 5C. The present example transforms an image group into a three dimensional image and then executes a quality assessment. The image group assessing processor 81B shown in FIG. 5C includes the three dimensional image constructing processor 811B, the comparing processor 812B, and the assessing processor 813B.

The three dimensional image constructing processor 811B is configured to execute construction of a three dimensional image from an image group collected by a single scan of the anterior segment of the subject's eye E. For example, the three dimensional image constructing processor 811B may be configured to construct stack data by embedding an image group in a single three dimensional coordinate system. This stack data is constructed, for example, by embedding the N number of two dimensional cross sectional images A1 to AN shown in FIG. 3 into a three dimensional coordinate system in accordance with the arrangement order (relative positional relationships) of the N number of positions B1 to BN mentioned above.

The three dimensional image constructing processor 811B may be configured to apply a voxelization process to stack data constructed from an image group to construct volume data. In addition, the three dimensional image constructing processor 811B may apply a predetermined rendering process to stack data or volume data. Examples of the rendering process include volume rendering and surface rendering.

The comparing processor 812B is configured to execute a comparison between the three dimensional image (stack data, volume data, rendered image, etc.) constructed by the three dimensional image constructing processor 811B and a predetermined reference three dimensional image. The number of prepared reference three dimensional images is one or more and freely selected or determined.

The reference three dimensional image may include one or more reference three dimensional images corresponding to normal eyes. A reference three dimensional image corresponding to a normal eye may be, for example, an image acquired by performing photography of the normal eye which is an eye with no disease diagnosed and is also referred to as a healthy eye. An imaging modality employed for acquiring this reference three dimensional image may be freely selected or determined. In some typical examples, the imaging modality is the slit lamp microscope 1 or a slit lamp microscope having the same or similar configuration as or to the slit lamp microscope 1. In addition, the reference three dimensional image corresponding to a normal eye may be either of the following images: an image acquired by performing photography of a model of a normal eye (such as an eye model); or an image generated by computer graphics based on a model of a normal eye or a clinical example.

The reference three dimensional image may include one or more reference three dimensional images corresponding to an eye with a disease (affected eye). A reference three dimensional image corresponding to an eye with a disease may be, for example, an image acquired by performing photography of an eye in which a definitive diagnosis of a specific disease has been made. While an imaging modality for acquiring such a reference three dimensional image may be freely selected or determined, a typical example of the imaging modality is the slit lamp microscope 1 or a slit lamp microscope having the same or similar configuration as or to the slit lamp microscope 1. In addition, a reference three dimensional image corresponding to an eye with a disease may be either of the following options: an image acquired by performing photography of a model of an eye with a disease (such as an eye model); or an image generated by computer graphics based on a model of an eye with a disease or a clinical example.

The comparing processor 812B is configured to execute image matching between the three dimensional image constructed by the three dimensional image constructing processor 811B and the reference three dimensional image, thereby calculating a value of a predetermined parameter. This image matching may use any method or technique such as an image correlation, feature-based matching, area-based matching, machine learning (learned model), and so forth. The parameter to be calculated may be any kind of parameter such as a correlation value, a matching parameter (e.g., angle, scale, similarity, degree of congruity (degree of agreement), etc.), an output parameter of a trained model, and so forth.

Such image matching is typically a process of generating a quantitative representation (i.e., representation by a numerical value) of a degree (extent) to which a feature (e.g., the shape and/or structure) of a tissue and/or site depicted in a three dimensional image is similar to a feature (e.g., the shape and/or structure) of a standard normal eye and/or to a feature (e.g., the shape and/or structure) of a standard eye with a disease. Here, the tissue or the site may be any of a cornea, an iris, a pupil, a corner angle, and other parts of an eye.

The assessing processor 813B is configured to execute the assessment of the quality of the corresponding image group based on the parameter value calculated by the comparing processor 812B. For example, the assessing processor 813B may be configured to execute the assessment of the quality of the corresponding image group by executing a comparison between the parameter value calculated by the comparing processor 812B and a predetermined threshold value. Alternatively, the assessing processor 813B may be configured to execute the assessment of the quality of the corresponding image group by determining whether or not the parameter value calculated by the comparing processor 812B falls within a predetermined range. Note that the method or technique used for processing executed by the assessing processor 813B is not limited to the above examples, and may be any method or technique that can be used to derive an assessment result from a value of a certain parameter.

The method or technique used for the quality assessment of an image group executed by using three dimensional image construction is not limited to the present example. In some examples, the image group assessing processor 81 may be configured to be capable of executing any one or more of the following assessment processing options in the same manner as the image set assessing processor 83: an assessment of the arrangement order of a series of images composing an image group; an assessment of skipping (lack, omission) of an image among a series of images composing an image group; and an assessment of misalignment between a series of images composing an image group.

Figure 5D:
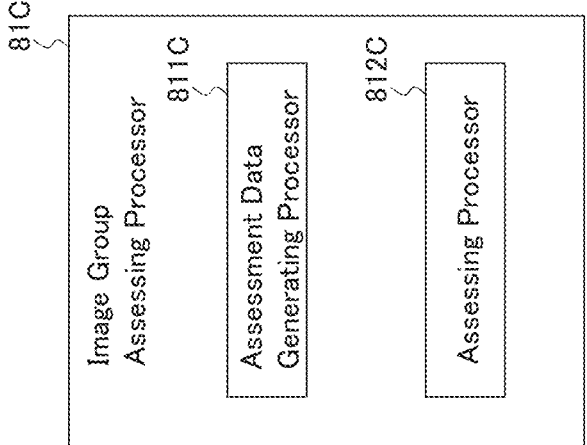
FIG. 5D is a schematic diagram illustrating a configuration of a slit lamp microscope according to an aspect example.

The third example of the image group assessing processor 81 will be described with reference to FIG. 5D. The present example executes a quality assessment by way of a quantitative assessment of an image quality of an image group. The image group assessing processor 81C shown in FIG. 5D includes the assessment data generating processor 811C and the assessing processor 812C.

The assessment data generating processor 811C is configured to execute generation of image quality assessment data from an image included in an image group collected by a single scan of the anterior segment of the subject's eye E. The image quality assessment data quantitatively represents the image quality of the image group.

Several examples of image quality assessment processing executed by the assessment data generating processor 811C will be described. In some aspect examples, the image quality assessment processing executed by the assessment data generating processor 811C may be a freely selected or determined kind of processing, and may be processing conducted by using any known technique or technology such as any of the following options: signal-to-noise ratio (SNR); contrast-to-noise ratio (CNR); root mean square (RMS) granularity; Wiener spectrum; modulation transfer function (MTF); and quality index (QI).

In some examples, the assessment data generating processor 811C calculates a value of a predetermined image quality assessment index (image quality assessment value) as image quality assessment data of an image group. An image quality assessment value may be a freely selected or determined kind of parameter that quantitatively represents a quality of an image. In some typical examples, the higher a quality of an image, the greater an image quality assessment value.

As an example of the method of calculating an image quality assessment value, a description will be given below of a method of calculating an image quality value (IQ value) used for assessing an image quality of an OCT image. To begin with, the assessment data generating processor 811C applies a predetermined analysis process (e.g., segmentation) to an assessment region determined in an image to be assessed. With this analysis process, the assessment data generating processor 811C detects an image region corresponding to a tissue (site) of the anterior segment (referred to as a tissue image region) and an image region other than the tissue image region (referred to as a background region of non-tissue image region). The assessment data generating processor 811C then generates a histogram of brightness based on the tissue image region and a histogram of brightness based on the background region. Subsequently, the assessment data generating processor 811C calculates an image quality assessment value (IQ value) based on the degree of overlap between these two histograms. For example, the range of the IQ value in is defined to be [0, 100] such that the IQ value=0 when the two histograms are completely overlapping with each other and the IQ value=100 when the two histograms are completely separated from each other. This image quality assessment calculation of some examples may include normalization of two histograms, generation of a probability distribution function, calculation of an IQ value using a predetermined arithmetic expression, and so forth.

As described thus far, the assessment data generating processor 811C may be configured to execute the following processes: the process of identifying a tissue image region in an image to be assessed corresponding to a tissue of an anterior segment and identifying a background region; the process of generating the first histogram showing a frequency distribution of brightness (brightness frequency distribution) in the tissue image region; the process of generating the second histogram showing a brightness frequency distribution in the background region; and the process of calculating the image quality assessment value (IQ value), which is used as an image quality assessment data, based on the first histogram and the second histogram.

The assessment processor 812C is configured to execute an assessment of a quality of the image group based on the image quality assessment data generated by the assessment data generating processor 811C. While several methods and techniques for a quality assessment conducted based on image quality assessment data will be described below, quality assessment methods and techniques are not limited to these examples and may be freely selected from known methods and techniques.

A description is given of the first example of the quality assessment executed based on image quality assessment data. In the case where an IQ value is obtained for each image included in an image group, the assessing processor 812C executes a comparison between each of the plurality of IQ values obtained for this image group and a predetermined threshold value. If all of the plurality of IQ values are equal to or greater than the threshold value, the assessing processor 812C determines that the quality of the image group is satisfactory. On the other hand, if any one or more of the plurality of IQ values are less than the threshold value, the assessing processor 812C determines that the quality of the image group is not satisfactory.

A description is given of the second example of the quality assessment executed based on image quality assessment data. In the case where an IQ value is obtained for each image included in an image group, the assessing processor 812C executes selection of the lowest IQ value from among the plurality of IQ values obtained for this image group, and executes a comparison between this selected lowest IQ value and a predetermined threshold value. If the lowest IQ value is equal to or greater than the threshold value, the assessing processor 812C determines that the quality of the image group is satisfactory. On the other hand, if the lowest IQ value is less than the threshold value, the assessing processor 812C determines that the quality of the image group is not satisfactory.

A description is given of the third example of the quality assessment executed based on image quality assessment data. In the case where an IQ value is obtained for each image included in an image group, the assessing processor 812C executes application of a predetermined statistical calculation to the plurality of IQ values obtained for this image group, thereby calculating a statistical value. The type of this statistical value may be freely selected or determined, and may be, for example, any of the following options: a mean value (average value), minimum value, maximum value, mode, and median value. Note that the case where a minimum value is used as the statistical value corresponds to the second example described above. The assessing processor 812C executes a comparison between the calculated statistical value and a predetermined threshold value. If the statistical value is equal to or greater than the threshold value, the assessing processor 812C determines that the quality of the image group is satisfactory. On the other hand, if the statistical value is less than the threshold value, the assessing processor 812C determines that the quality of the image group is not satisfactory.

The processing executed by the assessing processor 812C is not limited to processing on the basis of image quality assessment data generated by the assessment data generating processor 811C. In some examples, the assessing processor 812C may be configured to be capable of executing any one or more of the following options of assessment processing (all of which are described above): an assessment of the arrangement order of a series of images composing an image group; an assessment of skipping (lack, omission) of an image among a series of images composing an image group; and an assessment of misalignment between a series of images composing an image group.

<Other Elements>

In addition to the elements shown in FIG. 1, the slit lamp microscope 1 may further include a display device and an operation device. In some other aspect examples, a display device and an operation device may be peripheral devices of the slit lamp microscope 1.

The display device is configured to display various kinds of information under the control of the controller 7. The display device may include a flat panel display such as a liquid crystal display (LCD).

The operation device includes a device for operating the slit lamp microscope 1 and/or a device for inputting information. The operation device includes, for example, a button, a switch, a lever, a dial, a handle, a knob, a mouse, a keyboard, a trackball, an operation panel, or the like.

A device such as a touch screen may be employed in which a display device and an operation device are integrated (combined).

The subject (patient) or an assistant may operate the slit lamp microscope 1 by using the display device and the operation device.

<Alignment>

A description will be given of the alignment of the slit lamp microscope 1 with respect to the subject's eye E. Alignment, in general, is an operation to place an optical system of an apparatus at an appropriate position for photography or measurement of the subject's eye E. The alignment of the present aspect example is an operation to place the illumination system 2 and the photography system 3 at appropriate positions for acquisition of a plurality of anterior segment images (a series of images, a moving image, an image group, or an image set) as shown in FIG. 3.

There are various kinds of methods and techniques for alignment of an ophthalmic apparatus. While some alignment methods and techniques will be described below, alignment methods and techniques applicable to the present aspect example are not limited to these examples.

One of the alignment methods and techniques applicable to the present aspect example is stereo alignment. Stereo alignment may be applicable to an ophthalmic apparatus capable of photographing an anterior segment from two or more mutually different directions (two or more mutually different viewpoints). A specific method of stereo alignment is disclosed by the present applicant in Japanese Unexamined Patent Application Publication No. 2013-248376. Stereo alignment includes, for example, the following steps: a step of photographing the anterior segment from different directions by two or more anterior segment cameras to acquire two or more photographed images; a step of analyzing the photographed images by a processor to determine a three dimensional position of the subject's eye; and a step of performing a movement control of an optical system by a processor based on the three dimensional position determined. With such an alignment operation, the optical system (the illumination system 2 and the photography system 3 in the present example) is brought to and placed at an appropriate alignment position with respect to the subject's eye. The position of the pupil (e.g., the center of the pupil or the center of gravity of the pupil) of the subject's eye is used as a reference (or an indicator) in a typical stereo alignment.

In addition to the stereo alignment described hereinbefore, any known alignment methods and techniques may be employed, such as an alignment method or technique using a Purkinje image formed by alignment light, an alignment method or technique using an optical lever, or an alignment method or technique using an alignment indicator. The alignment method or technique using a Purkinje image and the alignment method or technique using an optical lever or an alignment indicator uses the position of the corneal apex of the subject's eye as a reference.

Conventional typical alignment methods and techniques including the above examples are performed for the purpose of matching the optical axis of an optical system with the axis of a subject's eye. On the other hand, the present aspect example may perform alignment so as to place the illumination system 2 and the photography system 3 at a position corresponding to the scan start position.

The first example of the alignment of the present aspect example may be carried out in the following manner. First, alignment with reference to the pupil or corneal apex of the subject's eye E may be performed by applying any of the alignment methods and techniques described above. Then, the illumination system 2 and the photography system 3 may be moved (in the X direction) by a distance corresponding to a standard value of the corneal radius determined in advance. Note that a measurement value of the corneal radius of the subject's eye E may be used instead of the standard value.

The second example of the alignment of the present aspect example may be carried out in the following manner. First, alignment with reference to the pupil or corneal apex of the subject's eye E may be performed by applying any of the alignment methods and techniques described above. Second, the corneal radius of the subject's eye E may be measured by analyzing an image of anterior segment. Third, the illumination system 2 and the photography system 3 may be moved (in the X direction) by a distance corresponding to the measurement value of the corneal radius of the subject's eye E. The image of the anterior segment analyzed in the present example is an anterior segment image obtained by the photography system 3 or another image, for example. This another image here may be an image of any kind, such as an image obtained by an anterior segment camera, an image obtained by an anterior segment OCT, or the like.

The third example of the alignment of the present aspect example may be carried out in the following manner. First, the first edge position of the cornea may be determined by analyzing an image of the anterior segment acquired by the anterior segment camera for stereo alignment or by the photography system 3. Then, the illumination system 2 and the photography system 3 may be moved to a position corresponding to the first edge position by applying stereo alignment.

It should be noted that alignment may be performed with reference to the pupil or corneal apex of the subject's eye E by applying any of the alignment methods and techniques described above, and then the anterior segment scan with slit light may be started from the position determined by the alignment. In such a case as well, a scan sequence may be determined to scan the entire cornea C. For example, the scan sequence may be determined such that the scan is performed to the left from the position determined by the alignment and then to the right.

<Some Additional Matters and Items>

The slit lamp microscope 1 may be provided with a fixation system configured to output light for fixation of the subject's eye E (referred to as fixation light). The fixation system of some typical examples includes at least one visible light source (referred to as a fixation light source(s)) or a display device configured to display an image such as a landscape chart or a fixation target. The fixation system of some example aspects is arranged coaxially or non-coaxially with the illumination system 2 or the photography system 3. The fixation system may include an internal fixation system and/or an external fixation system. The internal fixation system is configured to present a fixation target to the subject through the optical path of an optical system of an apparatus. The external fixation system is configured to present a fixation target to the subject from outside the optical path of an optical system of an apparatus.

The types (kinds) of images that may be acquired by the slit lamp microscope 1 are not limited to the plurality of anterior segment images shown in FIG. 3. For example, the slit lamp microscope 1 may acquire any of the following types of images: a three dimensional image constructed based on the plurality of anterior segment images; a rendered image constructed based on the three dimensional image; a transillumination image (red reflex image); a moving image representing movement of a contact lens applied to the subject's eye; and an image representing a gap between a contact lens and the corneal surface by fluorescent agent administration. A rendered image will be described in another aspect example. A transillumination image is an image obtained by a red reflex technique (transillumination) for depicting opacity and foreign bodies in the eye by using the retinal reflection of illumination light. Note that the slit lamp microscope 1 may be capable of carrying out fundus photography, corneal endothelial cell photography, Meibomian gland photography, and any other imaging modalities.

<Operation>

Several examples of an operation of the slit lamp microscope 1 will be described.

While not shown in the drawings, the user (a subject, an examiner, or an assistant) inputs subject information into the slit lamp microscope 1 at any stage. The subject information that has been input is stored in the controller 7. The subject information of some typical examples includes identification information (identifier) of the subject (referred to as subject ID).

Furthermore, background information may also be input. The background information is any kind of information related to the subject, and examples thereof include information acquired by a medical interview of the subject, information on a sheet filled in by the subject, information recorded in the electronic medical record of the subject, and so forth. In some typical examples, the background information includes the subject's data on items such as gender, age, height, weight, disease name, possible disease name, examination result (e.g., visual acuity value, eye refractive power value, intraocular pressure value), history of a wearing device for refractive correction (e.g., history of wearing glasses, contact lenses) and the power of the device, examination history, and treatment history. These are merely examples, and possible items of the background information are not limited to these examples.

Further, in preparation for photography, the table on which the slit lamp microscope 1 is installed, the chair on which the subject sits, and the chin rest of the slit lamp microscope 1 are adjusted (all not shown in the drawings). For example, the heights of the table, chair and chin rest are adjusted. The chin rest is provided with a chin rest member and a forehead rest member for stably positioning the face of the subject.

After the completion of the preparation, the subject sits on the chair, puts his/her chin on the chin rest member, and puts his/her forehead on the forehead rest member. Before or after these actions, the user performs an operation of issuing an instruction to start photography of the subject's eye. This operation may be conducted, for example, by pressing a photography start trigger button (not shown in the drawings) or inputting a voice instruction. Alternatively, the controller 7 may detect the completion of the preparation phase and automatically shift to the photography phase. In addition, a fixation target (not shown in the drawings) may be presented to the subject (the subject's eye E or the fellow eye thereof).

<First Operation Example>

Figure 6:
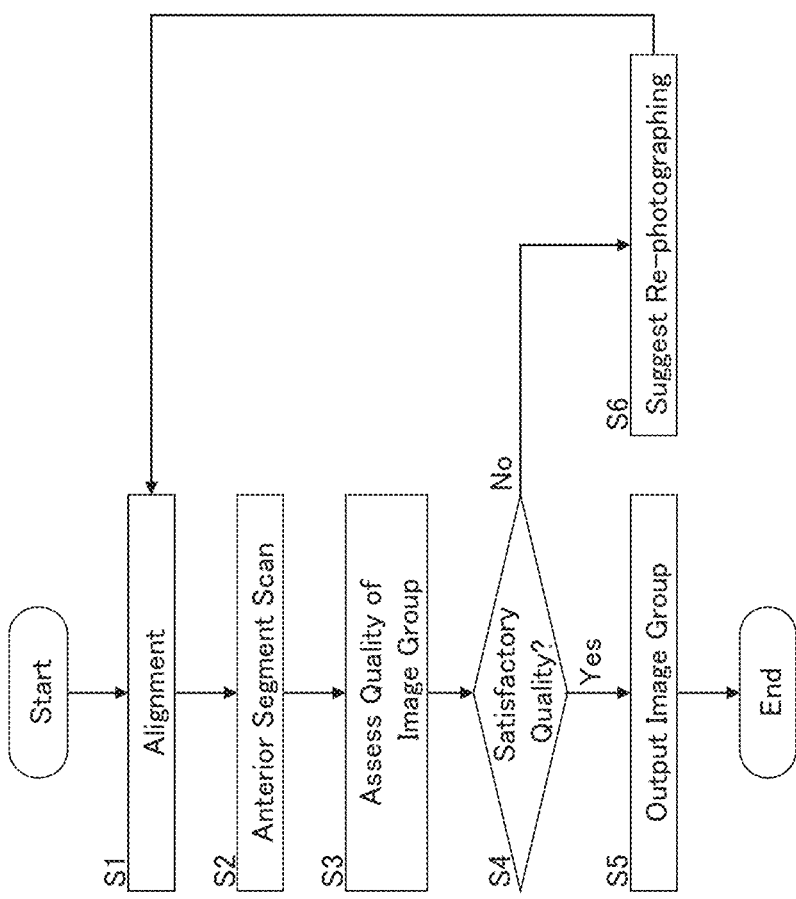
FIG. 6 is a flowchart illustrating an operation of a slit lamp microscope according to an aspect example.

The first operation example performed after the above preparations will be described with reference to FIG. 6.

(S1: Alignment)

Upon commencing photography, the slit lamp microscope 1 performs alignment of the illumination system 2 and the photography system 3 with respect to the subject's eye E. Unlike general alignment operations for aligning the optical axis of an optical system with the corneal apex or the center of the pupil of the subject's eye E, the alignment in the step S1 is performed to place the illumination system 2 and the photography system 3 at a start position of the anterior segment scan to be performed in the step S2.

The mode (aspect) of the alignment of the step S1 may be freely selected or determined, and may be any of the following modes, for example: stereo alignment; manual or automatic alignment using a Purkinje image; manual or automatic alignment using an optical lever; and manual or automatic alignment using an alignment index (alignment target).

Some aspect examples employ such conventional alignment methods and techniques to perform alignment targeting the corneal apex or the center of the pupil. In addition, the controller 7 moves the illumination system 2 and the photography system 3, which have been moved by the alignment targeting the corneal apex or the center of the pupil, further to the scan start position (the position corresponding thereto).

Some other aspect examples perform alignment targeting the scan start position from the beginning. This alignment may include, for example, a process of identifying the scan start position by analyzing an image of the anterior eye segment, and a process of moving the illumination system 2 and the photography system 3 to a position corresponding to the identified scan start position. Here, the image of the anterior eye segment to be analyzed is, for example, an image captured from the front or an oblique direction, and the scan start position to be identified is, for example, the first edge position of the cornea described above or a position that is a predetermined distance away from the first edge position in the direction opposite to the axis of the subject's eye E.

A predetermined operation may be performed before the commencement of alignment, during alignment, and/or after the completion of alignment. For example, adjustment of the image sensor 5, focus adjustment or the like may be carried out.

(S2: Anterior Segment Scan)

The slit lamp microscope 1 scans the anterior segment of the subject's eye E by combining the projection of the slit light performed by the illumination system 2, the moving image photography performed by the photography system 3, and the movement of the illumination system 2 and the photography system 3 performed by the movement mechanism 6 in the manner described above. As a result of a single scan (that is, a scan from the scan start position to the scan end position), for example, the image group (a plurality of anterior segment images) F1 to FN shown in FIG. 3 is obtained.

The data processor 8 may be configured to perform predetermined processing on an image obtained by the scan application. For example, freely selected or determined signal processing and/or freely selected or determined image processing may be applied to an image obtained by the scan application, such as noise elimination, contrast adjustment, brightness adjustment, and color correction.

(S3: Assess Quality of Image Group)

The image group assessing processor 81 executes an assessment of the quality of the image group collected by the anterior segment scan of the step S2.

(S4: Satisfactory Quality?)

In the case where the image group assessing processor 81 has determined in the step S3 that the quality of the image group is satisfactory (S4: Yes), the operation proceeds to the step S5. On the other hand, in the case where the image group assessing processor 81 has determined in the step S3 that the quality of the image group is not satisfactory (S4: No), the operation shifts to the step S6.

(S5: Output Image Group)

When the image group assessing processor 81 has determined in the step S3 that the quality of the image group is satisfactory (S4: Yes), the controller 7 performs a control to output this image group. In the present example, the controller 7 controls the communication device 9 to transmit the image group to another apparatus.

Examples of an apparatus to which the image group is transmitted include an information processing apparatus and a storage. The information processing apparatus is, for example, a server on a wide area network, a server on a LAN, a computer terminal, or the like. The storage may be a storage device provided on a wide area network, a storage provided on a LAN, or the like.

The image group output in the step S5 may include the background information described above. Alternatively, the background information may be supplementary information attached to the image group. In general, the data structure of the information output in the step S5 may be selected accordingly.

In some typical examples, the image group transmitted in the step S5 includes a series of images of the anterior segment of the subject's right eye and a series of images of the anterior segment of the subject's left eye. The series of images of the right eye and the series of images of the left eye are obtained by applying the operations described in the present example to the right eye and the left eye, respectively. The subject's eye information described above is attached to the series of images of the right eye and the subject's eye information is attached to the series of images of the left eye, whereby the series of images of the right eye and the series of images of the left eye are distinguished from each other.

Identification information of the subject is transmitted together with the image group. The identification information may be the subject ID input into the slit lamp microscope 1, or identification information generated based on the subject ID. For example, the subject ID used for personal identification in the facility where the slit lamp microscope 1 is installed (referred to as internal identification information) may be converted into external identification information used outside the facility. Such identification information conversion makes it possible to improve the information security of personal information such as image groups and background information.

(S6: Suggest Re-Photographing)

In the case where the image group assessing processor 81 has determined in the step S3 that the quality of the image group is not satisfactory (S4: No), the controller 7 then performs a control for acquisition of another image group. The controller 7 of the present example performs a control for displaying information and/or outputting audio (voice) information to suggest the user to conduct photography again. The user then conducts an operation of issuing an instruction to start re-photographing or an operation of issuing an instruction not to re-perform photography.

If the user performs the operation of issuing the instruction to start re-photographing, the controller 7 performs a control to re-execute the operation from the step S1 (or the step S2). The re-photographing may be repeated, for example, up to a predetermined number of times.

On the other hand, if the user performs the operation of issuing the instruction not to re-perform photography, the controller 7 of some examples may perform a control to transmit the image group determined to be of unsatisfactory quality to another apparatus. Alternatively, the controller 7 of some examples may perform a control to delete, save, or record the image group determined to be of unsatisfactory quality.

The image group transmitted from the slit lamp microscope 1 in the step S5 (or S6) is sent directly or indirectly to an information processing apparatus. A typical example of this information processing apparatus is the aforementioned image interpretation computer terminal for the use of a doctor (or an optometrist).

The doctor can conduct image interpretation of the series of images included in the image group (e.g., the series of images F1 to FN shown in FIG. 3) using the image interpretation computer terminal. Further, a three dimensional image may be constructed from the series of images, a rendered image of the three dimensional image may be displayed, or background information may be displayed. In addition, analysis of any image in the series of images may be performed, analysis of the three dimensional image may be performed, analysis of the rendered image may be performed, or analysis of the background information may be performed by the image interpretation computer terminal or another information processing apparatus.

By using the image interpretation computer terminal, the doctor can generate a report (an image interpretation report) in which information obtained from image interpretation is recorded. The image interpretation report may be offered, for example, to the facility where the slit lamp microscope 1 is installed, to a medical institution designated by the subject or the like, to an information processing apparatus used by a doctor designated by the subject or the like, to an address (e.g., email address, postal address, etc.) registered by the subject or the like. Further, the image interpretation report may be sent to a predesignated database system to be stored and managed.

An image interpretation apparatus is another example of the information processing apparatus that is a destination of the image group transmitted from the slit lamp microscope 1 in the step S5 (or S6). The image interpretation apparatus includes an image interpretation processor. The image interpretation processor is configured to operate, for example, in accordance with a program for image interpretation, and analyze the series of images included in the image group to derive findings. In addition, the image interpretation processor is configured to generate a report based on the findings derived.

The image interpretation processor may include an artificial intelligence engine that performs image interpretation using a learned model (inference model). The artificial intelligence engine of some typical examples includes a convolutional neural network (CNN) trained with training data containing a large number of images acquired by slit lamp microscopes and corresponding image interpretation information.

In the case where the image interpretation apparatus includes an artificial intelligence engine and the slit lamp microscope 1 (the data processor 8) also includes an artificial intelligence engine, these artificial intelligence engines may be adjusted to have equivalent capabilities (abilities, faculties, qualities). In other words, it is possible to make adjustments so that there is no capability difference (so that capability difference is small) between the artificial intelligence engine of the image interpretation apparatus and the artificial intelligence engine of the slit lamp microscope 1. Further in other words, the artificial intelligence engine provided in the image interpretation apparatus may be the same at least in part as the aforementioned artificial intelligence engine provided in the slit lamp microscope 1.

In some aspect examples, both the artificial intelligence engines may be configured by applying the same neural network model and the same parameters. In addition, the models and the parameters of both the artificial intelligence engines may be updated in synchronization with each other.

Such a unified (integrated, synchronized) adjustment of the artificial intelligence engines makes it possible to prevent the inconvenience of inconsistencies or errors between outputs from the artificial intelligence engine of the slit lamp microscope 1 and outputs from the artificial intelligence engine of the image interpretation apparatus. In addition, as described above, the quality assessment conducted before transmitting an image group from the slit lamp microscope 1 is a process of assessing the image quality required for effective image interpretation and diagnosis. Therefore, performing the unified adjustment of the artificial intelligence engines makes it possible to achieve appropriate execution of the image quality assessment of an image group before transmission. With this, an image group that is suitable for image interpretation by the artificial intelligence engine of the image interpretation apparatus can be assessed with high accuracy as a "suitable image group for image interpretation" prior to transmission from the slit lamp microscope 1. Also, an image group that is not suitable for image interpretation by the artificial intelligence engine of the image interpretation apparatus can be assessed with high accuracy as an "unsuitable image group for image interpretation" prior to transmission from the slit lamp microscope 1.

In the case where such a unified adjustment of the artificial intelligence engines is not made, or in the case where image interpretation is requested to another image interpretation apparatus that includes an artificial intelligence engine with a different model and/or parameters, a processing condition of the artificial intelligence engine of the slit lamp microscope 1 may be attached to an image group to be transmitted, and/or, a processing condition of the artificial intelligence engine of the image interpretation apparatus may be attached to an image group to be transmitted. Here, the processing conditions represent a corresponding model, corresponding parameters, or the like.

According to the first operation example as described above, in the case where an image group having a satisfactory quality is acquired by the first scan, this image group can be provided for subsequent processing such as image interpretation. On the other hand, in the case where an image group of a satisfactory quality cannot be acquired by the first scan, the slit lamp microscope 1 can perform acquisition of an image group again. More generally, the slit lamp microscope 1 can repeatedly perform photography until an image group with a satisfactory quality is obtained. Therefore, the slit lamp microscope 1 is capable of providing an image group with a satisfactory quality for subsequent processing in either case where an image group with a satisfactory quality is or is not obtained by the first scan and in the case. This concludes the description of the first operation example.

<Second Operation Example>

Figure 7:
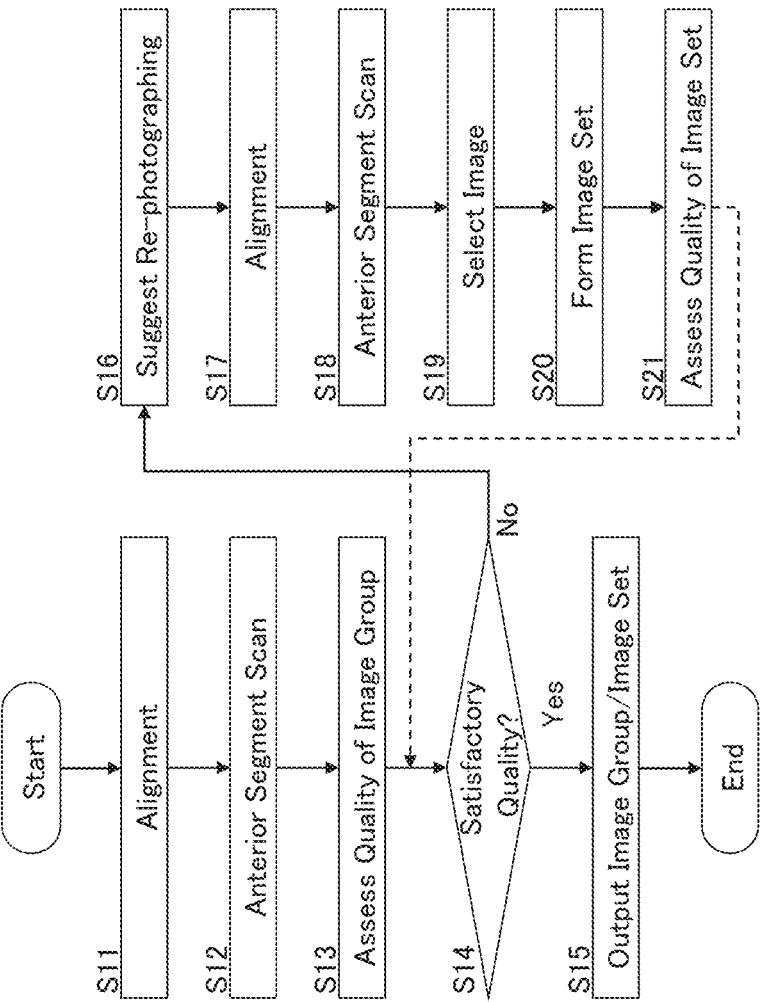
FIG. 7 is a flowchart illustrating an operation of a slit lamp microscope according to an aspect example.

The second operation example of the slit lamp microscope 1 will be described with reference to FIG. 7.

While the first operation example described above is operated to repeat anterior segment scanning (photography) until an "image group" with a satisfactory quality is obtained, the present operation example is operated to repeat anterior segment scanning (photography) until an "image set" with a satisfactory quality is obtained. Here, an image group refers to a series of images collected by a single scan, and an image set refers, for example, to a series of images arranged in a predetermined scan area.

In other words, while data finally obtained by the first operation example is a series of images collected by a single scan, data finally obtained by the present operation example is, for example, a series of images arranged in a predetermined scan area. To put it another way, data finally obtained by the present operation example may be a series of images obtained by a single scan as in the first operation example, or, unlike the first operation example, may be a series of images selected from two or more image groups obtained by two or more times of scans.

The steps S11 to S13 of the present operation example may be performed in the same manner as the steps S1 to S3 of the first operation example, respectively. Therefore, the description of the steps S11 to S13 is omitted. In addition, the matters and items described in the first operation example may be combined with the present operation example, unless otherwise mentioned.

(S14: Satisfactory Quality?)

In the case where the image group assessing processor 81 has determined in the step S13 that the quality of the image group is satisfactory (S14: Yes), the operation proceeds to the step S15. On the other hand, in the case where the image group assessing processor 81 has determined in the step S13 that the quality of the image group is not satisfactory (S14: No), the operation shifts to the step S16.

(S15: Output Image Group)

When the image group assessing processor 81 has determined in the step S13 that the quality of the image group collected by the first scan is satisfactory (S14: Yes), the controller 7 performs a control to output this image group. As in the first operation example, the controller 7 can transmit this image group to another apparatus by controlling the communication device 9.

(S16: Suggest Re-Photographing)

In the case where the image group assessing processor 81 has determined in the step S13 that the quality of the image group is not satisfactory (S14: No), the controller 7 then performs a control to suggest the user to conduct photography again. The user then performs an operation of issuing an instruction to start re-photographing or an operation of issuing an instruction not to re-perform photography.

In the present operation example, the case of performing re-photographing will be described below. In the case of not performing re-photographing, the same or similar operation as or to the first operation example can also be conducted in the present operation example.

(S17: Alignment)

Upon receiving an instruction from the user to start re-photographing, the controller 7 performs alignment in the same manner as in the step S11.

42

(S18: Anterior Segment Scan)

After completing the alignment in the step S17, the slit lamp microscope 1 applies a scan to the anterior segment of the subject's eye E in the same manner as in the step S12. Another image group is obtained by this scan.

(S19: Select Image)

The selecting processor 821 selects one or more images that satisfy a predetermined condition, from among a set of images that includes the image group collected by the anterior segment scan of the step S12 and the image group collected by the anterior segment scan of the step S18. Note that in the case where a determination result "No" has been issued two or more times in the step S14, the selecting processor 821 selects one or more images that satisfy the predetermined condition, from a set of images that includes the image group collected by the anterior segment scan of the step S12 and two or more image groups collected by the two or more times of anterior segment scans performed in the step S18.

In some aspect examples, the combination of the operation of the step S18 and the operation of the step S19 may be either one of an operation of alternately performing scan application and image selection or an operation of performing image selection after executing all scans, as described above. By such an interlocking operation of the scan application and the image selection, a series of images is selected from two or more image groups obtained by two or more times of scans. A specific example of such alternate execution of the scan application and the image selection will be described later in the second aspect example.

(S20: Form Image Set)

The image set forming processor 82 forms an image set including a series of images selected in the step S19.

(S21: Assess Quality of Image Set)

The image set assessing processor 83 assesses the quality of the image set formed in the step S20.

(S14: Satisfactory Quality?)

In the case where the image set assessing processor 83 has determined in the step S21 that the quality of the image set is satisfactory (S14: Yes), the operation proceeds to the step S15. On the other hand, in the case where the image set assessing processor 83 has determined in the step S21 that the quality of the image set is not satisfactory (S14: No), the operation shifts to the step S16 and then the processes of the steps S16 to S14 are performed again.

(S15: Output Image Set)

When the quality of the image set is determined in the step S13 to be satisfactory (S14: Yes), the controller 7 performs a control to output this image set. In the present example, the controller 7 controls the communication device 9 to transmit the image set to another apparatus.

The destination of the image set transmitted may be the same as or different from the destination of the image group. The image set output may include the background information described above. Alternatively, the background information may be supplementary information attached to the image set. As in the case of the image group, the image set transmitted may include a series of images of the anterior segment of the subject's right eye and a series of images of the anterior segment of the subject's left eye. Furthermore, the subject's eye information may be attached to the series of images of the right eye and the subject's eye information is attached to the series of images of the left eye. In addition, identification information of the subject may be transmitted together with the image set.

The image set transmitted from the slit lamp microscope 1 in the step S15 is sent directly or indirectly to an information processing apparatus. A typical example of this information processing apparatus is the aforementioned image interpretation computer terminal for the use of a doctor (or an optometrist).

The doctor can conduct image interpretation of the series of images included in the image set using the image interpretation computer terminal. Further, a three dimensional image may be constructed from the series of images, a rendered image of the three dimensional image may be displayed, or background information may be displayed. In addition, analysis of any image in the series of images may be performed, analysis of the three dimensional image may be performed, analysis of the rendered image may be performed, or analysis of the background information may be performed.

By using the image interpretation computer terminal, the doctor can generate a report (an image interpretation report) in which information obtained from image interpretation of the image set is recorded. The image interpretation report may be offered, for example, to the facility where the slit lamp microscope 1 is installed, to a medical institution designated by the subject or the like, to an information processing apparatus used by a doctor designated by the subject or the like, to an address (e.g., email address, postal address, etc.) registered by the subject or the like. Further, the image interpretation report may be sent to a predesignated database system to be stored and managed.

An image interpretation apparatus is another example of the information processing apparatus that is a destination of the image set transmitted from the slit lamp microscope 1 in the step S15. The image interpretation apparatus includes an image interpretation processor. The image interpretation processor is configured to operate, for example, in accordance with a program for image interpretation, and analyze the series of images included in the image set to derive findings. In addition, the image interpretation processor is configured to generate a report based on the findings derived.

The image interpretation processor may include an artificial intelligence engine that performs image interpretation using a learned model (inference model). The artificial intelligence engine of some typical examples includes a convolutional neural network (CNN) trained with training data containing a large number of images acquired by slit lamp microscopes and corresponding image interpretation information.

In the case where the image interpretation apparatus includes an artificial intelligence engine and the slit lamp microscope 1 (the data processor 8) also includes an artificial intelligence engine, these artificial intelligence engines may be adjusted to have equivalent capabilities (abilities, faculties, qualities). In other words, it is possible to make adjustments so that there is no capability difference (so that capability difference is small) between the artificial intelligence engine of the image interpretation apparatus and the artificial intelligence engine of the slit lamp microscope 1. Further in other words, the artificial intelligence engine provided in the image interpretation apparatus may be the same at least in part as the aforementioned artificial intelligence engine provided in the slit lamp microscope 1. In some aspect examples, both the artificial intelligence engines may be configured by applying the same neural network model and the same parameters. In addition, the models and the parameters of both the artificial intelligence engines may be updated in synchronization with each other. In other words, it is possible to make a unified adjustment between the artificial intelligence engine of the slit lamp microscope 1 and the artificial intelligence engine of the image interpretation apparatus. In the case where such a unified adjustment of the artificial intelligence engines is not made, or in the case where image interpretation is requested to another image interpretation apparatus that includes an artificial intelligence engine with a different model and/or parameters, a processing condition of the artificial intelligence engine of the slit lamp microscope 1 may be attached to the image set, and/or, a processing condition of the artificial intelligence engine of the image interpretation apparatus may be attached to the image set. Here, the processing conditions represent a corresponding model, corresponding parameters, or the like.

According to the second operation example as described thus far, in the case where an image group of a satisfactory quality is acquired by the first scan, this image group can be provided for subsequent processing such as image interpretation. On the other hand, in the case where an image group of a satisfactory quality cannot be acquired by the first scan, the slit lamp microscope 1 is capable of acquiring another image group and then forming an image set having a satisfactory quality by selecting a series of images from two or more image groups obtained up to that point of time. More generally, the slit lamp microscope 1 can repeatedly perform photography until an image set with a satisfactory quality is obtained. Therefore, when an image group of a satisfactory quality is acquired by the first scan, this image group can be provided for subsequent processing. In addition, when the first scan yields no image group of a satisfactory quality, an image set of a satisfactory quality can be formed based on two or more image groups acquired by two or more times of scans and this image set can then be provided for subsequent processing. This concludes the description of the second operation example.

It should be noted that the operations that can be performed by the slit lamp microscope 1 of the present aspect example are not limited to the two examples described above. In some examples, the slit lamp microscope 1 may be configured to perform an operation based at least on any one or two or more of the matters and items described in the present aspect examples, any modification thereof, and any known technique or technology.

<Advantageous Effects, Etc.>

Some features, some actions, and some advantageous effects of the slit lamp microscope 1 of the present aspect example will be described.

The slit lamp microscope 1 includes a scanner (the illumination system 2, the photography system 3, and the movement mechanism 6), the image group assessing processor 81 (the first assessing processor), and the controller 7. The scanner is configured to perform application of a scan to the anterior segment of the subject's eye E with slit light to collect an image group. The image group assessing processor 81 is configured to execute an assessment of a quality of the image group collected by the scanner. The controller is configured to selectively execute at least two predetermined control modes according to a result of the assessment of the quality obtained by the first assessing processor.

As described above, acquisition of satisfactory images using a conventional slit lamp microscope requires fine and complicated operations. However, with the remote operation techniques as disclosed in Patent Documents 3 and 4, such difficult operations have to be conducted from a remote place. Therefore, it is considered extremely difficult to obtain images of quality good enough for diagnosis (image interpretation) using a conventional slit lamp microscope with such a conventional remote operation function. Further, although a slit lamp microscope serves an effective role in screening and like applications, it can be said, in view of the difficulties of remote operations, that it is practically impossible to use a conventional slit lamp microscope for tele-medicine with conventional techniques.

In contrast, the slit lamp microscope 1 of the present aspect example is configured to first performs a scan of the anterior segment of the subject's eye E to collect an image group, and hence remote operations conducted by a doctor as in conventional cases are not required.

In addition, the quality of the image group collected by scanning the anterior segment can be assessed by the slit lamp microscope itself. Thus, the quality of the image group can be checked before offering the image group to a doctor or an image interpretation apparatus.

Furthermore, the present aspect example is capable of switching the control modes (contents of control) according to a result of the assessment of the quality of the image group obtained by the image group assessing processor 81. Therefore, when an image group of a satisfactory quality is obtained, suitable processing can be executed accordingly, and when an image group of a satisfactory quality is not obtained, suitable processing can be executed accordingly, too.

Thus, the slit lamp microscope 1 of the present aspect example is capable of offering, to a doctor or an image interpretation apparatus, an image group of a satisfactory quality acquired by applying a scan to the anterior eye segment, which makes it possible to widely provide high quality slit lamp microscope examinations.

In addition, conventional methods require a doctor to conduct a medical examination and consultation while performing operations of a slit lamp microscope from a remote place. In the present aspect example, on the other hand, a doctor only needs to perform image interpretation of an image group acquired in advance. In other words, according to the present aspect example, a doctor can be freed from the time and effort required for performing photography, and therefore concentrate on image interpretation. As a result, the present aspect example can contribute to diffusion of high quality slit lamp microscope examinations.

The slit lamp microscope 1 of the present aspect example may further include the communication device 9 for performing data communication. Furthermore, the controller 7 may be configured to execute, in the case where the image group assessing processor 81 assesses that the quality of the image group collected by the scanner is satisfactory, a control of the communication device 9 to transmit this image group to a predetermined external device such as an image interpretation computer terminal or an image interpretation apparatus.

Such a configuration makes it possible, upon acquisition of an image group of a satisfactory quality, to provide this image group to a doctor who is at a remote place or an image interpretation apparatus located at a remote place, for example.

In the present aspect example, the controller 7 may be configured to execute a control of the scanner to apply another scan to the anterior segment of the subject's eye E when the image group assessing processor 81 assesses that the quality of the image group is not satisfactory. This is one example of the selectively executable control modes. Note that the control mode for causing the scanner to conduct another scan may be any of the following controls, for example: a control for suggesting the user to carry out photography again; and a control for automatically performing photography again (a control for automatically shifting to re-photographing).

According to this configuration, it is possible to smoothly shift to re-photographing (re-scanning) in the case where an image group of a satisfactory quality cannot be acquired by one time of scan.

The slit lamp microscope 1 of the present aspect example may further include the image set forming processor 82. The image set forming processor 82 is configured to execute a formation of an image set by selecting a series of images corresponding to a predetermined scan area from two or more image groups that include the image group acquired already by the scan applied to the anterior eye segment and another image group collected by another scan.

According to this configuration, in the case where two or more times of scans are applied to the anterior segment, an image set can be formed with a series of images selected from two or more image groups obtained by the two or more times of scans. This improves the possibility of obtaining an image set of satisfactory quality. For example, even in the case where a satisfactory image cannot be obtained due to the occurrence of blinking or eye movements during execution of a scan, an image obtained through another scan can be used as a replacement for a corresponding unsatisfactory image.

The image set forming processor 82 may include the selecting processor 821 configured to execute selection of an image that satisfies a predetermined condition from the two or more image groups obtained by the two or more times of scans.

This configuration makes it possible to select satisfactory images satisfying a predetermined condition in order to form an image set.

For example, the selecting processor 821 may be configured to select, from the two or more image groups, an image that includes a reflected image of the slit light projected onto the anterior segment of the subject's eye E. This makes it possible to form an image set including no images photographed during eye blinking. In other words, this make it possible to form an image set that does not include images in which the anterior eye segment is not depicted.

The selecting processor 821 may be configured to perform selection of an image from the two or more image groups by comparing adjacent images.

With this configuration, it becomes possible to form an image set including no images photographed during eye movements have been taking place. In other words, this configuration makes it possible to form an image set including no images with inconsistent relative positions.

In the present aspect example, a plurality of positions (B1 to BN) may be determined (designated) for the scan area. Further, the selecting processor 821 may be configured to perform selection of an image in such a manner as to assign one or more images to each of the plurality of positions (B1 to BN).

With this configuration, a plurality of images (F1 to FN) corresponding to the plurality of positions (B1 to BN) in the scan area can be obtained.

Some typical examples are configured to assign one image to each of the plurality of positions (B1 to BN); however, two or more images may be assigned to each of one or more of the plurality of positions (B1 to BN). In such a case, noise reduction may be performed by applying image averaging to two or more images assigned to a certain position Bn, for example. In some examples, a doctor can compare two or more images assigned to a certain position Bn to select an image(s) from the two or more images. In some examples, to a certain position Bn, two or more images photographed under mutually different conditions may be assigned. Here, examples of the conditions include wavelength, presence/absence of fluorescent agent administration, and so forth.

In the present aspect example, the controller 7 may be configured to control the scanner and the selecting processor 821 in such a manner as to alternately execute (execute by turns) application of one (or more) scan(s) to the anterior segment of the subject's eye E and selection of an image(s) from one (or more) image group(s) collected by the one (or more) scan(s). In other words, the slit lamp microscope 1 may be configured to perform alternate execution of scan application and image selection in order to acquire a series of images to be included in an image set.

In the alternate execution of the scan application and the image selection, the period of scan applications and the period of image selections may overlap in part or may be separated from each other. In other words, the repetitive scan application and the repetitive image selection may be performed partially in parallel, or may be performed exclusively in time.

The selecting processor 821 may be configured to form a tentative image set by executing image selection from one or more image groups collected by one or more times of scans already performed in the alternate execution of scan application and image selection. In other words, the selecting processor 821 may be configured to form a tentative image set from one or more image groups collected by one or more times of scans performed up to the present point of time.

Further, the selecting processor 821 may be configured to perform the following processes after application of another scan (a new scan) to the anterior segment of the subject's eye E during the alternate execution of scan application and image selection: a process of selecting an image from another image group collected by this another scan; and a process of forming another tentative image set by adding this image selected from this another image group to a past tentative image set formed based on one or more scans performed prior to this another scan. In other words, the selecting processor 821 may be configured to, each time a scan is applied to the anterior eye segment, sequentially perform image selection from an image group collected by this scan and add an image selected by this image selection to a tentative image set. More generally, the selecting processor 821 may be configured to, when another scan is applied to the anterior segment after one or more times of scans, select an image from another image group collected by this another scan and update a tentative image set by the selected image. Here, the "update" is not limited to "addition", and may also be, for example, "replacement", "synthesis (e.g., averaging), or other operations.

With such a configuration of alternately performing scan application and image selection as described above, an image set can be formed by acquiring a series of images corresponding to the scan area while sequentially selecting an image from an image group obtained from each scan application. Further, it is possible to sequentially select a satisfactory image from an image group obtained from each scan application.

The controller 7 may be configured to control the scanner and the selecting processor 821 to terminate the alternate execution of the scan application and the image selection when the number of images included in a tentative image set reaches a predetermined number. Further, the image set forming processor 82 may be configured to form an image set based on a tentative image set acquired until termination of the alternate execution of the scan application and the image selection.

This configuration makes it possible to automatically terminate the alternate execution of the scan application and the image selection subject to acquisition of a sufficient number of images for forming an image set. Therefore, photography and image set formation can be performed efficiently.

The controller 7 may be configured to control the scanner and the selecting processor 821 to terminate alternate execution of the scan application and the image selection when the number of times of the repetitions in the alternate execution of the scan application and the image selection reaches a predetermined number. Further, the image set forming processor 82 may be configured to form an image set based on a tentative image set acquired until termination of the alternate execution of the scan application and the image selection.

This configuration makes it possible to prevent photography for image set formation from taking long time.

Instead of the alternate execution of the scan application and the image selection as described above, the slit lamp microscope 1 may be configured to perform image selection after performing a plurality of times of scans in a row. More specifically, the controller 7 may be configured to execute the following controls in the case where the quality of an image group collected by the scanner is assessed to be not satisfactory: a control of the scanner in such a manner as to apply two or more times of scans to the anterior eye segment; and then a control of the selecting processor 821 in such a manner as to select an image(s) from three or more image groups that include two or more image groups collected by the two or more times of scans and an image group collected by a scan(s) performed prior to the two or more times of scans. Further, the image set forming processor 82 may be configured to form an image set that includes a series of images thus selected by the selecting processor 821.

The slit lamp microscope 1 of the present aspect example may further include the image set assessing processor 83 configured to execute an assessment of the quality of the image set formed by the image set forming processor 82. In some examples, the image set assessing processor 83 may be configured to be capable of performing an assessment of any of the following condition items for the series of images included in the image set: the arrangement order of the series of images; lack or omission of an image in the series of images; and misalignment of the series of images. This assessment may be executed by analyzing the series of images in the image set. For example, the image set assessing processor 83 may execute a quality assessment of the series of images based on a landmark in a series of frames. The landmark may be an image region corresponding to a tissue or a site such as the cornea, the iris, or the pupil.

By performing such an assessment of an image set, it becomes possible to prepare an image set having a satisfactory quality that makes it possible for a doctor or an image interpretation apparatus to achieve effective performance of image interpretation.

The slit lamp microscope 1 of the present aspect example may further include an output unit. Further, the controller 7 may be configured to perform a control of the output unit to output an image set when the image set assessing processor 83 has assessed that the quality of the image set is satisfactory. Here, the output unit may include any of the following options, for example: the communication device 9 for transmitting the image set to an external device; a storage (e.g., database) for storing the image set; a recording device (e.g., data writer, drive device) for writing (recording) the image set on a recording medium; and a printer for recording (printing) information included in the image set on a printing medium.

This configuration makes it possible to output an image set having a satisfactory quality, in order to provide the image set to a doctor or an image interpretation apparatus.

In the present aspect example, the controller 7 may be configured to perform a control for acquiring another image set when the image set assessing processor 83 has assessed that the quality of the image set is not satisfactory. This control may be, for example, a control for suggesting a user to conduct re-acquisition of images (re-photographing), or a control for automatically starting re-acquisition of images (re-photographing) (another execution of scan application and image set formation).

The slit lamp microscope 1 of the present aspect example makes it possible to implement scanning of anterior eye segment with slit light by means of the following configuration. That is, the scanner includes the illumination system 2, the photography system 3, and the movement mechanism 6. The illumination system 2 is configured to project the slit light onto the anterior segment of the subject's eye E. The photography system 3 is configured to perform photography of the anterior segment from a direction different from the illumination system 2. The movement mechanism 6 is configured to move the illumination system 2 and the photography system 3. The photography system 3 performs repetitive photography (repetitive acquisition of images) in parallel with movement of the illumination system 2 and the photography system 3 performed by the movement mechanism 6. This repetitive photography is, for example, moving image photography at a photographing rate set in advance.

The movement mechanism 6 of the present aspect example may be configured to move the illumination system 2 and the photography system 3 in the X direction for anterior eye segment scanning with slit light. The movement mechanism 6 of the present aspect example may be capable of moving the illumination system 2 and the photography system 3 in a three dimensional manner for alignment.

Furthermore, the slit lamp microscope 1 of the present aspect example may have a function as a Scheimpflug camera, for example, in order to make it possible to photograph an area from the anterior surface of the cornea to the posterior surface of the crystalline lens by a single shot. For this purpose, the photography system 3 may include the optical system 4 and the image sensor 5. The optical system 4 is configured to direct light coming from the anterior eye segment onto which the slit light is projected. The image sensor 5 includes a light detecting plane and is configured to receive the light directed by the optical system 4. In addition, the slit lamp microscope 1 may be configured in such a manner that the subject plane along the optical axis of the illumination system 2, the optical system 4, and the image sensor 5 (the light detecting plane) satisfy the Scheimpflug condition.

In the present aspect example, the configuration and operation of the image group assessing processor 81 may be freely selected or determined. The image group assessing processor 81 may include any one or more of the following preferable examples (the image group assessing processors 81A, 81B, 81C).

The image group assessing processor 81A is configured to execute an assessment of a quality of an image group collected by the scanner, using the inference model 812A constructed by machine learning in which training data including a plurality of anterior segment images is used.

Here, a label may be attached to each of the plurality of anterior segment images included in the training data. The label shows whether interpretation of a corresponding image is possible or impossible. Furthermore, the inference model 812A may be constructed by supervised learning that uses the training data and configured to receive an input of an image obtained by scanning an anterior segment with slit light and to output image interpretation possibility.

When an image group (or an image set) acquired by the slit lamp microscope 1 is provided to an image interpretation apparatus equipped with an artificial intelligence engine configured to execute image interpretation using an inference model, the inference model 812A provided in the slit lamp microscope 1 may be the same inference model or a similar inference model to the one provided in the image interpretation apparatus.

The image group assessing processor 81B includes the three dimensional image constructing processor 811B, the comparing processor 812B, and the assessing processor 813B. The three dimensional image constructing processor 811B is configured to execute construction of a three dimensional image from the image group collected by the scanner. The comparing processor 812B is configured to execute a comparison of the three dimensional image constructed by the three dimensional image constructing processor 811B with one or more predetermined reference three dimensional images. The assessing processor 813B is configured to execute an assessment of a quality of this image group based on a result of the comparison obtained by the comparing processor 812B.

Here, the one or more predetermined reference three dimensional images used as a reference by the comparing processor 812B may include either one of or both the following images: one or more reference three dimensional images corresponding to one or more normal eyes; and one or more reference three dimensional images corresponding to one or more affected eyes. In other words, the one or more predetermined reference three dimensional images referred to by the comparing processor 812B may include: only one or more reference three dimensional images corresponding to one or more normal eyes; only one or more reference three dimensional images corresponding to one or more normal eyes; or both one or more reference three dimensional images corresponding to one or more normal eyes and one or more reference three dimensional images corresponding to one or more normal eyes.

Further, the comparing processor 812B may be configured to execute image matching of the three dimensional image constructed by the three dimensional image constructing processor 811B with each of the one or more predetermined reference three dimensional images, thereby calculating a value of a predetermined parameter. In addition, the assessing processor 813B may be configured to execute the assessment of the quality of the image group based on the parameter value calculated by the comparing processor 812B.

The image group assessing processor 81C includes the assessment data generating processor 811C and the assessing processor 812C. The assessment data generating processor 811C is configured to execute generation of image quality assessment data from an image included in the image group collected by the scanner. The assessing processor 812C is configured to execute the assessment of the quality of the image group based on the image quality assessment data generated by the assessment data generating processor 811C.

Here, the assessment data generating processor 811C may be configured to execute the following processes: a process of identifying a tissue image region, which is in the image included in the image group collected by the scanner, corresponding to a tissue of the anterior segment, and identifying a background region; a process of generating the first histogram showing a brightness frequency distribution in the tissue image region; a process of generating the second histogram showing a brightness frequency distribution in the background region; and a process of calculating an image quality assessment value, as the image quality assessment data, based on the first histogram and the second histogram.

Second Aspect Example

Figure 8:
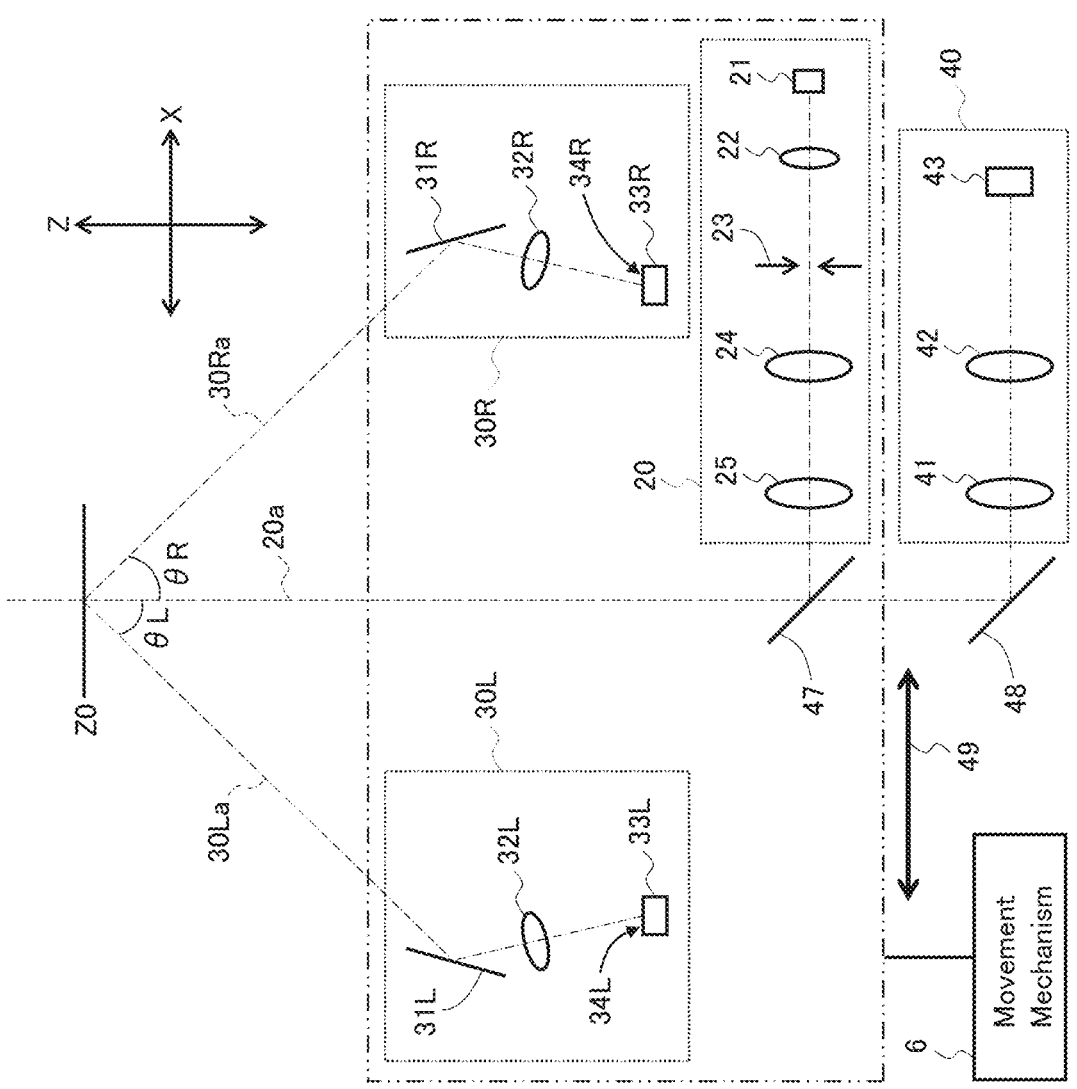
FIG. 8 is a schematic diagram illustrating a configuration of a slit lamp microscope according to an aspect example.

The present aspect example gives a description of a configuration of an optical system applicable to the slit lamp microscope 1 of the first aspect example and an application of this optical system. FIG. 8 shows an example of the configuration of the optical system according to the present aspect example. In addition to the group of elements shown in FIG. 8, the configuration according to the present aspect example may further include any element described in other aspect examples. For example, the present aspect example may further include the controller 7, the data processor 8, the communication device 9, and other elements of the first aspect example. The present aspect example may employ any of the matters and items according to the first aspect example unless otherwise mentioned.

The illumination system 20 shown in FIG. 8 is an example of the illumination system 2 of the first aspect example, and the pair of the left photography system 30L and the right photography system 30R is an example of the photography system 3. In the following, the illumination system 20 may be referred to as the illumination system 2, and the left photography system 30L and/or the right photography system 30R may be referred to as the photography system 3. Note that some aspect examples may include only one of the left photography system 30L and the right photography system 30R, and this single photography system may be regarded as an example of the photography system 3. The reference character 20a denotes the optical axis of the illumination system 20 (referred to as the illumination optical axis), the reference character 30La denotes the optical axis of the left photography system 30L (referred to as the left photography optical axis), and the reference character 30Ra denotes the optical axis of the right photography system 30R (referred to as the right photography optical axis). The orientation of the left photography optical axis 30La and the orientation of the right photography optical axis 30Ra are different from each other. The angle formed by the illumination optical axis 20a and the left photography optical axis 30La is denoted by θL, and the angle formed by the illumination optical axis 20a and the right photography optical axis 30Ra is denoted by θR. The angle θL and the angle θR may be equal to or different from each other. The illumination optical axis 20a, the left photography optical axis 30La, and the right photography optical axis 30Ra intersect at one point. As with FIG. 1, the Z coordinate of the intersection is denoted by Z0.

The movement mechanism 6 is capable of moving the illumination system 20, the left photography system 30L, and the right photography system 30R in the direction denoted by the arrow 49 (X direction). In some typical examples, the illumination system 20, the left photography system 30L, and the right photography system 30R are mounted on a stage that is movable at least in the X direction, and the movement mechanism 6 moves the movable stage under a control signal from the controller 7.

The illumination system 20 is configured to project slit light onto the anterior segment of the subject's eye E. Similar to an illumination system of a conventional slit lamp microscope, the illumination system 20 includes the illumination light source 21, the positive lens 22, the slit forming member 23, and the group of objective lenses 24 and 25 in the order from the side far from the subject's eye E.

The illumination light output from the illumination light source 21 (typically, visible light) is refracted by the positive lens 22 and projected onto the slit forming member 23. Part of the illumination light projected onto the slit forming member 23, passes through the slit formed by the slit forming member 23 and becomes slit light. The slit light generated by the slit forming member 23 is refracted by the group of objective lenses 24 and 25, and then reflected by the beam splitter 47, and projected onto the anterior segment of the subject's eye E.

The left photography system 30L includes the reflector 31L, the imaging lens 32L, and the image sensor 33L. The reflector 31L and the imaging lens 32L direct, to the image sensor 33L, light coming from the anterior segment onto which the slit light is being projected by the illumination system 20 (that is, light coming from the anterior segment and traveling in the direction toward the left photography system 30L).

The light traveling in the direction toward the left photography system 30L from the anterior eye segment corresponds to light that not only comes from the anterior eye segment onto which the slit light is being projected but also travels in the direction away from the illumination optical axis 20a. The reflector 31L is arranged to reflect the light toward a direction approaching the illumination optical axis 20a. The imaging lens 32L refracts the light reflected by the reflector 31L and forms an image on the light detecting plane 34L of the image sensor 33L. The image sensor 33L receives and detects the light by the light detecting plane 34L.

As in the first aspect example, the left photography system 30L performs repetitive photography in parallel with movement of the illumination system 20, the left photography system 30L, and the right photography system 30R performed by the movement mechanism 6. Such operations acquire a plurality of anterior segment images (image group).

Also as in the first aspect example, the subject plane along the illumination optical axis 20a, the optical system that includes the reflector 31L and the imaging lens 32L, and the light detecting plane 34L satisfy the Scheimpflug condition. More specifically, considering the deflection of the optical path of the photography system 30L by the reflector 31L, the YZ plane (including the subject plane) passing through the illumination optical axis 20a, the principal plane of the imaging lens 32L, and the light detecting plane 34L intersect on the same straight line. As a result, the left photography system 30L may perform photography with all positions in the subject plane (e.g., the area from the anterior corneal surface to the posterior crystalline lens surface) in focus.

The right photography system 30R includes the reflector 31R, the imaging lens 32R, and the image sensor 33R. Like the left photography system 30L, the right photography system 30R directs light coming from the anterior eye segment onto which the slit light is being projected by the illumination system 20 to the light detecting plane 34R of the image sensor 33R by the reflector 31R and the imaging lens 32R. Further, as with the left photography system 30L, the right photography system 30R acquires a plurality of anterior segment images (image group) by performing repetitive photography in parallel with movement of the illumination system 20, the left photography system 30L, and the right photography system 30R performed by the movement mechanism 6. As in the case of the left photography system 30L, the subject plane along the illumination optical axis 20a, the optical system that includes the reflector 31R and the imaging lens 32R, and the light detecting plane 34R satisfy the Scheimpflug condition.

The controller 7 may perform synchronization between the repetitive photography carried out by the left photography system 30L and the repetitive photography carried out by the right photography system 30R. With this synchronization, a correspondence (association, relationship) can be made between a plurality of anterior segment images obtained by the left photography system 30L and a plurality of anterior segment images obtained by the right photography system 30R. This correspondence is a temporal correspondence (chronological correspondence), and more specifically, it is a correspondence for establishing a pair of images acquired at substantially the same time by the left photography system 30L and the right photography system 30R.

In some alternative examples, the controller 7 or the data processor 8 may execute a process of determining a correspondence between a plurality of anterior segment images obtained by the left photography system 30L and a plurality of anterior segment images obtained by the right photography system 30R. For example, the controller 7 or the data processor 8 may be configured to form pairs of images from anterior segment images sequentially input from the left photography system 30L and anterior segment images sequentially input from the right photography system 30R, in accordance with their input timings.

The present aspect example further includes the moving image acquisition unit 40. The moving image acquisition unit 40 acquires a moving image of the anterior segment of the subject's eye E from a fixed position in parallel with the photography (image acquisition) performed by the left photography system 30L and the right photography system 30R. This acquisition of a moving image from the fixed position indicates that the moving image acquisition unit 40 is not moved while the illumination system 20, the left photography system 30L and the right photography system 30R are moved for the anterior segment scanning. Note that the moving image acquisition unit 40 is also capable of acquiring a still image.

The moving image acquisition unit 40 of the present aspect example is arranged coaxially with the illumination system 20; however, possible arrangements are not limited to this example. For example, the moving image acquisition unit 40 may be arranged non-coaxially with the illumination system 20. Further, an optical system may be provided which projects, onto the anterior eye segment, illumination light of a wavelength band(s) detectable by the moving image acquisition unit 40.

The light transmitted through the beam splitter 47 is reflected by the reflector 48 and enters the moving image acquisition unit 40. The light that has entered the moving image acquisition unit 40 is refracted by the objective lens 41 and then forms an image on the light detecting plane of the image sensor 43 by the imaging lens 42. The image sensor 43 may be an area sensor. The image sensor 43 is capable of detecting one of or both wavelength bands of visible light and infrared light, for example.

In the case where the moving image acquisition unit 40 is employed, movement of the subject's eye E may be monitored and tracking may be performed. Further, alignment may be performed using the moving image acquisition unit 40.

The beam splitter 47 may be a dichroic mirror or a half mirror, for example, depending on the output wavelength of the illumination system 20 and the detectable wavelength of the moving image acquisition unit 40.

Some features, some actions, and some advantageous effects of the slit lamp microscope of the present aspect example will be described.

The present aspect example provides the pair of the left photography system 30L and the right photography system 30R as an example of the photography system 3 of the first aspect example. The pair of the left photography system 30L and the right photography system 30R is an example of the pair of the first photography system and the second photography system described above. The left photography system 30L includes the reflector 31L and the imaging lens 32L (first optical system), and the image sensor 33L (first image sensor). The first optical system is configured to direct the light coming from the anterior eye segment onto which the slit light is being projected. The first image sensor includes the light detecting plane 34L (first light detecting plane) that receives the light directed by the first optical system. Likewise, the right photography system 30R includes the reflector 31R and the imaging lens 32R (second optical system) and the image sensor 33R (second image sensor). The second optical system is configured to direct the light coming from the anterior eye segment onto which the slit light is being projected. The second image sensor includes the light detecting plane 34R (second light detecting plane) that receives the light directed by the second optical system.

The orientation of the optical axis of the left photography system 30L (the left photography optical axis 30La) and the orientation of the optical axis of the right photography system 30R (the right photography optical axis 30Ra) are different from each other. Further, the subject plane along the optical axis of the illumination system 20 (the illumination optical axis 20a), the reflector 31L and the imaging lens 32L, and the light detecting plane 34L satisfy the Scheimpflug condition. Similarly, the subject plane, the reflector 31R and the imaging lens 32R, and the light detecting plane 34R satisfy the Scheimpflug condition.

The left photography system 30L acquires the first image group by performing repetitive photography in parallel with the movement of the illumination system 20, the left photography system 30L, and the right photography system 30R performed by the movement mechanism 6. Likewise, the right photography system 30R acquires the second image group by performing repetitive photography in parallel with the movement of the illumination system 20, the left photography system 30L, and the right photography system 30R performed by the movement mechanism 6.

The controller 7 may be configured to perform a control of the illumination system 20, the left photography system 30L, the right photography system 30R, and the movement mechanism 6 in such a manner that, for example, the left photography system 30L and the right photography system 30R individually apply a single scan to the anterior segment of the subject's eye E in parallel with one another. The data processor 8 may be configured to form a single image group by selecting, from the pair of the left image group and the right image group collected by the parallel scans, a series of images corresponding to the scan area. The image group assessing processor 81 is configured to execute a quality assessment of the image group formed. In the case where the image group assessing processor 81 determines that the quality of this image group is satisfactory, the controller 7 is configured to perform a control of the communication device 9 to transmit the image group to a predetermined external device.

In the case where the image group assessing processor 81 determines that the quality of this image group is not satisfactory, the controller 7 is configured to perform a control of the illumination system 20, the left photography system 30L, the right photography system 30R, and the movement mechanism 6 to apply another scan (one or more times of scans) to the anterior segment of the subject's eye E. With this additional scan, the left photography system 30L collects one or more first image groups corresponding to the one or more times of scans, and the right photography system 30R collects one or more second image groups corresponding to the one or more times of scans. For example, the image set forming processor 82 may be configured to execute both of the following processes: a process of forming the first image set by selecting the first series of images corresponding to the scan area, from among the two or more first image groups acquired by the first scan and the additional scan; and a process of forming the second image set by selecting the second series of images corresponding to the scan area, from among the two or more second image groups acquired by the first scan and the additional scan. In some alternative examples, the image set forming processor 82 may be configured to form an image set by selecting a series of images corresponding to the scan area, from among the two or more first image groups and the two or more second image groups acquired by the first scan and the additional scan. Any of the matters and items, such as the configurations, controls, processes, actions, and functions described in the first aspect example, may be combined with the second aspect example.

According to the second aspect example, moving images of the anterior eye segment onto which the slit light is being projected can be acquired respectively from mutually different directions. There may be a case where an image (first image) acquired by one of the photography systems contains an artifact while the other image (second image) substantially simultaneously acquired with the first image by the other photography system does not contain any artifact. Further, there may be a case where a pair of images substantially simultaneously acquired by the two photography systems both contain artifacts, and the artifact in one of the images overlaps a region of interest (e.g., a region onto which the slit light is being projected (slit light projected region)) while the artifact in the other image does not overlap a region of interest. Therefore, the present aspect example is capable of improving the possibility of being able to obtain satisfactory (proper, eligible, preferable) images. As a result, the present aspect example becomes capable of further improving the probability of being able to obtain an image group and/or image set of a satisfactory quality.

Note that, in addition to the first photography system and the second photography system, the photography system 3 may include the third photography system, . . . , K-th photography system (where K is an integer equal to or greater than 3) each of which has a similar configuration as the first or second photography system. Although such a configuration makes the structure of the optical system more complicated, this configuration makes it possible to further improve the probability of being able to obtain an image group and/or image set of a good quality. Those who intend to implement the present aspect example may design a slit lamp microscope in view of these trade-off matters and items (that is, the complexity of the optical system and the probability of being able to obtain an image set having a high quality).

The left photography system 30L of the present aspect example includes the reflector 31L and the imaging lens 32L. The reflector 31L is configured to reflect the light coming from the anterior segment onto which the slit light is being projected and traveling in a direction away from the illumination optical axis 20a, toward a direction approaching the illumination optical axis 20a. Further, the imaging lens 32L is configured to form an image of the light reflected by the reflector 31L on the light detecting plane 34L. Here, the imaging lens 32L includes one or more lenses.

Likewise, the right photography system 30R includes the reflector 31R and the imaging lens 32R. The reflector 31R is configured to reflect the light coming from the anterior segment onto which the slit light is being projected and traveling in a direction away from the illumination optical axis 20a, toward a direction approaching the illumination optical axis 20a. Further, the imaging lens 32R is configured to form an image of the light reflected by the reflector 31R on the light detecting plane 34R. Here, the imaging lens 32R includes one or more lenses.

With such a configuration, reducing the size of the apparatus can be achieved. More specifically, taking into account the fact that the images acquired by the image sensor 33L (33R) are output through a cable extending from the surface on the opposite side of the light detecting plane 34L (34R), the present configuration allows a cable to be arranged from the back surface of the image sensor 33L (33R) located relatively close to the illumination optical axis 20a toward the direction opposite to the subject's eye E. As a result of this, cable routing can be performed in a preferable manner, making it possible to reduce the size of the apparatus.

In addition, the present configuration allows the angle θL and the angle θR to be designed large. This increases the possibility of an image acquired by one of the photography systems not containing any artifact although a corresponding image acquired by the other photography system contains an artifact. Here, the corresponding image is an image acquired by the other photography system substantially at the same time as the image acquired by the one of the photography systems. In addition, even though artifacts are contained in both of a pair of images substantially simultaneously acquired by the both photography systems and an artifact in one of the images overlaps a region of interest (e.g., a region onto which slit light is being projected (slit light projected region)), designing the angle θL and the angle θR to be large can reduce the possibility of an artifact in the other image overlapping a region of interest.

The present aspect example includes the moving image acquisition unit 40. The left photography system 30L and the right photography system 30R each perform repetitive photography of the anterior eye segment in parallel with the movement of the illumination system 20, the left photography system 30L and the right photography system 30R performed by the movement mechanism 6. In parallel with such repetitive photography, the moving image acquisition unit 40 acquires a moving image of the anterior segment from a fixed position.

Such a configuration allows acquiring a moving image from the fixed position (e.g., from the front position with respect to the subject's eye E) in parallel with the anterior eye segment scanning with slit light. This makes it possible to grasp the state of the subject's eye E during the scanning as well as to perform a control depending on the state of the subject's eye E.

For example, in the case where the slit lamp microscope of the present aspect example includes the image group assessing processor 81 (the image set assessing processor 83) of the first aspect example, the slit lamp microscope of the present aspect example may be capable of assessing whether or not an image group(s) (image set(s)) acquired by the left photography system 30L and/or the right photography system 30R are/is of a quality good enough for image interpretation. In the present aspect example, combining the image group assessing processor 81 (the image set assessing processor 83) with the moving image acquisition unit 40 makes it possible to perform the operations described in the following. It should be noted that the same or similar operations may also be implemented by using two or more anterior segment cameras for stereo alignment or using like imaging methods and techniques.

The moving image acquisition unit 40 performs acquisition of a moving image of the anterior segment of the subject's eye E from a fixed position in parallel with application of a scan to the anterior segment. This moving image acquisition is performed under the control of the controller 7, for example. In other words, in order to perform the anterior segment scanning of the subject's eye E, the controller 7 may execute an interlocking control of the illumination system 2 (the illumination system 20), the photography system 3 (the left photography system 30L and/or the right photography system 30R), the movement mechanism 6, and the moving image acquisition unit 40.

In this interlocking control, the controller 7 may execute synchronization of the photographing rate of the photography system 3 and the photographing rate of the moving image acquisition unit 40 with each other. For example, the photographing rate of the photography system 3 and the photographing rate of the moving image acquisition unit 40 are controlled to be equal to one another, and the photographing timing of the photography system 3 and the photographing timing of the moving image acquisition unit 40 are controlled to coincide with one another. With such controls, a frame group acquired by the photography system 3 and the frame group acquired by the moving image acquisition unit 40 during scanning can be associated with each other in terms of time.

Even when one of or both the photographing rates and the photographing timings are different, it is possible to associate a frame group acquired by the photography system 3 and a frame group acquired by the moving image acquisition unit 40 during scanning with each other in terms of time. This association can be made, for example, by ignoring a time difference within a permissible range determined in advance.

It can be considered that two frames (one is a frame obtained by the photography system 3 and the other is a frame obtained by the moving image acquisition unit 40) paired with each other in terms of chronological correspondence have been acquired at substantially the same time. Therefore, when a pair of temporally (chronologically) associated frames is considered (treated), positional differences between these frames due to eye movement can be ignored.

Under such a premise, the image group assessing processor 81 (the image set assessing processor 83) may be configured to perform a quality assessment of a series of images included in an image group (image set) based on a moving image (frame group) acquired by the moving image acquisition unit 40.

In such examples, the image group assessing processor 81 (the image set assessing processor 83) may be configured to perform an assessment of a quality of the image group (image set) based on a correspondence between the series of images included in the image group (image set) and a series of frames included in the moving image acquired by the moving image acquisition unit 40. In other words, the image group assessing processor 81 (the image set assessing processor 83) may be configured to perform a quality assessment of the image group (image set) based on a temporal correspondence (chronological correspondence) between a frame group obtained by the photography system 3 and a frame group acquired by the moving image acquisition unit 40. In addition, the image group assessing processor 81 (the image set assessing processor 83) may be configured to perform a quality assessment of the image group (image set) based on a landmark in the series of frames and the correspondence described above.

A specific example is described below. In the present example, the frame group F1 to FN (described above) have been acquired by the photography system 3 and a frame group D1 to DN have been acquired by the moving image acquisition unit 40 in parallel with the acquisition of the frame group F1 to FN. In addition, for any $n=1, 2, \ldots, N$, the frame Fn and the frame Dn have been associated with each other.

The image group assessing processor 81 (the image set assessing processor 83) identifies a landmark in each of the frame group D1 to DN. This landmark may be, for example, an image region corresponding to the iris (iris region).

Next, the image group assessing processor 81 (the image set assessing processor 83) determines an arrangement order (spatial arrangement order) of the frame group D1 to DN based on the positions of the N number of landmarks identified respectively from the frame group D1 to DN (e.g., based on changes in spatial positions of the identified landmarks).

As mentioned above, the frame group D1 to DN are arranged in a temporal (chronological) manner in accordance with the ascending order $n=1, 2, \ldots, N$ (temporal arrangement order or chronological arrangement order). If the temporal arrangement order (chronological arrangement order) and the spatial arrangement order are different from each other, there is a possibility that the order of the frames has been changed and/or positional deviation has occurred due to the influence of eye movement. In addition, there is a possibility that skipping (lack, omission) of a frame has occurred due to the influence of blinking.

In the case where such a defect is detected, that is, in the case where the fact is detected that the temporal arrangement order (chronological arrangement order) and the spatial arrangement order are different from each other, the image group assessing processor 81 (the image set assessing processor 83) determines that the quality of this image group (image set) is not satisfactory.

With such a configuration, the slit lamp microscope 1 is capable of acquiring a moving image in which a wide area of the anterior eye segment is depicted (at least a wide area in the X direction and a wide area in the Y direction) in parallel with anterior segment scanning with slit light, and detecting a defect in a series of images included in the image group (image set) using the moving image acquired.

Each image of the series of images included in the image group (image set) is an image that extends in the depth direction (the Z direction). Therefore, it is necessary to employ image processing (image analysis) as in the first aspect example, in order to recognize the locations, arrangement, layout, or the like of the series of images in the X and Y directions orthogonal to the Z direction on the basis of the series of images itself.

The present example implements, without applying image analysis to a series of images, a quality assessment of a series of images using a moving image that is separately acquired in parallel with scanning. The assessment items in the present example may be any of an arrangement order of a series of images, lack or omission of an image in a series of images, and misalignment of a series of images, as in the first aspect example. Further, the assessment processing of the present example may be combined with any of the assessment processes described in the first aspect example.

Another application of the moving image acquisition unit 40 is described below. The purpose of the present example is to, when, for example, two or more times of additional scans are to be performed after a quality of an image group collected by the first scan is determined to be not satisfactory, prevent misalignment (positional deviation) of the subject's eye E between scans by performing adjustment of the commencement timings of the two or more times of additional scans.

In the present example as well, the moving image acquisition unit 40 performs photography of the anterior segment of the subject's eye E from a fixed position. The controller 7 is configured to control the scanner to commence the second scan in response to an event that the moving image acquisition unit 40 has acquired an image substantially the same image as a reference image that has been acquired by the moving image acquisition unit 40 in response to commencement of the first scan of the two or more times of additional scans.

The following is a more specific description. Any one of two or more scans applied to the anterior eye segment to form an image set is referred to as the first scan. The first scan of the present example may be the scan executed first among the two or more scans.

To begin with, the controller 7 saves an image acquired by the moving image acquisition unit 40 at the commencement timing of the first scan (referred to as a reference image). The reference image may be, for example, a frame captured at a point of time closest to the point of time of the commencement of the first scan, among a frame group of a moving image whose acquisition has started before the commencement of the first scan. In some alternative examples, the moving image acquisition unit 40 may acquire, under the control of the controller 7, a reference image by taking a still image of the anterior eye segment at the commencement point of time of the first scan. This commencement point of time of the first scan may be any of the following options: a point of time immediately before the commencement point of time of the first scan; a point of time that coincides with the commencement point of time of the first scan; and a point of time immediately after the commencement point of time of the first scan.

Any scan that is performed after the first scan (referred to as the second scan) is commenced at a point of time during the moving image photography of the anterior segment is being performed by the moving image acquisition unit 40. The controller 7 (or the data processor 8) compares the frames sequentially acquired by the moving image acquisition unit 40 with the reference image. This comparison may include any image processing, such as segmentation to identify a landmark, image matching, image correlation, or the like.

When it is determined that substantially the same frame as the reference image is obtained, the controller 7 controls the illumination system 2, the photography system 3, and the movement mechanism 6 to start the second scan.

The slit lamp microscope of the present example continues repetitive execution of the series of processes described above until the number of scan applications to the anterior eye segment reaches the number of scan repetitions for image set formation determined in advance. The present example thus configured can reduce misalignment of the subject's eye E between scans and therefore prevent the quality of an image set from deteriorating due to eye movements. In addition, the present example makes it possible to improve the efficiency and facilitation of image selection.

Figure 9A:
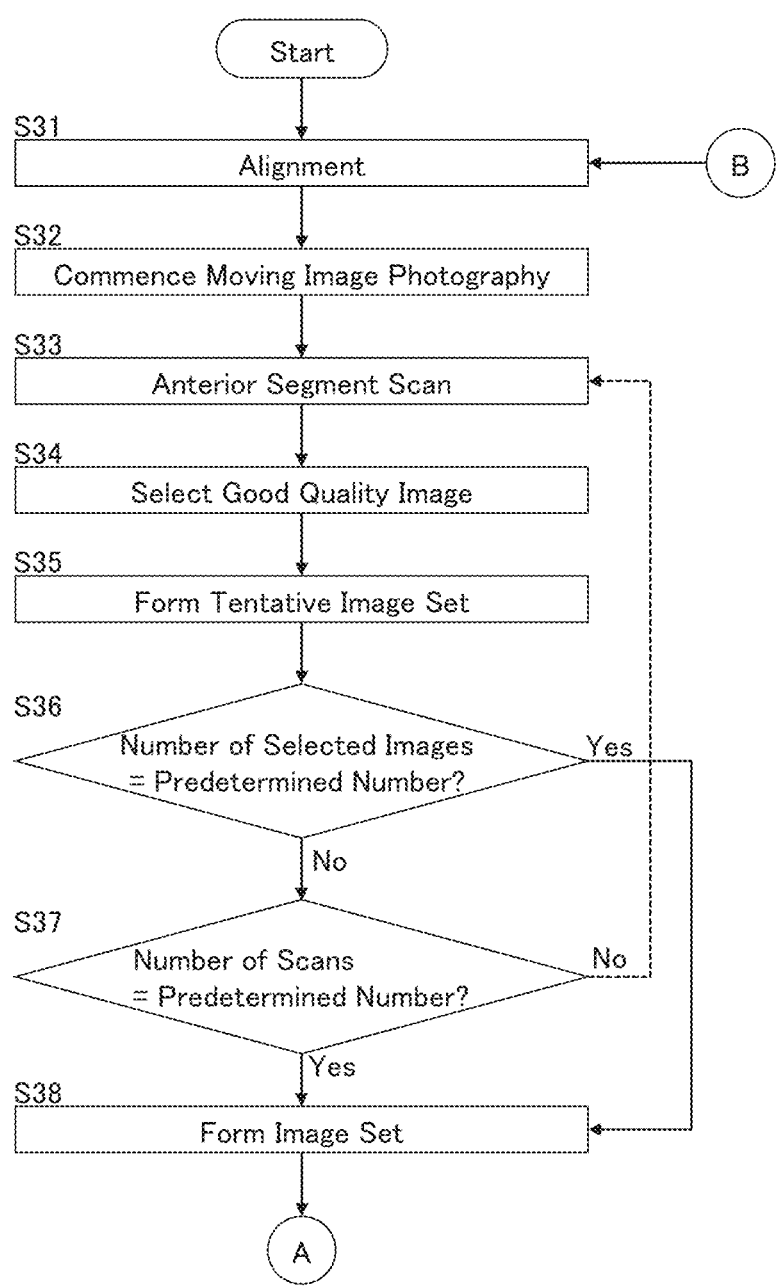
FIG. 9A is a flowchart illustrating an operation of a slit lamp microscope according to an aspect example.
Figure 9B:
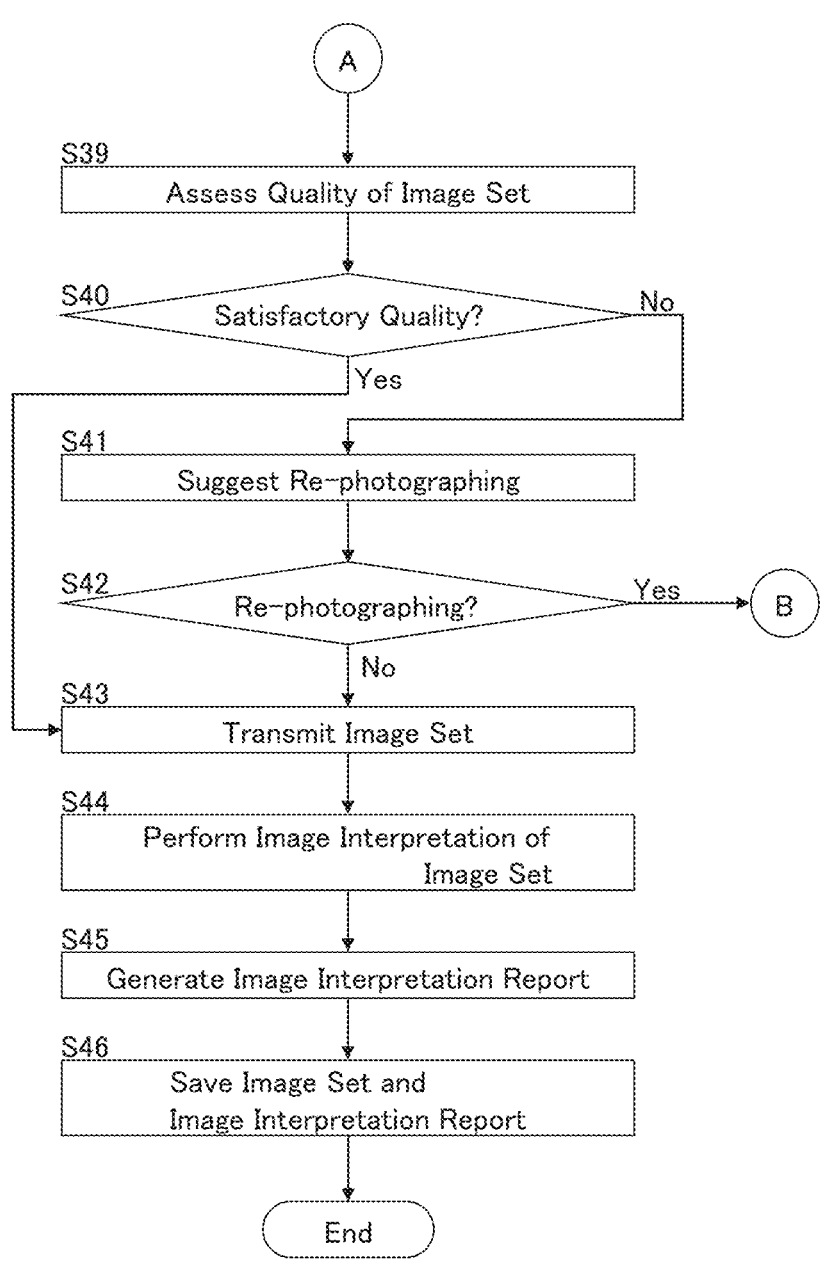
FIG. 9B is a flowchart illustrating an operation of a slit lamp microscope according to an aspect example.

Now described is the operation and the usage mode of the slit lamp microscope of the present aspect example. FIG. 9A and FIG. 9B show an example of the operation and the usage mode. A premise is made here that the various preparation processes described in the operation example of the first aspect example (that is, the operations performed prior to the step S1 in FIG. 6) have already been performed. Further, it is understood that the alignment (the step S1 or the step S11), the first scan (the step S2 or the step S12), and the assessment of a quality of an image group (the step S3 or the step S13) in the operation examples of the first aspect have already been performed. In addition, it is also understood that the quality of the image group is determined to be not satisfactory in the step S3 or the step S13 (that is, the step S4 is "No" or the step S14 is "No"). The present example initiates the step S31 in FIG. 9A when "No" is issued in the step S4 or when "No" is issued in the step S14, for example.

In the present example, it is supposed that none of the series of images included in the image group acquired in the step S2 or the step S12 has been assessed to be of satisfactory quality. Therefore, the image set formed by the operation shown in FIG. 9A and FIG. 9B does not include the images obtained in the step S2 or the step S12.

It should be noted that in the case where any one or more images of the series of images included in the image group collected in the step S2 or the step S12 is assessed to be of a satisfactory quality, the present example may form an image set including that image. An operation performed in this case could be inferred by those skilled in the art from the operation shown in FIG. 9A and FIG. 9B.

Further, in the present example, the number of images obtained by a single anterior segment scan (that is, the number of images included in an image group) is 256, and the number of images composing a series of images included in an image set is also 256. The upper limit of the number of times of scan repetitions is set to five. The present aspect example may employ any of the matters and items according to the first aspect example unless otherwise mentioned.
(S31: Alignment)

First, alignment is performed in the same manner as in the step S1 of the first aspect example. As a result of the alignment, the illumination system 2 (the illumination system 20) and the photography system 3 (either one of or both the left photography system 30L and the right photography system 30R) are placed at a position corresponding to the scan start position, and the moving image acquisition unit 40 is placed at a front position facing the subject's eye E, for example.

(S32: Commence Moving Image Photography)

After the completion of the alignment, the moving image acquisition unit 40 commences moving image photography of the anterior eye segment. The photographing rate of this moving image photography may be equal to the photographing rate of the photography system 3 in the anterior segment scan described later.

The illumination system 2 and the photography system 3 are moved for the anterior segment scan while the moving image acquisition unit 40 performs the moving image photography of the anterior eye segment from a fixed position. Further, when the anterior segment scan is performed in parallel with the moving image photography, a correspondence is made between an image group collected by the anterior segment scan and a frame group collected by the moving image acquisition unit 40 in the same manner as described above.

The commencement timing of the moving image photography may be determined accordingly. For example, the commencement timing may be before or during the execution of the alignment.

(S33: Anterior Segment Scan)

Similar to the first aspect example, the slit lamp microscope 1 conducts scanning of the anterior segment of the subject's eye E by combining the projection of the slit light performed by the illumination system 2, the moving image photography performed by the photography system 3, and the movement of the illumination system 2 and the photography system 3 performed by the movement mechanism 6.

The present example acquires 256 images through a single scan (a scan from the scan start position to the scan end position). 256 images (an image group) obtained by the first scan are denoted by H1(1) to H1(256), respectively. The first scan refers to a scan performed in the step S33 of the first time and the same applies hereinafter. The 256 images H1(1) to H1(256) are assigned to 256 positions ordered in a scan area, respectively. This scan area is an area in the X direction whose one end is the scan start position and the other end is the scan end position.

(S34: Select Good Quality Image)

The selecting processor 821 selects an image that satisfies a predetermined image selection condition from the 256 images H1(1) to H1(256) acquired in the step S33 in the same manner as in the first aspect example.

Figure 10A:
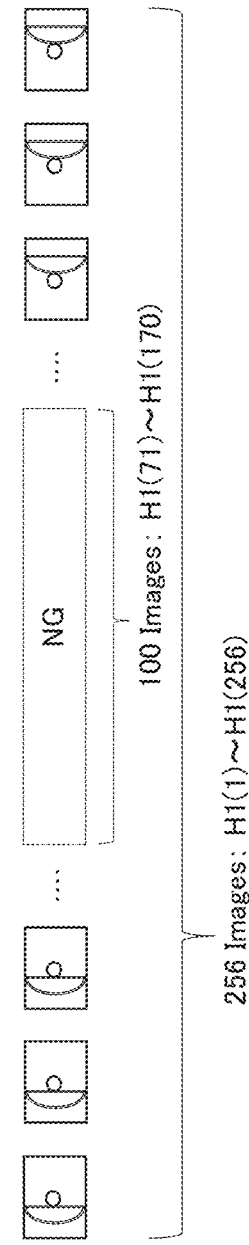
FIG. 10A is a schematic diagram for describing an operation of a slit lamp microscope according to an aspect example.

As shown in FIG. 10A, the present example makes a premise that the 100 images H1(71) to H1(170) of the 71st to the 170th images do not satisfy the image selection condition, and the 156 images H1(1) to H1(70) and H1(171) to H1(256) of the first to the 70th images and the 171st to the 256th images satisfy the image selection condition. In this case, the selecting processor 821 selects the 156 images H1(1) to H1(70) and H1(171) to H1(256) of the first to the 70th images and the 171st to the 256th images out of the 256 images H1(1) to H1(256).

(S35: Form Tentative Image Set)

The selecting processor 821 forms a tentative image set based on (one or more) image group(s) obtained up to the present point of time. At the current stage of the present example, the selecting processor 821 forms a tentative image set that includes the 156 images H1(1) to H1(70) and H1(171) to H1(256).

(S36: Number of Selected Images=Predetermined Number?)

The selecting processor 821 compares the number of images included in the tentative image set formed (that is, the number of images selected) in the immediately preceding step S35 with a predetermined number of images. As described above, the predetermined number of images (the number of images included in an image set) is set to the number 256 in the present example.

When the number of images included in the tentative image set reaches the number 256 (S36: Yes), the operation proceeds to the step S38. If the number of images included in the tentative image set does not reach the number 256 (S36: No), the operation proceeds to the step S37.

(S37: Number of Scans=Predetermined Number?)

The selecting processor 821 compares the number of scans performed up to the present stage (the number of times of the repetitions of the alternate execution of the scan application and the image selection) with a predetermined number of times. As described above, the predetermined number of times may be set to five in the present example.

When the number of scans performed up to the current stage reaches five (S37: Yes), the operation proceeds to the step S38. If the number of scans performed up to the current stage does not reach five (S37: No), the operation returns to the step S33.

The present example repeats the steps S33 to S37 until "Yes" is issued as a result of the determination of the step S36 or until "Yes" is issued as a result of the determination of the step S37. Having a determination result "Yes" in the step S36 corresponds to the fact that images of the number required for forming the image set (256 images) have been prepared. Further, having a determination result "Yes" in the step S37 corresponds to the fact that the scan application and the image selection have been repeated for the maximum number of times.

(S38: Form Image Set)

When it is determined to be "Yes" in the step S36 or S37, the image set forming processor 82 forms an image set based on a tentative image set formed in the immediately preceding step S35 in the same manner as in the first aspect example.

Given now is a description of specific examples of the steps S33 to S38. As mentioned above, the example shown in FIG. 10A forms a tentative image set including the 156 images H1(1) to H1(70) and H1(171) to H1(256) (the step S35), based on the first scan (the step S33) and the image selection of the first time (the step S34).

At the current stage, the number of images included in the tentative image set has not reached the number 256 (S36: No), and thus, the operation proceeds to the step S37. Since the scan has been performed only once up to the current stage (S37: No), the operation returns to the step S33.

Upon returning to the step S33, the anterior segment scan of the second time (second scan) is performed. 256 images obtained by the second scan are denoted by H2(1) to H2(256), respectively. As in the image group obtained by the first scan, the 256 images H2(1) to H2(256) are assigned to 256 positions ordered in the scan area. Further, the image H1($n$) obtained by the first scan and the image H2($n$) obtained by the second scan are associated with each other by referring to the 256 positions ($n$=1, 2, . . . , 256). The same applies to an image group obtained by each subsequent scan.

Figure 10B:
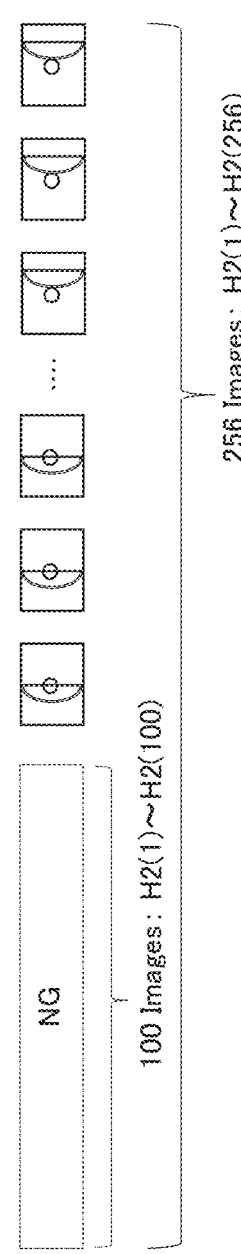
FIG. 10B is a schematic diagram for describing an operation of a slit lamp microscope according to an aspect example.

In the step S34, the selecting processor 821 selects an image satisfying a predetermined image selection condition from the 256 images H2(1) to H2(256) acquired in the step S33. As shown in FIG. 10B, the present example makes a premise that the 100 images H2(1) to H2(100) of the first to the 100th images do not satisfy the image selection condition, and the 156 images H2(101) to H2(256) of the 101st to the 256th images satisfy the image selection condition. In this case, the selecting processor 821 selects the 156 images H2(101) to H2(256) of the 101st to the 256th images from the 256 images H2(1) to H2(256).

When two or more images corresponding to a certain position in the scan area are selected, the selecting processor 821 may further select one image from the two or more images. In the examples shown in FIG. 10A and FIG. 10B, for example, the image H1(256) and the image H2(256) are selected as the above two or more images corresponding to the 256th position.

The selecting processor 821 may be configured to execute a process of selecting one of the image H1(256) and the image H2(256). For example, the selecting processor 821 may be configured to select the image H1(256) acquired first or the image H2(256) acquired later. In the present example, the selecting processor 821 is supposed to be configured to select the image acquired prior to the other.

In another example, the selecting processor 821 may be configured to select one image through comparison between the image H1(256) and the image H2(256). For example, the selecting processor 821 may be configured to calculate an image quality assessment value of the image H1(256), calculate an image quality assessment value of the image H2(256), and compare these image quality assessment values to select one of the image H1(256) and the image H2(256). Typical examples are configured to select the image with the highest image quality assessment value.

By such processing, at most one image is assigned to each of the 256 positions in the scan area. In other words, the maximum number of images included in a tentative image set is the number 256.

The selecting processor 821 forms a tentative image set based on the two image groups (namely, the image group H1(1) to H1(256) and the image group H2(1) to H2(256)) obtained up to the present point of time. At the current stage of the present example, a tentative image set is formed that includes the 156 images H1(1) to H1(70) and H1(171) to H1(256) based on the first scan, and the 70 images H2(101) to H2(170) based on the second scan.

In other words, the tentative image set obtained at this stage includes the 226 images H1(1) to H1(70), H2(101) to H2(170), and H1(171) to H1(256) corresponding to the first to the 70th positions and the 101st to the 256th positions (226 positions) of the 256 positions in the scan area.

At this stage, the number of images included in the tentative image set has not reached the number 256 (S36: No), thus, the operation proceeds to the step S37. At this stage, since the scan has been performed only twice (S37: No), the operation returns to the step S33 again.

When the operation returns to the step S33, the anterior segment scan of the third time (third scan) is performed. 256 images obtained by the third scan are denoted by H3(1) to H3(256), respectively.

Figure 10C:
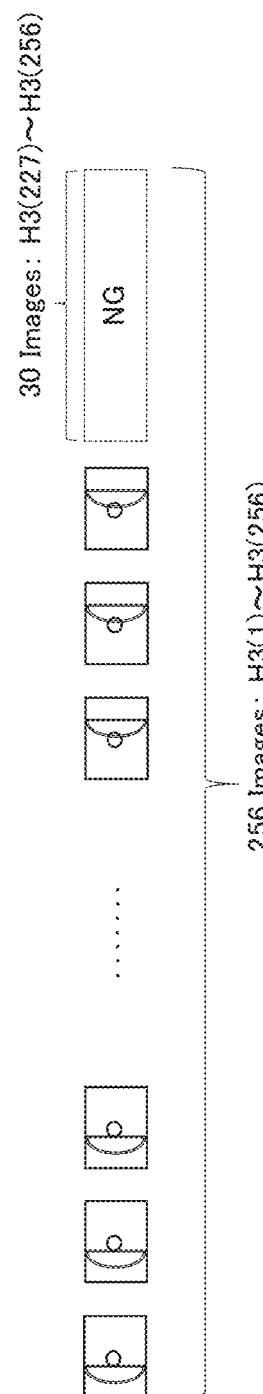
FIG. 10C is a schematic diagram for describing an operation of a slit lamp microscope according to an aspect example.

In the step S34, the selecting processor 821 selects an image that satisfies a predetermined image selection condition from the 256 images H3(1) to H3(256) acquired in the step S33. As shown in FIG. 10C, the present example makes a premise that the 30 images H3(227) to H3(256) of the 227th to the 256th images do not satisfy the image selection condition, and the 226 images H3(1) to H3(226) of the first to the 226th images satisfy the image selection condition. In this case, the selecting processor 821 selects the 226 images H3(1) to H3(226) of the first to the 226th images from the 256 images H3(1) to H3(256).

Furthermore, excluding the first to the 70th positions and the 101st to the 256th positions, among the 256 positions in the scan area, to each of which a corresponding image has already been assigned, the selecting processor 821 selects the 30 images H3(71) to H3(100) corresponding to the 71st to the 100th positions from the 226 images H3(1) to H3(226).

The selecting processor 821 forms a tentative image set based on the three image groups obtained up to the present point of time, namely, the image group H1(1) to H1(256), the image group H2(1) to H2(256), and the image group H3(1) to H3(256). At the current stage of the present example, the selecting processor 821 forms a tentative image set that includes the 156 images H1(1) to H1(70) and H1(171) to H1(256) based on the first scan, the 70 images H2(101) to H2(170) based on the second scan, and the 30 images H3(71) to H3(100) based on the third scan.

In other words, the tentative image set formed at this stage includes the 256 images H1(1) to H1(70), H3(71) to H3(100), H2(101) to H2(170), and H1(171) to H1(256) that respectively corresponds to all the 256 positions in the scan area. In this case, "YES" is issued as a result of the determination of the step S36, and the operation shifts to the step S38.

In the step S38, the image set forming processor 82 forms an image set based on the 256 images included in the tentative image set formed in the immediately preceding step S35, that is, based on the 256 images H1(1) to H1(70), H3(71) to H3(100), H2(101) to H2(170), and H1(171) to H1(256).

The operation shown in FIG. 9A provides an example of processing for forming an image set using the alternate execution of scan application and image selection. Following this processing, the operation shown in FIG. 9B is executed.

(S39: Assess Quality of Image Set)

The image set assessing processor 83 assesses the quality of the image set formed in the step S38 in the same fashion as in the first aspect example.

Alternatively, the present aspect example may be configured to perform an assessment of the quality of an image set using a moving image acquired by the moving image acquisition unit 40 in the manner described above. In an example of such assessment, processed is an image set formed based on the examples shown in FIG. 10A to FIG. 10C that includes the series of 256 images H1(1) to H1(70), H3(71) to H3(100), H2(101) to H2(170), and H1(171) to H1(256). Three times of scans have been performed to collect these images while moving image photography has been performed by the moving image acquisition unit 40 in parallel with each of the three times of scans.

Among a frame group obtained by the moving image photography performed in parallel with the first scan, a frame associated with the image H1($n$) is denoted by J1($n$) ($n$=1, 2, . . . , 256). Further, among a frame group obtained by the moving image photography performed in parallel with the second scan, a frame associated with the image H2($n$) is denoted by J2($n$) ($n$=1, 2, . . . , 256). In addition, among a frame group obtained by the moving image photography performed in parallel with the third scan, a frame associated with the image H3($n$) is denoted by J3($n$) ($n$=1, 2, . . . , 256).

In this way, the 256 images H1(1) to H1(70), H3(71) to H3(100), H2(101) to H2 (170), and H1(171) to H1(256) included in the image set of the present example, are associated with the frames J1(1) to J1(70), J3(71) to J3(100), J2(101) to J2(170), and J1(171) to J1(256), respectively.

The image set assessing processor 83 may be configured to execute an assessment of the image set of the present example, by applying the same or similar processing as or to the above-mentioned processing performed on the frame group D1 to DN, to the 256 frames respectively associated with the 256 images included in the image set of the present example.

(S40: Satisfactory Quality?)

In the case where the image set assessing processor 83 has determined in the step S39 that the quality of the image set is satisfactory (S40: Yes), the operation proceeds to the step S43. On the other hand, in the case where the image set assessing processor 83 has determined in the step S39 that the quality of the image set is not satisfactory (S40: No), the operation shifts to the step S41.

(S41: Suggest Re-Photographing)

In the case where the image set assessing processor 83 has determined in the step S39 that the quality of the image set is not satisfactory (S40: No), the controller 7 then performs a control to display information and/or a control to perform audio (voice) output of information in order to suggest the user to re-conduct photography in the same manner as in the first aspect example.

(S42: Re-Photographing?)

As a response to the information displayed and/or output with audio or voice in the step S41, the user performs an operation of issuing an instruction to commence re-photographing or an operation of issuing an instruction not to re-perform photography.

In the case where the user performs the operation of issuing an instruction to start re-photographing (S42: Yes), the operation returns to the step S31. In this case, the slit lamp microscope executes again the series of processes up to this step. Note that the re-photographing can be repeated up to a predetermined number of times, for example.

On the other hand, in the case where the user performs the operation of issuing an instruction not to re-perform photography (S42: No), the operation proceeds to the step S43.

(S43: Transmit Image Set)

In the case where the image set assessing processor 83 has determined in the step S39 that the quality of the image set is satisfactory (S40: Yes), or in the case where the user has performed, in the step S42, the operation of issuing an instruction not to re-perform photography (S42: No), the controller 7 then controls the communication device 9 to transmit the image set to an image interpretation computer terminal and/or to an image interpretation apparatus.

(S44: Perform Image Interpretation of Image Set)

The image interpretation computer terminal is a computer used by doctors to conduct image interpretation. The image interpretation apparatus is a computer that has a function of executing image interpretation processing.

In the case where the image set is transmitted to the image interpretation computer terminal in the step S43, a doctor conducts image interpretation of the series of images included in this image set using the image interpretation computer terminal. In the case where the image set is transmitted to the image interpretation apparatus in the step S43, the image interpretation apparatus executes image interpretation of this image set.

(S45: Generate Image Interpretation Report)

In the case where a doctor conducts image interpretation in the step S44, the doctor inputs a result of the image interpretation into a predetermined report template. In the case where the image interpretation apparatus executes image interpretation in the step S44, the image interpretation apparatus inputs a result of the image interpretation into a predetermined report template. Thus, an image interpretation report for this image set is formed.

(S46: Save Image Set and Image Interpretation Report)

The image set and the image interpretation report are provided to, for example, the facility where the slit lamp microscope 1 is installed, the medical institution designated by the subject or the like, the information processing apparatus used by a doctor designated by the subject or the like, and the address information (e.g., email address, postal address, etc.) registered by the subject or the like, and then stored (saved). In some aspect examples, the image set and the image interpretation report may be transmitted to a predesignated database system to be stored and managed.

This concludes the description of the operation according to the present example.

Some advantageous effects achieved by the slit lamp microscope of the present aspect example will be described. Note that advantageous effects common to the slit lamp microscope 1 of the first aspect example will not be described again here unless otherwise mentioned.

In the alternate execution of scan application and image selection, the slit lamp microscope of the present aspect example is capable of preventing positional deviations of the subject's eye between the repetitive scan applications by acquiring substantially the same anterior segment images at the individual points of time of the commencements of the repetitive scan applications. To this end, the slit lamp microscope of the present aspect includes, in addition to the elements of the first aspect example, the moving image acquisition unit 40 (photography unit) configured to perform photography of the anterior segment of the subject's eye from a fixed position. The controller 7 is configured to control the scanner to commence the second scan in response to an event that the moving image acquisition unit 40 has acquired an image substantially the same as a reference image that has been acquired by the moving image acquisition unit 40 in response to commencement of the first scan.

The slit lamp microscope of the present aspect example is capable of referring to a moving image (frame group) acquired by the moving image acquisition unit 40 in the quality assessment of an image set. To achieve this, the slit lamp microscope of the present aspect example includes, in addition to the elements of the first aspect example, the moving image acquisition unit 40 configured to acquire a moving image of the anterior segment of the subject's eye from a fixed position in parallel with scan application to the anterior segment. The image set assessing processor 83 is configured to perform a quality assessment of an image set based on a moving image acquired by the moving image acquisition unit 40.

Further, the image set assessing processor 83 may be configured to perform the quality assessment of an image set based on a correspondence between a series of images included in this image set and a series of frames included in a moving image acquired by the moving image acquisition unit 40.

In addition, the image set assessing processor 83 may be configured to perform the quality assessment of an image set based on a landmark in a series of frames included in a moving image acquired by the moving image acquisition unit 40 and a correspondence between a series of images included in this image set and the series of frames included in the moving image.

With such an image set assessment executed by the present aspect example, it becomes possible to provide an assessment method or technique different from that of the first aspect example. It should be noted that whether to employ the assessment method or technique of the present aspect example or that of the first aspect example may be optional.

Third Aspect Example

The present aspect example gives a description of an ophthalmic system including an ophthalmic imaging apparatus, an information processing apparatus, and an image interpretation computer terminal. The ophthalmic imaging apparatus has at least a function as a slit lamp microscope. The slit lamp microscope included in the ophthalmic imaging apparatus may be the slit lamp microscope of the first aspect example or the slit lamp microscope of the second aspect example. Below, a description will be given while referring accordingly to the elements, the configurations, and the reference characters of the first aspect example and/or those of the second aspect example.

Figure 11:
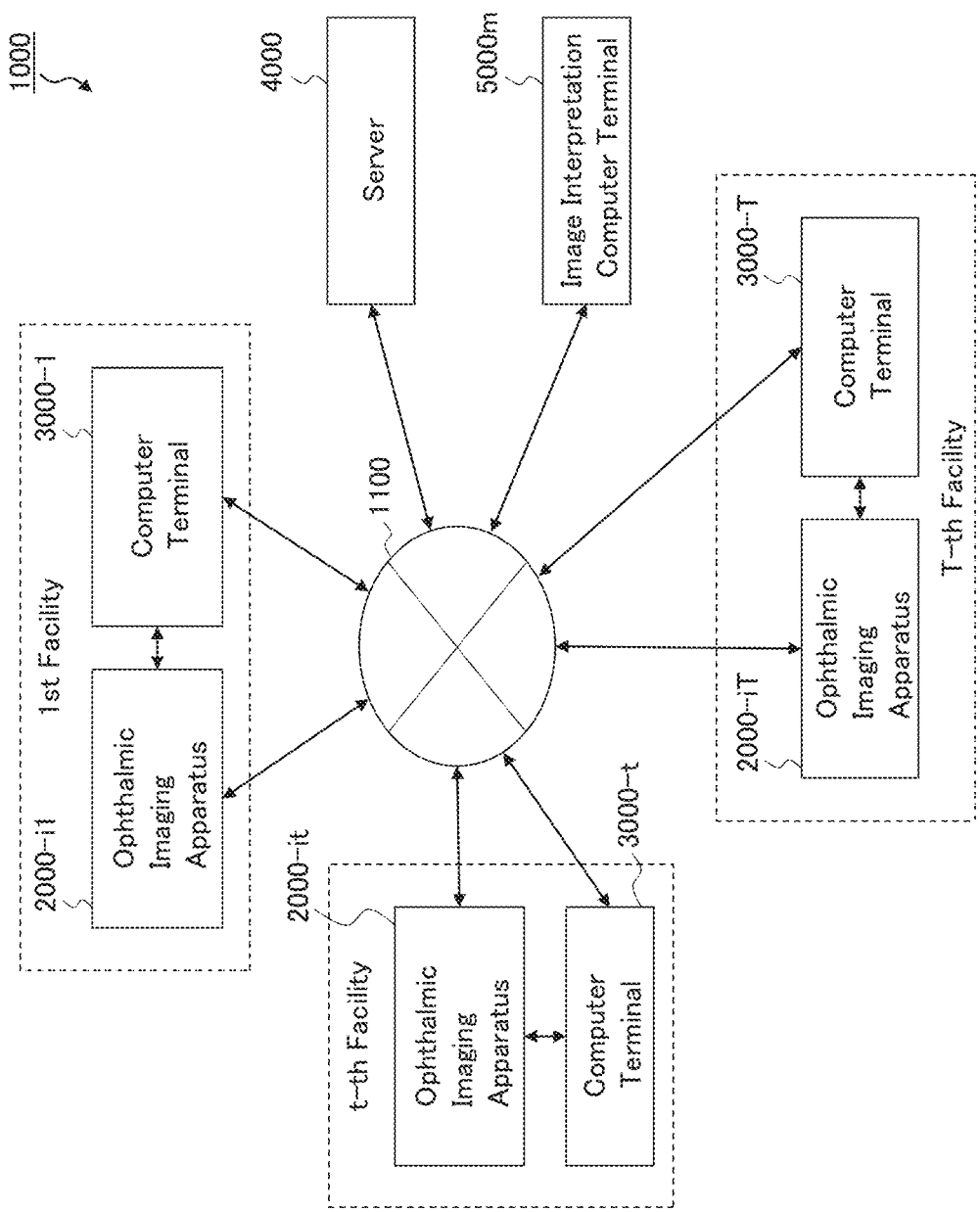
FIG. 11 is a schematic diagram illustrating a configuration of an ophthalmic system according to an aspect example.

The ophthalmic system 1000 illustrated in FIG. 11 is configured using a communication channel (communication line) 1100 that is used for establishing connections between each of the T number of facilities (the first facility to the T-th facility) where ophthalmic imaging is conducted, the server 4000, and the image interpretation computer terminal 5000$m$.

Here, the ophthalmic imaging includes at least anterior segment photography using a slit lamp microscope. This anterior segment photography includes at least the anterior segment scanning with slit light described in the first and/or second aspect examples.

Each of the facilities (t-th facility: where t=1 to T, T is any positive integer) is provided with the ophthalmic imaging apparatus 2000-$i_t$ (where $i_t$=1 to $K_t$, $K_t$ is any positive integer). In other words, one or more ophthalmic imaging apparatuses 2000-$i_t$ are installed in each of the facilities (t-th facility). The ophthalmic imaging apparatus 2000-$i_t$ constitutes a part of the ophthalmic system 1000. Incidentally, the ophthalmic system 1000 may include an examination apparatus that is capable of performing examination other than ophthalmic examination.

The ophthalmic imaging apparatus 2000-$i_t$ of the present example has the function of an "imaging apparatus" that performs imaging of eyes, and the function of a "computer" that performs various kinds of data processing and communicates with external devices. For another example, an imaging apparatus and a computer may be provided separately from each other. If this is the case, the imaging apparatus and the computer may communicate with each other. There may be any number of imaging apparatuses and any number of computers. For example, a single computer and a plurality of imaging apparatuses can be provided.

The "imaging apparatus" in the ophthalmic imaging apparatus 2000-$i_t$ includes at least a slit lamp microscope. This slit lamp microscope may be the slit lamp microscope of the first or second aspect example.

Each of the facilities (t-th facility) is provided with an information processing apparatus that can be used by an assistant or a subject (that is, the computer terminal 3000-$t$). The computer terminal 3000-$t$ is a computer for use in the corresponding facility. The computer terminal 3000-$t$ may be, for example, a mobile terminal such as a tablet terminal or a smartphone, or a server installed in the corresponding facility. The computer terminal 3000-$t$ may also include a wearable device such as a wireless earphone. Note that the computer terminal 3000-$t$ is only required to be a computer capable of realizing its functions in the corresponding facility. The computer terminal 3000-$t$ may be, for example, a computer placed outside the corresponding facility such as a cloud server.

The ophthalmic imaging apparatus 2000-$i_t$ and the computer terminal 3000-$t$ may communicate with each other through a network such as a network built in the t-th facility (e.g., in-house LAN), a wide area network (e.g., the Internet), or near-field communication technology.

The ophthalmic imaging apparatus 2000-$i_t$ may have the function as a communication device such as a server. If this is the case, the ophthalmic imaging apparatus 2000-$i_t$ and the computer terminal 3000-$t$ may communicate directly with each other. This makes it possible for the server 4000 and the computer terminal 3000-$t$ to communicate with each other via the ophthalmic imaging apparatus 2000-$i_t$. Therefore, the function of performing communication between the computer terminal 3000-$t$ and the server 4000 becomes omissible.

The server 4000 of some typical examples is installed in a facility different from any of the first to the T-th facilities, for example, in a management center. The server 4000 can communicate with the image interpretation computer terminal 5000$m$ (where m=1 to M, M is any positive integer) via a network. The network is, for example, a LAN or a wide area network. Further, the server 4000 can communicate with at least one of the ophthalmic imaging apparatuses 2000-$i_t$ installed in the first to the T-th facilities via a wide area network.

The server 4000 has the following functions, for example: the function of relaying communication between the ophthalmic imaging apparatus 2000-$i_t$ and the image interpretation computer terminal 5000$m$; the function of recording the contents of the communication; the function of storing data and information acquired by the ophthalmic imaging apparatus 2000-$i_t$; and the function of storing data and information acquired by the image interpretation computer terminal 5000$m$. In addition, the server 4000 may have a data processing function.

The image interpretation computer terminal 5000$m$ includes a computer that can be used for interpretation of images of a subject's eye (e.g., a plurality of anterior segment images included in an image group or an image set, or a rendered image of a three dimensional image constructed based on the anterior segment images included in the image group or the image set) acquired by the ophthalmic imaging apparatus 2000-$i_t$ and that can be used for generation of a report. The image interpretation computer terminal 5000$m$ may have a function of data processing.

Figure 12:
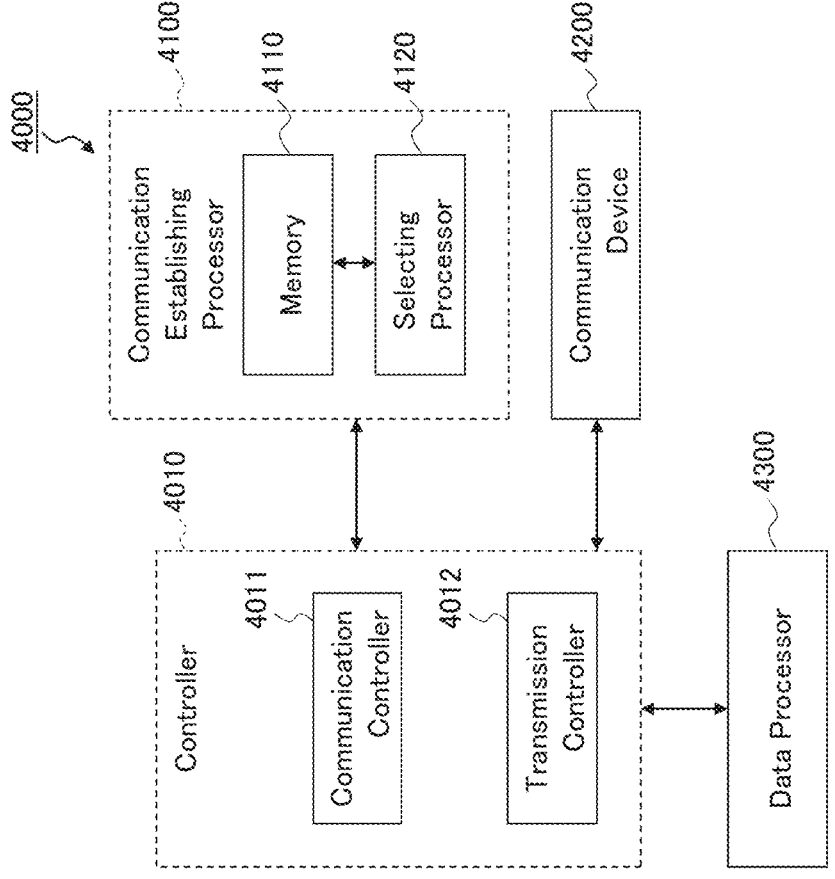
FIG. 12 is a schematic diagram illustrating a configuration of an ophthalmic system according to an aspect example.

Now given is a description of the server 4000. The server 4000 illustrated in FIG. 12 includes the controller 4010, the communication establishing processor 4100, and the communication device 4200.

The controller 4010 executes a control of each part of the server 4000. The controller 4010 may be capable of executing other processing such as arithmetic processing. The controller 4010 includes a processor. The controller 4010 may further include a RAM, a ROM, a hard disk drive, a solid state drive, etc.

The controller 4010 includes the communication controller 4011 and the transmission controller 4012.

The communication controller 4011 is configured to perform a control relating to the establishment of communication between a plurality of apparatuses that includes a plurality of ophthalmic imaging apparatuses 2000-$i_t$, a plurality of computer terminals 3000-$t$, and a plurality of image interpretation computer terminals 5000$m$. For example, the communication controller 4011 may be configured to send a control signal for establishing communication to each of two or more apparatuses selected by the selecting processor 4120 from among a plurality of apparatuses included in the ophthalmic system 1000. The selecting processor 4120 will be described later.

The transmission controller 4012 is configured to perform a control relating to exchange (transmission and reception) of information between two or more apparatuses between which communication has been established by the communication establishing processor 4100 (and the communication controller 4011). For example, the transmission controller 4012 may be configured to transfer information transmitted from one of the at least two apparatuses between which communication has been established by the communication establishing processor 4100 (and the communication controller 4011), to another apparatus.

As a specific example, in the case where communication between the ophthalmic imaging apparatus 2000-$i_t$ and the image interpretation computer terminal 5000$m$ has been established, the transmission controller 4012 can transfer information transmitted from the ophthalmic imaging apparatus 2000-$i_t$ to the image interpretation computer terminal 5000$m$. This information transmitted from the ophthalmic imaging apparatus 2000-$i_t$ may include an image group or an image set. Conversely, the transmission controller 4012 can transfer information transmitted from the image interpretation computer terminal 5000$m$ to the ophthalmic imaging apparatus 2000-$i_t$. This information transmitted from the image interpretation computer terminal 5000$m$ may include an instruction to the ophthalmic imaging apparatus 2000-$i_t$, an image interpretation report, or the like.

The transmission controller 4012 may have a function of processing information received from another apparatus. If this is the case, the transmission controller 4012 can transmit at least one of the received information and information generated using the processing function, to an apparatus that is a destination of transfer.

For example, the transmission controller 4012 may extract part of the information transmitted from an apparatus such as the ophthalmic imaging apparatus 2000-$i_t$, and transmit the extracted information to an apparatus such as the image interpretation computer terminal 5000$m$. For example, the transmission controller 4012 may extract a series of images from an image group or an image set transmitted from the ophthalmic imaging apparatus 2000-$i_t$ and then transmit the series of images to the image interpretation computer terminal 5000$m$.

In some aspect examples, the server 4000 or another apparatus may be configured to analyze information transmitted from an apparatus such as the ophthalmic imaging apparatus 2000-$i_t$. This information to be analyzed may include an image group or an image set, for example. In addition, a result of this analysis of the information (and the original information) may be sent to an apparatus such as the image interpretation computer terminal 5000$m$. Some aspect examples may be configured to execute interpretation of an image group or an image set transmitted from the ophthalmic imaging apparatus 2000-$i_t$ using an artificial intelligence engine or the like, and to transmit a result of this interpretation to the image interpretation computer terminal 5000$m$ together with the image group or the image set.

In the case where an image group or an image set has been transmitted from the ophthalmic imaging apparatus 2000-$i_t$, the server 4000 or another apparatus may construct a three dimensional image (e.g., stack data or volume data) from a series of images included in the image group or the image set, and then the transmission controller 4012 may send the constructed three dimensional image to the image interpretation computer terminal 5000$m$.

In the case where stack data has been transmitted from the ophthalmic imaging apparatus 2000-$i_t$, the server 4000 or another apparatus may construct volume data from this stack data, and then the transmission controller 4012 may send the constructed volume data to the image interpretation computer terminal 5000$m$.

Data processing executable by the server 4000 or another apparatus is not limited to the examples described above. Data processing executable by the server 4000 or another apparatus may include data processing of any kind. For example, the server 4000 or another apparatus may be capable of performing a process such as rendering of a three dimensional image, artifact elimination, distortion correction, measurement, or the like.

The communication establishing processor 4100 is configured to perform processing of establishing communication between at least two apparatuses that have been selected from among a plurality of apparatuses including the plurality of ophthalmic imaging apparatuses 2000-$i_t$, the plurality of computer terminals 3000-$t$, and the plurality of image interpretation computer terminals 5000$m$. In the present aspect example, "establishing communication" refers to a concept which includes, for example, at least one of the following options: (1) establishing unidirectional communication from a state in which communication is disconnected; (2) establishing bidirectional communication from a state in which communication is disconnected; (3) switching from a state in which only data reception is possible to a state in which both data reception and data transmission are possible; and (4) switching from a state in which only data transmission is possible to a state in which both data transmission and data reception are possible.

In addition, the communication establishing processor 4100 can perform processing of disconnecting the established communication. In the present aspect example, "disconnecting communication" refers to a concept which includes, for example, at least one of the following options: (1) disconnecting communication from a state in which unidirectional communication has been established; (2) disconnecting communication from a state in which bidirectional communication has been established; (3) switching from a state in which bidirectional communication has been established to unidirectional communication; (4) switching from a state in which data transmission and data reception are possible to a state in which only data reception is possible; and (5) switching from a state in which data transmission and data reception are possible to a state in which only data transmission is possible.

Each of the ophthalmic imaging apparatus 2000-$i_t$, the computer terminal 3000-$t$, and the image interpretation computer terminal 5000$m$ can send at least one of the following communication requests to the server 4000: a communication request (a call request) for calling another apparatus or the user thereof; and a communication request (an interruption request) for interrupting communication between two other apparatuses. A call request is issued manually or automatically, and an interruption request is issued manually or automatically. The server 4000 (the communication device 4200 therein) receives a communication request transmitted from the ophthalmic imaging apparatus 2000-$i_t$, the computer terminal 3000-$t$, or the image interpretation computer terminal 5000$m$.

The communication establishing processor 4100 of the present aspect example may include the selecting processor 4120. For example, based on a communication request sent from the ophthalmic imaging apparatus 2000-$i_t$, the computer terminal 3000-$t$, or the image interpretation computer terminal 5000$m$, the selecting processor 4120 selects one or more apparatuses other than the apparatus that has sent the communication request, from among the ophthalmic imaging apparatus 2000-$i_t$, the computer terminal 3000-$t$, and the image interpretation computer terminal 5000$m$.

A specific example of the processing executed by the selecting processor 4120 will be described. When a communication request sent from the ophthalmic imaging apparatus 2000-$i_t$ or the computer terminal 3000-$t$ is received (e.g., when a request for interpretation of an image acquired by the ophthalmic imaging apparatus 2000-$i_t$ is received), the selecting processor 4120 selects, for example, any apparatus from among the plurality of image interpretation computer terminals 5000$m$. The communication establishing processor 4100 establishes communication between the selected image interpretation computer terminal 5000$m$, and at least one of the ophthalmic imaging apparatus 2000-$i_t$ and the computer terminal 3000-$t$.

The apparatus selection in response to a communication request is performed, for example, based on a preset attribute. Examples of the attribute include types of examination (e.g., types of imaging modalities, types of images, types of diseases, types of possible diseases), degrees of expertise required, levels of skills required, and types of languages. In the present example, for example, the specialized field and the level of skill of the person who conducts image interpretation are referred to. In order to implement the processing according to the present example, the communication establishing processor 4100 may include the memory 4110 in which attribute information prepared in advance is stored. This attribute information includes attributes of the image interpretation computer terminals 5000$m$ and/or attributes of users (doctors, optometrists) of the image interpretation computer terminals 5000$m$.

The identification of users may be carried out using user identifiers (user IDs) respectively assigned to users in advance. Further, the identification of the image interpretation computer terminals 5000$m$ may be carried out using, for example, apparatus identifiers or network addresses respectively assigned to apparatuses in advance. In a typical example, the attribute information includes attributes of each user such as the user's specialized field (e.g., the department, the specialized disease), the user's degree of expertise, the user's level of skills, or the types of languages the user is able to use.

When the selecting processor 4120 refers to the attribute information, a communication request to be sent from the ophthalmic imaging apparatus 2000-$i_t$, the computer terminal 3000-$t$, or the image interpretation computer terminal 5000$m$ may include information related to attributes. For example, an interpretation request (diagnosis request) to be transmitted from the ophthalmic imaging apparatus 2000-$i_t$ may include any of the following options: (1) information indicating the type of an imaging modality; (2) information indicating the type of images; (3) information indicating the name of a disease or the name of a possible disease; (4) information indicating the degree of difficulty in interpretation; and (5) information indicating a language used by a user of the ophthalmic imaging apparatus 2000-$i_t$ and/or a language used by a user of the computer terminal 3000-$t$.

Upon receiving such an interpretation request, the selecting processor 4120 may select one or more of the image interpretation computer terminals 5000$m$ based on this interpretation request and the attribute information stored in the memory 4110. In this selection processing, the selecting processor 4120 may compare the information related to attributes included in the interpretation request with information recorded in the attribute information stored in the memory 4110. With this comparison, the selecting processor 4120 selects, for example, the image interpretation computer terminal(s) 5000$m$ corresponding to a doctor(s) (or an optometrist(s)) who satisfies any of the following attributes: (1) a doctor who is specializing in a corresponding imaging modality; (2) a doctor who is specializing in a corresponding type of images; (3) a doctor who is specializing in a corresponding disease (or a corresponding possible disease); (4) a doctor who is capable of conducting interpretation of a corresponding level of difficulty; and (5) a doctor who is capable of using a corresponding language.

The correspondence between doctors or optometrists and the image interpretation computer terminals 5000$m$ may be made by, for example, referring to user IDs input, at the time of logging in, into the image interpretation computer terminals 5000$m$ (or to the ophthalmic system 1000).

The communication device 4200 is configured to perform data communication with another apparatus such as any of the ophthalmic imaging apparatus 2000-$i_t$, the computer terminal 3000-$t$, and the image interpretation computer terminal 5000$m$. The system of the data communication and encryption may be performed in the same manner as in the communication device provided in the ophthalmic imaging apparatus 2000-$i_t$ (the communication device 9 of the first aspect example).

The server 4000 includes the data processor 4300. The data processor 4300 is configured to execute various kinds of data processes. The data processor 4300 may be configured to process a plurality of anterior segment images or a three dimensional image acquired by the ophthalmic imaging apparatus 2000-$i_t$ (in particular, a slit lamp microscope). The data processor 4300 includes a processor, a primary storage, a secondary storage, and so forth. The secondary storage retains a data processing program or the like. The function of the data processor 4300 is implemented by cooperation of software such as the data processing program and hardware such as the processor.

The server 4000 may provide data obtained by the data processor 4300 to another apparatus. For example, in the case where the data processor 4300 constructs a three dimensional image from a plurality of anterior segment images acquired by the ophthalmic imaging apparatus 2000-$i_t$, the server 4000 can transmit the constructed three dimensional image to the image interpretation computer terminal 5000$m$ by using the communication device 4200. In the case where the data processor 4300 applies the rendering to a three dimensional image constructed by the ophthalmic imaging apparatus 2000-$i_t$ or the data processor 4300, the server 4000 can transmit the constructed rendered image to the image interpretation computer terminal 5000$m$ by using the communication device 4200. In the case where the data processor 4300 applies a measuring process to one or more anterior segment images or a three dimensional image, the server 4000 can transmit the obtained measurement data to the image interpretation computer terminal 5000$m$ by using the communication device 4200. In the case where the data processor 4300 applies the distortion correction to one or more anterior segment images or a three dimensional image, the server 4000 can transmit the corrected image to the image interpretation computer terminal 5000$m$ by using the communication device 4200.

Figure 13:
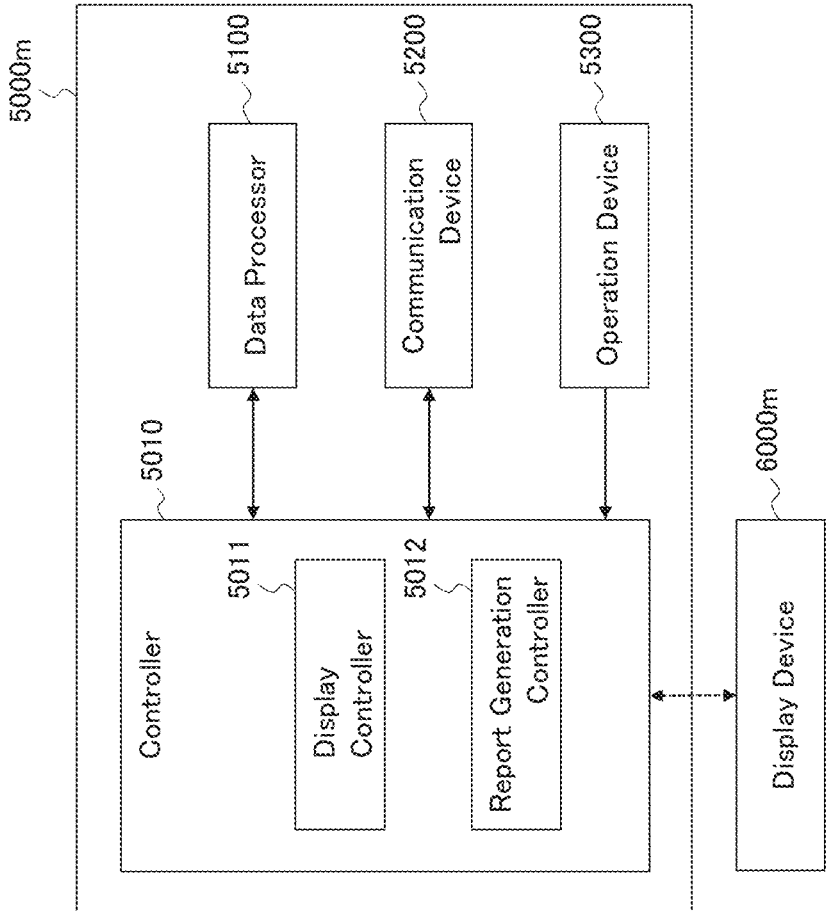
FIG. 13 is a schematic diagram illustrating a configuration of an ophthalmic system according to an aspect example.

Next, a description is given of the image interpretation computer terminal 5000$m$. The image interpretation computer terminal 5000$m$ illustrated in FIG. 13 includes the controller 5010, the data processor 5100, the communication device 5200, and the operation device 5300.

The controller 5010 executes a control of each part of the image interpretation computer terminal 5000m. The controller 5010 may be capable of executing other processing such as arithmetic processing. The controller 5010 includes a processor, a RAM, a ROM, a hard disk drive, a solid state drive, etc.

The controller 5010 includes the display controller 5011. The display controller 5011 controls the display device 6000m. The display device 6000m may be included in the image interpretation computer terminal 5000m or may be a peripheral device connected to the image interpretation computer terminal 5000m. The display controller 5011 controls the display device 6000m to display an image of the anterior segment of the subject's eye E (e.g., a series of images included in an image group or an image set).

The controller 5010 includes the report generation controller 5012. The report generation controller 5012 executes various kinds of controls for generating a report regarding the information displayed by the display controller 5011. For example, the report generation controller 5012 controls the display device 6000m to display a screen and a graphical user interface (GUI) used for report generation. Further, the report generation controller 5012 inputs or records, into or on a predetermined report template, information input by the user, an image of the anterior segment, measurement data, analysis data, and so forth.

The data processor 5100 executes various kinds of data processing. The data processor 5100 may be configured to process a plurality of anterior segment images or a three dimensional image acquired by the ophthalmic imaging apparatus 2000-$i_t$ (in particular, a slit lamp microscope). Further, the data processor 5100 may be configured to process a three dimensional image or a rendered image constructed by another information processing apparatus such as the server 4000. The data processor 5100 includes a processor, a primary storage, a secondary storage, and so forth. A data processing program or the like is stored in the secondary storage. The function of the data processor 5100 is implemented by cooperation of software such as the data processing program and hardware such as the processor.

The communication device 5200 performs data communication with another apparatus. This another apparatus is, for example, any of the ophthalmic imaging apparatus 2000-$i_t$, the computer terminal 3000-$t$, and the server 4000. The system of the data communication and encryption may be performed in the same manner as in the communication device of the ophthalmic imaging apparatus 2000-$i_t$.

The operation device 5300 is used to operate the image interpretation computer terminal 5000m and input information into the image interpretation computer terminal 5000m. In the present aspect example, the operation device 5300 is used to generate a report. The operation device 5300 includes an operation device and an input device. The operation device 5300 includes, for example, a mouse, a keyboard, a trackball, an operation panel, a switch, a button, a dial, or the like. The operation device 5300 may include a touch screen.

The ophthalmic system 1000 of the present aspect example is capable of performing the following operations.

To begin with, the ophthalmic imaging apparatus 2000-$i_t$ (a slit lamp microscope) performs scanning on the anterior segment of the subject's eye with slit light to collect an image group. In the case where a quality of this image group is assessed to be satisfactory, the ophthalmic imaging apparatus 2000-$i_t$ transmits the first transmission information that includes this image group to the server 4000 via the communication line 1100. On the other hand, in the case where a quality of this image group is assessed to be not satisfactory, the ophthalmic imaging apparatus 2000-$i_t$ applies two or more times of scans to the anterior segment, for example. The ophthalmic imaging apparatus 2000-$i_t$ forms an image set by selecting a series of images corresponding to a scan area, from two or more image groups collected through the two or more times of scans (and the above image group assessed to be of unsatisfactory quality). Further, the ophthalmic imaging apparatus 2000-$i_t$ transmits the first transmission information including the formed image set to the server 4000 via the communication line 1100. Such an operation of the ophthalmic imaging apparatus 2000-$i_t$ may be performed in the same manner as the operation of the first aspect example or the operation of the second aspect example. In addition, the ophthalmic imaging apparatus 2000-$i_t$ may be capable of performing any of the processes described in the first or second aspect example.

The server 4000 receives the first transmission information sent from the ophthalmic imaging apparatus 2000-$i_t$ using the communication device 4200 (a reception device), and then stores the first transmission information in the memory 4110. Further, the server 4000 transmits, using the communication device 4200 (a transmission device), the second transmission information that includes at least the image group or the image set included in the first transmission information, to the image interpretation computer terminal 5000m via the communication line 1100.

The image interpretation computer terminal 5000m receives the second transmission information sent from the server 4000 using the communication device 5200 (a reception device). The user of the image interpretation computer terminal 5000m (the person who conducts image interpretation) performs interpretation of the image group or the image set using a user interface (the operation device 5300, the display device 6000m, the report generation controller 5012, etc.). Then, the image interpretation computer terminal 5000m transmits, using the communication device 5200 (a transmission device), the third transmission information that includes information (e.g., an image interpretation report) input using the user interface, to the server 4000 via the communication line 1100.

The server 4000 receives the third transmission information transmitted from the image interpretation computer terminal 5000m using the communication device 4200 (a reception device), associates the third transmission information with the first transmission information, and stores the third transmission information in the memory 4110.

The ophthalmic system 1000 thus configured is capable of providing a doctor (a person who conducts image interpretation) with an image group or an image set having a good quality formed based on one or more times of scans applied to the anterior segment of the subject's eye. This makes it possible to widely provide high quality slit lamp microscope examinations.

In addition, a doctor conducts a medical examination while performing an operation of a slit lamp microscope from a remote place with a conventional technology; however, according to the present aspect example, a doctor only needs to conduct image interpretation of an image group or an image set that has been acquired in advance. In other words, according to the present aspect example, a doctor can be made free from the time and effort required for conducting photography, which allows the doctor to concentrate on image interpretation. Therefore, the present aspect example contributes to expanding the area (scope) in which a slit lamp microscope examination of a high quality can be provided.

Fourth Aspect Example

The present aspect example gives a description of an ophthalmic system that includes an ophthalmic imaging apparatus, an information processing apparatus, and an image interpretation apparatus. The difference in configurations from the third aspect is that the image interpretation apparatus is provided instead of the image interpretation computer terminal. Note that the third aspect example and the fourth aspect example may be combined to configure an ophthalmic system that includes both an image interpretation computer terminal and an image interpretation apparatus. Below, a description will be provided while referring accordingly to the elements, the configurations, and the reference characters of any of the first, second, and third aspect examples.

Figure 14:
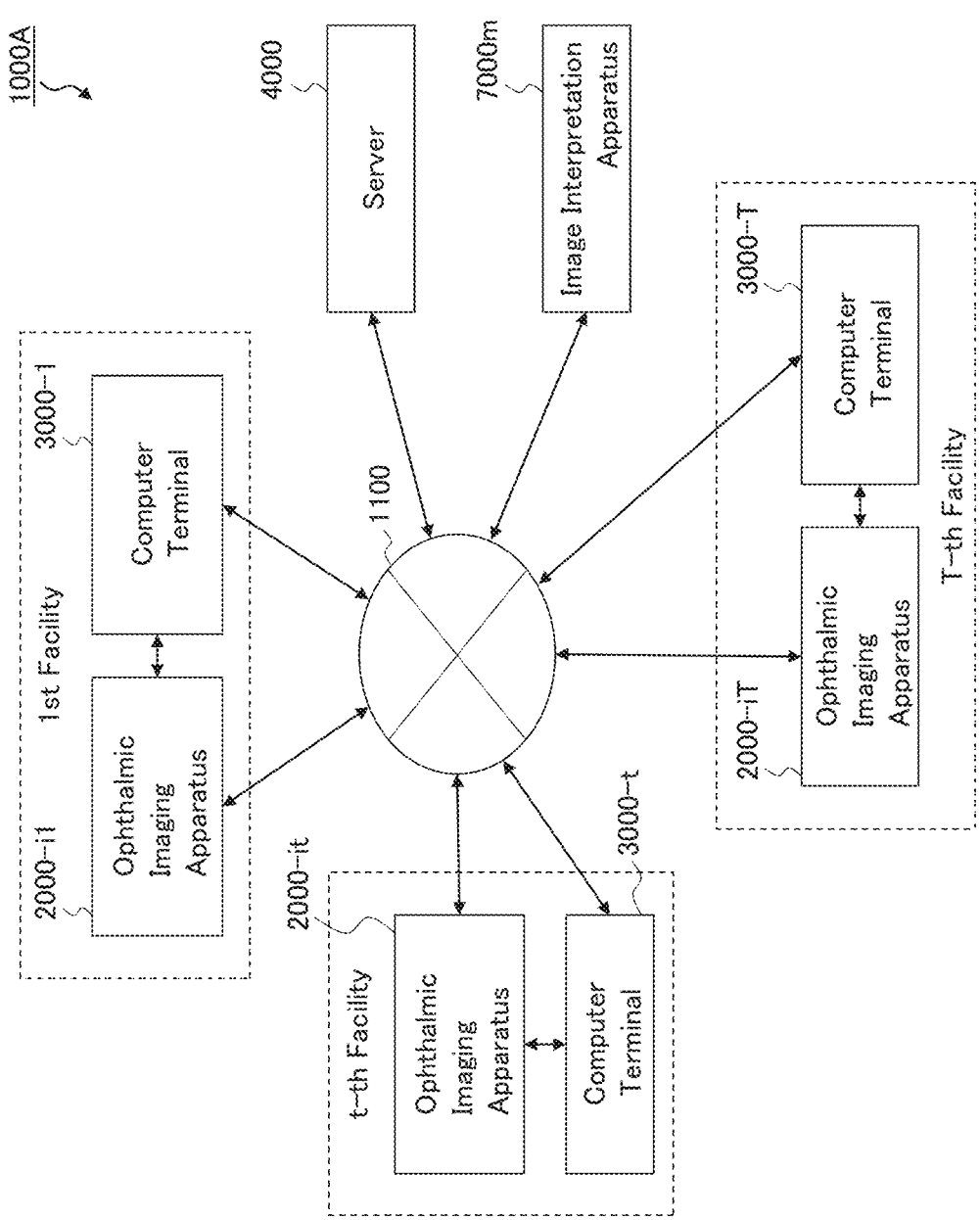
FIG. 14 is a schematic diagram illustrating a configuration of an ophthalmic system according to an aspect example.

The ophthalmic system 1000A illustrated in FIG. 14 is configured by, as mentioned above, replacing the image interpretation computer terminal 5000$m$ of the ophthalmic system 1000 of the third aspect example with the image interpretation apparatus 7000$m$. The image interpretation apparatus 7000$m$ is a computer configured to execute interpretation of an image group or an image set acquired by the ophthalmic imaging apparatus 2000-$i_t$ (a slit lamp microscope) using an image processing processor or an artificial intelligence engine, for example.

Figure 15:
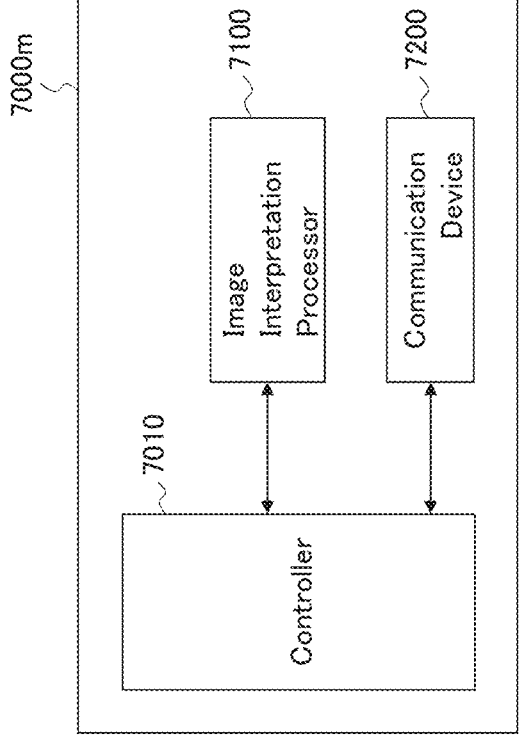
FIG. 15 is a schematic diagram illustrating a configuration of an ophthalmic system according to an aspect example.

FIG. 15 shows a configuration example of the image interpretation apparatus 7000$m$. The image interpretation apparatus 7000$m$ of the present example includes the image interpretation processor 7100 and the communication device 7200. The communication device 7200 is configured to perform data communication with another apparatus such as any of the ophthalmic imaging apparatus 2000-$i_t$, the computer terminal 3000-$t$, and the server 4000.

The image interpretation processor 7100 includes, for example, an image interpretation processor that operates in accordance with a program for image interpretation, and analyzes a series of images included in an image group or an image set to obtain findings. In some aspect examples, the image interpretation processor 7100 may include the artificial intelligence engine of the first aspect example, in order to obtain findings from a series of images included in an image group or an image set. In addition, the image interpretation processor 7100 may be configured to generate a report based on findings obtained.

The ophthalmic system 1000A of the present aspect example is capable of performing the following operations.

To begin with, the ophthalmic imaging apparatus 2000-$i_t$ (a slit lamp microscope) performs scanning on the anterior segment of the subject's eye with slit light to collect an image group. as in the third aspect, the present example is operated to apply one or more times of scans to the anterior eye segment and obtain an image group or an image set. Further, the present example is operated to transmit first transmission information that includes the image group or image set to the server 4000 via the communication line 1100.

The server 4000 receives the first transmission information sent from the ophthalmic imaging apparatus 2000-$i_t$ using the communication device 4200 (a reception device), and then stores the first transmission information in the memory 4110. Further, the server 4000 transmits, using the communication device 4200 (a transmission device), the second transmission information that includes at least the image group or the image set included in the first transmission information, to the image interpretation computer terminal 5000$m$ via the communication line 1100.

The image interpretation apparatus 7000$m$ receives the second transmission information sent from the server 4000 using the communication device 7200 (a reception device). The image interpretation apparatus 7000$m$ then executes processing of interpretation of the image group or the image set using the image interpretation processor 7100. The image interpretation apparatus 7000$m$ transmits, using means of the communication device 7200 (a transmission device), the fourth transmission information that includes information acquired by the image interpretation processor 7100, to the server 4000 via the communication line 1100.

The server 4000 receives the fourth transmission information transmitted from the image interpretation apparatus 7000$m$ using the communication device 4200 (a reception device), associates the fourth transmission information with the first transmission information, and stores the fourth transmission information in the memory 4110.

The ophthalmic system 1000A thus configured is capable of providing an image interpretation apparatus with an image group or an image set with a good quality formed based on one or more times of scans applied to the anterior segment of the subject's eye. This makes it possible to widely provide high quality slit lamp microscope examinations.

In addition, automatic image interpretation executed by the image interpretation apparatus of the present aspect example can support the work of a doctor (a person who conducts image interpretation). Therefore, the present aspect example contributes to expanding the area (scope) in which a slit lamp microscope examination of a high quality can be provided.

In the case where the image interpretation apparatus 7000$m$ includes an artificial intelligence engine and the ophthalmic imaging apparatus 2000-$i_t$ (a slit lamp microscope) also includes an artificial intelligence engine, the image interpretation apparatus 7000$m$ may be selected that is equipped with an artificial intelligence engine of the capability equivalent to that of the ophthalmic imaging apparatus 2000-$i_t$ (a slit lamp microscope) that has formed an image group or an image set, and then the image group or the image set may be transmitted to the image interpretation apparatus 7000$m$ selected.

This makes it possible to prevent inconveniences such as inconsistencies and errors between an output of the artificial intelligence engine of the ophthalmic imaging apparatus 2000-$i_t$ (a slit lamp microscope) and a corresponding output of the artificial intelligence engine of the image interpretation apparatus 7000$m$.

In the case not only where there is an ophthalmic system that includes both the image interpretation computer terminal 5000$m$ and the image interpretation apparatus 7000$m$, but also where there is no image interpretation apparatus 7000$m$ equipped with an artificial intelligence engine of the capability equivalent to that of the ophthalmic imaging apparatus 2000-$i_t$ (a slit lamp microscope) that formed an image group or an image set, this ophthalmic system may transmit the image group or the image set to the image interpretation computer terminal 5000$m$.

<Some Additional Matters and Items>

Some aspect examples described above are merely examples of the implementation of the present disclosure, and any modifications (e.g., omission, substitution, replacement, addition, etc.) may be made within the scope of the present disclosure to the above aspect examples.

The present disclosure provides a method of controlling a slit lamp microscope in accordance with any of the aspect examples described above. This slit lamp microscope includes a processor, and a scanner configured to perform scanning on the anterior segment of a subject's eye with slit light to collect an image group. To begin with, the present control method causes the processor to execute a control of the scanner for applying a scan to the anterior segment of the subject's eye. Further, the present control method causes the processor to execute an assessment of a quality of an image group acquired by the scanner. In addition, the present control method causes the processor to selectively execute two or more predetermined control modes according to a result of the assessment of the quality of the image group.

The present disclosure provides a program that causes a computer to execute the control method described above. In addition, the present disclosure provides a computer-readable non-transitory recording medium that stores such this program. The non-transitory recording medium may be in any form, and examples of the non-transitory recording medium include a magnetic disk, an optical disk, a magneto-optical disk, and a semiconductor memory.

Similarly, the present disclosure can provide any control method described in any of the first to the fourth aspect examples. Further, the present disclosure can provide any processing method (e.g., arithmetic method, calculating method, image processing method, image analysis method, etc.) described in any of the first to the fourth aspect examples. Furthermore, the present disclosure can provide a program that causes a computer to execute such a processing method. In addition, the present disclosure can provide a computer-readable non-transitory recording medium in which such a program is stored.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. A slit lamp microscope comprising:
a scanner configured to perform application of a scan to an anterior segment of a subject's eye with slit light to collect an image group;
a first assessing processor configured to execute an assessment of a quality of the image group collected by the scanner; and
a controller configured to selectively execute at least two control modes according to a result of the assessment of the quality obtained by the first assessing processor,
wherein the first assessing processor is configured to execute the assessment of the quality of the image group collected by the scanner using an inference model constructed by machine learning that uses training data including a plurality of anterior segment images,
a label is attached to each of the plurality of anterior segment images included in the training data, the label showing whether interpretation of a corresponding image is possible or impossible, and the inference model is constructed by supervised learning that uses the training data and configured to receive an input of an image obtained by scanning an anterior segment with slit light and output image interpretation possibility.

2. The slit lamp microscope according to claim 1, wherein the controller is configured to execute a control of the scanner to apply another scan to the anterior segment if the first assessing processor assesses that the quality of the image group is not satisfactory.

3. The slit lamp microscope according to claim 2, further comprising an image set forming processor configured to execute a formation of an image set by selecting a series of images corresponding to a scan area from at least two image groups that include the image group and another image group collected by the another scan.

4. The slit lamp microscope according to claim 3, wherein the image set forming processor includes a selecting processor configured to execute selection of an image that satisfies a predetermined condition from the at least two image groups.

5. The slit lamp microscope according to claim 4, wherein the selecting processor is configured to execute selection, from the at least two image groups, of an image that includes a reflected image of the slit light projected onto the anterior segment.

6. The slit lamp microscope according to claim 4, wherein the selecting processor is configured to execute selection of an image from the at least two image groups by comparing adjacent images.

7. The slit lamp microscope according to claim 4, wherein a plurality of positions is determined for the scan area, and the selecting processor is configured to execute image selection to assign at least one image to each of the plurality of positions.

8. The slit lamp microscope according to claim 4, wherein the controller is configured to execute a control of the scanner and the selecting processor to alternately execute application of a scan to the anterior segment and selection of an image from an image group collected by a corresponding scan.

9. The slit lamp microscope according to claim 8, wherein the selecting processor is configured to execute a formation of a tentative image set by selecting an image from at least one image group collected by at least one scan already performed.

10. The slit lamp microscope according to claim 9, wherein the selecting processor is configured to execute an update of the tentative image set by selecting an image from another image group collected by another scan when the another scan is applied after the at least one scan.

11. The slit lamp microscope according to claim 9, wherein the controller is configured to execute a control of the scanner and the selecting processor to terminate the application of the scan and the selection of the image when a number of images included in the tentative image set reaches a predetermined number.

12. The slit lamp microscope according to claim 9, wherein the controller is configured to execute a control of the scanner and the selecting processor to terminate the application of the scan and the selection of the image when a number of times of alternate execution of the application of the scan and the selection of the image reaches a predetermined number.

13. The slit lamp microscope according to claim 11, wherein the image set forming processor is configured to execute a formation of the image set based on the tentative image set acquired until termination of alternate execution of the application of the scan and the selection of the image.

14. The slit lamp microscope according to claim 3, further comprising a photography unit configured to perform photography of the anterior segment from a fixed position,
    wherein the controller is configured to execute a control of the scanner to commence a second scan when the photography unit acquires an image substantially a same as a reference image acquired by the photography unit in response to commencement of a first scan.

15. The slit lamp microscope according to claim 3, further comprising a second assessing processor configured to execute an assessment of a quality of the image set formed by the image set forming processor.

16. The slit lamp microscope according to claim 15, further comprising a moving image acquisition unit configured to perform acquisition of a moving image of the anterior segment from a fixed position in parallel with application of a scan to the anterior segment,
    wherein the second assessing processor is configured to execute the assessment of the quality based on the moving image acquired by the moving image acquisition unit.

17. The slit lamp microscope according to claim 1, wherein the first assessing processor includes
    a three dimensional image constructing processor configured to execute construction of a three dimensional image from the image group collected by the scanner, and
    a comparing processor configured to execute a comparison between at least one predetermined reference three dimensional image and the three dimensional image,
    wherein the first assessing processor is configured to execute the assessment of the quality of the image group based on a result of the comparison obtained by the comparing processor.

18. The slit lamp microscope according to claim 1, wherein the first assessing processor includes an assessment data generating processor configured to execute generation of image quality assessment data from an image included in the image group collected by the scanner,
    wherein the first assessing processor is configured to execute the assessment of the quality of the image group based on the image quality assessment data.

* * * * *